United States Patent [19]

Bouchaudon et al.

[11] Patent Number: 4,742,048
[45] Date of Patent: May 3, 1988

[54] TETRAPEPTIDES AND PENTAPEPTIDES, THEIR PREPARATION AND COMPOSITIONS CONTAINING THEM

[75] Inventors: Jean Bouchaudon, Morsang-Sur-Orge; Daniel Farge, Thiaias; Claude James, Paris, all of France

[73] Assignee: Rhone-Poulenc Industries, Paris, France

[21] Appl. No.: 163,890

[22] Filed: Jun. 27, 1980

[30] Foreign Application Priority Data

Jun. 29, 1979 [FR] France ................... 79 16845

[51] Int. Cl.$^4$ .................. A61K 37/02; C07K 5/08; C07K 5/10
[52] U.S. Cl. ............................ 514/17; 514/18; 530/330; 530/331
[58] Field of Search .............. 260/112.5 R; 514/17, 514/18; 530/330, 331

[56] References Cited

U.S. PATENT DOCUMENTS 4,261,979 4/1981 Solles et al. ................ 260/112.5 R
4,311,640 1/1982 Kuroda et al. ............... 260/112.5 R

FOREIGN PATENT DOCUMENTS 0011283 5/1980 European Pat. Off. ...... 260/112.5 R
0013856 6/1980 European Pat. Off. ...... 260/112.5 R
2033906 10/1979 United Kingdom .

OTHER PUBLICATIONS

Rudinger, *Peptide Harmones*, edited by Parsons, University Park Press, Baltimore, pp. 1–7.
Biochem–and Biophys. Res. Commun. 59, 1974 1317–1325.
Biochemistry vol. 9, No. 4, 1970, 823–831.
Comptes Rendus Hebdomandaires Des Scanies De L'Academic Des Sciences Paris pp. 1320–1304 (1965).
Bulletin De La Societe De Chimie Biologique 1967, 49, No. 11 pp. 1579–1591.
Agricultural and Biological Chemistry 41, (5) 763–768, 1977.
11th Internat'l Congress of Chemotherapy—19th Interscience Conference on Antimicrobial Agents & Chemotherapy (1979).
Life Sciences, vol. 26, pp. 883–888 Jan. 17, 1980.
C. R. Acad. Se. Paris, 1.289 (Sep. 24, 1979) Series D-473.

*Primary Examiner*—J. R. Brown
*Assistant Examiner*—F. T. Moezie
*Attorney, Agent, or Firm*—Stevens, Davis, Miller & Mosher

[57] ABSTRACT

Tetrapeptides and pentapeptides of the formula:

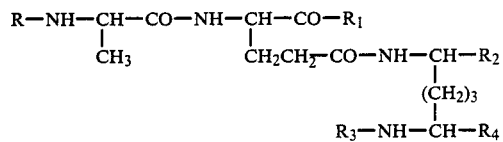

wherein R represents hydrogen or a fatty acid residue, $R_1$ represents hydroxy, amino, alkoxy of 1 to 4 carbon atoms, optionally substituted by phenyl or nitrophenyl, one of $R_2$ and $R_4$ represents hydrogen, carboxy, carbamoyl, alkoxycarbonyl of 2 to 5 carbon atoms, optionally substituted by phenyl or nitrophenyl, or a N-carbonylglycine or N-carbonyl-D-alanine radical optionally esterified by alkyl of 1 to 4 carbon atoms (which is optionally substituted by phenyl or nitrophenyl) and the other symbol represents hydrogen, carboxy, carbamoyl, or alkoxycarbonyl of 2 to 5 carbon atoms, optionally substituted by phenyl or nitrophenyl, and $R_3$ represents hydrogen, a fatty acid residue or a glycyl or D-alanyl moiety in which the amine group is optionally substituted by a fatty acid residue, it being understood that $R_2$ and $R_4$ cannot simultaneously represent hydrogen, that at least one of $R_2$, $R_3$ and $R_4$ represents a glycyl or D-alanyl moiety, that at least one of R and $R_3$ represents or contains a fatty acid residue, and that the alanine moiety is in the L form, the glutamic acid moiety or its derivatives are in the D form, the lysine moiety or its derivatives, when one of the symbols $R_2$ and $R_4$ represents a hydrogen atom, are in the L form, and the 2,6-diaminopimelic acid moiety or fits derivatives, when $R_2$ and $R_4$ represent a carboxy, carbamoyl or alkoxycarbonyl radical, are in the D,D L,L,D,D/L,L (racemic) or D,L (meso) form, and salts thereof possess immunostimulant activity.

21 Claims, No Drawings

TETRAPEPTIDES AND PENTAPEPTIDES, THEIR PREPARATION AND COMPOSITIONS CONTAINING THEM

The present invention relates to new tetrapeptides and pentapeptides which possess immunostimulant activity, to their preparation and to compositions containing them.

Bacterial walls, e.g. the walls of mycobacteria, essentially consist of a peptidoglycan, formed from N-acetylmuramic acid, to which peptides containing the sequence L-Ala-D-Glu-DAP are fixed: Ala represents alanine, Glu represents glutamine and DAP represents diaminopimelic acid. Furthermore, bacterial walls are very rich in lipids, some of which are free and can be extracted and others of which are bonded to the structure of the wall and comprise mycolic acids ($\alpha$-branched and $\beta$-hydroxylic giant fatty acids). The constituents of the cell wall together form a covalent structure composed of a peptidoglycan and of an arabinogalactan mycolate, which are bonded to one another by means of phosphodiester linkages. These bacterial walls possess most of the biological properties of whole cells when they are associated with a mineral or vegetable oil and administered after being suspended in physiological solution.

Peptides, coupled with N-acetylmuramic acid, which contain the sequence L-Ala-D-Glu or L-Ser-D-Glu (in which Ser represents serine) and which are effective as immunological adjuvants and as anti-infectious agents are described in British Patent Specifications Nos. 1496332 and 1496333 and in Belgian Patent Specifications Nos. 852,348 and 852,349.

Products which result from the coupling of a fatty acid with a heptapeptide saccharide isolated from a mycobacterium containing a "D" wax, and which can be represented by the following formula:

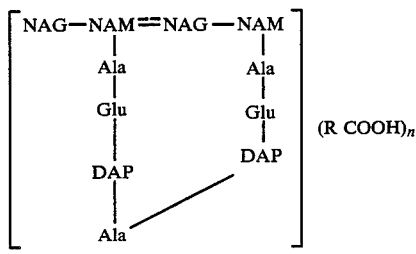

wherein, in particular, NAG represents N-acetylglucosamine, NAM represents N-acetylmuramic acid and R represents an alkyl radical containing 9 to 17 carbon atoms, are described in British Patent Specification No. 1,525,763. These products are immunological adjuvants for the production of antibodies and the potentiation of delayed hypersensitivity, which are capable of acting alone, i.e. it is not necessary to administer them in oily solution.

All these products are characterised by the presence of N-acetylmuramic acid, which, according to Kasumoto et al., Tetrahedron Letters, 49,4,899 (1978), is considered to be associated with the immunological activity.

It has now been found that certain tetrapeptides and pentapeptides possess remarkable adjuvant and immunostimulant properties, despite the absence of N-acetylmuramic acid. Furthermore, these compounds, which are well defined, can easily be obtained with the purity required for therapeutic use.

The present invention accordingly provides tetrapeptides and pentapeptides of the general formula:

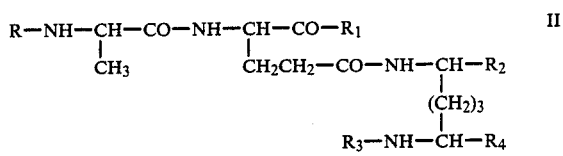

wherein R represents a hydrogen atom or a fatty acid residue, $R_1$ represents a hydroxy or amino radical or an alkoxy radical containing 1 to 4 carbon atoms, which is optionally substituted by a phenyl or nitrophenyl radical, one of the symbols $R_2$ and $R_4$ represents a hydrogen atom, a carboxy or carbamoyl radical, an alkoxycarbonyl radical in which the alkyl moiety, which contains 1 to 4 carbon atoms, is optionally substituted by a phenyl or nitrophenyl radical, or a N-carbonylglycine (—CO—NH—CH$_2$—COOH) or N—carbonyl-D-alanine[—CO—NH—CH(CH$_3$)—COOH] radical which is optionally esterified by an alkyl radical containing 1 to 4 carbon atoms (which is optionally substituted by a phenyl or nitrophenyl radical), and the other symbol represents a hydrogen atom, a carboxy or carbamoyl radical or an alkoxycarbonyl radical in which the alkyl moiety, which contains 1 to 4 carbon atoms, is optionally substituted by a phenyl or nitrophenyl radical, and $R_3$ represents a hydrogen atom, a fatty acid residue or a glycyl or D-alanyl moiety in which the amine group is optionally substituted by a fatty acid residue, it being understood that the symbols $R_2$ and $R_4$ cannot simultaneously represent a hydrogen atom, that one of the symbols $R_2$, $R_3$ and $R_4$ represents a glycyl or D-alanyl moiety or a radical containing a glycyl or D-alanyl moiety, that at least one of the symbols R and $R_3$ represents a fatty acid residue or a moiety containing a fatty acid residue and that the alanine moiety bonded to the glutamic acid moiety is in the L form, the glutamic acid moiety or its derivatives are in the D form, the lysine moiety or its derivatives, when one of the symbols $R_2$ and $R_4$ represents a hydrogen atom, are in the L form and the 2,6-diaminopimelic acid moiety or its derivatives, when $R_2$ and $R_4$ represent a carboxy, carbamoyl or alkoxycarbonyl radical, are in the D,D L,L D,D/L,L (racemic) or D,L (meso) form, and salts thereof.

By the term fatty acid residue as used in this specification and the accompanying claims is meant an alkanoyl radical containing 1 to 45 carbon atoms, which is optionally substituent by a hydroxyl, phenyl or cyclohexyl radical, an alkenoyl radical which contains 3 to 30 carbon atoms and may contain more than one double bond, or a mycolic acid residue, such as that encountered in the structure of the bacterial wall of mycobacteria, Nocardia or Corynebacteria.

It is to be understood that in this specification and the accompanying claims, alkyl radicals and alkyl moieties of alkoxy, alkoxycarbonyl and alkanoyl radicals and alkenyl moieties of alkenoyl radicals, may be straight- or branched-chain.

According to a feature of the present invention, the peptides of general formula II can be obtained in accordance with the methods generally used in peptide synthesis. The various reactions are carried out after the blocking, by means of suitable protecting groups, of the amino or carboxylic acid groups which must not participate in the reaction, and are followed, if appropriate, by the unblocking of these groups.

According to a feature of the present invention, the peptides of general formula II are prepared by reacting an aminoacid of the general formula:

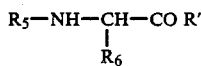

wherein $R_5$ represents a hydrogen atom, a fatty acid residue or an amino-protecting group, e.g. the benzyloxycarbonyl or t-butoxycarbonyl radical, $R_6$ represents a hydrogen atom or the methyl radical, the alanine moiety, when $R_6$ represents methyl, being in the D form, and R' represents a hydroxy radical or an alkoxy radical containing 1 to 4 carbon atoms, which is optionally substituted by a phenyl or nitrophenyl radical, with a tripeptide or tetrapeptide of the general formula:

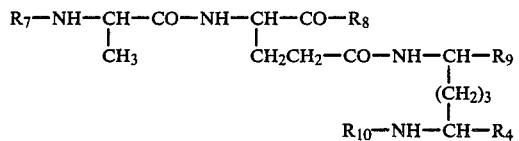

wherein $R_7$ represents a fatty acid residue or an amino-protecting group, e.g. the benzyloxycarbonyl or t-butoxycarbonyl radical, $R_8$ represents a hydroxy or amino radical or an alkoxy radical containing 1 to 4 carbon atoms, which is optionally substituted by a phenyl or nitrophenyl radical, one of the symbols $R_4$ and $R_9$ represents a hydrogen atom, a carboxy or carbamoyl radical, an alkoxycarbonyl radical in which the alkyl moiety contains 1 to 4 carbon atoms and is optionally substituted by a phenyl or nitrophenyl radical, or a N-carbonylglycine or N-carbonyl-D-alanine radical which is optionally esterified by an alkyl radical containing 1 to 4 carbon atoms, which is optionally substituted by a phenyl or nitrophenyl radical, and the other represents a hydrogen atom, a carboxy or carbamoyl radical or an alkoxycarbonyl radical in which the alkyl moiety contains 1 to 4 carbon atoms and is optionally substituted by a phenyl or nitrophenyl radical, it being understood that $R_4$ and $R_9$ cannot simultaneously represent a hydrogen atom, and $R_{10}$ represents a hydrogen atom, a fatty acid residue, an amino-protecting group, e.g. the benzyloxycarbonyl or t-butoxycarbonyl radical, or a glycyl or D-alanyl moiety in which the amine group is optionally substituted by a fatty acid residue or by an amino-protecting group, e.g. the benzyloxycarbonyl or t-butoxycarbonyl radical, it being understood that at least one of the radicals $R_7$ and $R_{10}$ represents or contains a fatty acid residue, that when $R_4$ and $R_9$ are as hereinbefore defined, $R_{10}$ represents a hydrogen atom, and that if one of the symbols $R_4$ and $R_9$ represents a carboxy radical, and the other represents a hydrogen atom, a carbamoyl radical or an alkoxycarbonyl radical in which the alkyl moiety contains 1 to 4 carbon atoms, which is optionally substituted by a phenyl or nitrophenyl radical, $R_{10}$ represents a fatty acid residue, an amino-protecting group or a glycyl or D-alanyl moiety in which the amine group is substituted by a fatty acid residue or by an amino-protecting group, this reaction being followed, if appropriate, if the radicals $R_5$, $R_7$ and/or $R_{10}$ represent or contain an amino-protecting group by replacement of the amino-protecting group by a hydrogen atom, the optional replacement of the radicals R' and $R_8$ (when they represent an alkoxy radical containing 1 to 4 carbon atoms, which is optionally substituted by a phenyl or nitrophenyl radical) by a hydroxy radical, and if the radicals $R_4$ and/or $R_9$ represent or contain an alkoxycarbonyl radical in which the alkyl moiety contains 1 to 4 carbon atoms, which is optionally substituted by a phenyl or nitrophenyl radical) the optional replacement of the alkoxycarbonyl radical by a carboxy radical.

More particularly, the peptides of general formula II wherein R, $R_1$ and $R_3$ are as hereinbefore defined and one of the symbols $R_2$ and $R_4$ represents a N-carbonylglycine or N-carbonyl-D-alanine radical are prepared by reacting an aminoacid of general formula III, wherein $R_6$ and R' are as hereinbefore defined and $R_5$ represents a hydrogen atom, i.e. an aminoacid of the general formula:

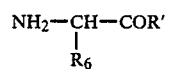

(wherein R' and $R_6$ are as hereinbefore defined) with a tripeptide or tetrapeptide of the general formula:

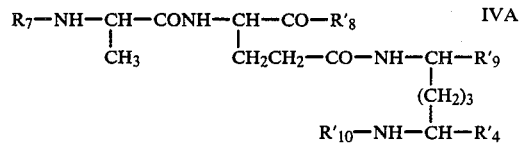

wherein $R_7$ is as hereinbefore defined, $R'_8$ represents an amino radical or an alkoxy radical containing 1 to 4 carbon atoms, which is optionally substituted by a phenyl or nitrophenyl radical, one of the symbols $R'_4$ and $R'_9$ represents a carboxy radical and the other represents a hydrogen atom, a carbamoyl radical or an alkoxycarbonyl radical in which the alkyl moiety contains 1 to 4 carbon atoms, which is optionally substituted by a phenyl or nitrophenyl radical, and $R'_{10}$ represents a fatty acid residue, an amino-protecting group or a glycyl or D-alanyl moiety in which the amine group is substituted by a fatty acid residue or by an amino-protecting group, it being understood that at least one of the symbols $R_7$ and $R'_{10}$ represents or contains a fatty acid residue, and then, if appropriate, if the radical $R_7$ or $R'_{10}$ represents or contains an amino-protecting group, replacing the amino-protecting group by a hydrogen atom, optionally replacing the radicals $R'_8$ and/or R', if they represent an alkoxy radical containing 1 to 4 carbon atoms (which is optionally substituted by a phenyl or nitrophenyl radical), by a hydroxy radical, and if the radical $R'_4$ or $R'_9$, represents or contains an alkoxycarbonyl radical in which the alkyl moiety contains 1 to 4 carbon atoms, which is optionally substituted by a phenyl or nitrophenyl radical, optionally replacing the alkoxycarbonyl radical by a carboxy radical.

In general, it is necessary to activate the free carboxylic acid group of the peptide of general formula IVA before it is reacted with the aminoacid of general formula IIIA. Preferably, the activated derivative of the peptide of general formula IVA is a mixed anhydride prepared in situ by reacting an alkyl halogenoformate, e.g. isobutyl chloroformate, with the peptide of general formula IVA. The reaction of the activated derivative of the peptide of general formula IVA with the aminoacid of general formula IIIA is generally carried out in an organic solvent, e.g. dioxan, tetrahydrofuran, chloroform, toluene or dimethylformamide, or in an aqueous-organic medium, in the presence of a base (an inorganic base, e.g., sodium hydroxide, or an organic base, e.g. triethylamine), at a temperature between $-10°$ and $+30°$ C.

The known methods used for the replacement, if appropriate, of the protecting groups represented by or contained in $R_7$, $R_{10}$ or $R'_{10}$ by a hydrogen atom, of the protecting groups $R_8$, $R'_8$ and $R'$ by hydroxy radicals and of alkoxycarbonyl radicals represented by or contained in $R_4$, $R'_4$, $R_9$ or $R'_9$ by a carboxy radical can be carried out in accordance with the known methods, depend on the nature of the protecting groups. It is particularly advantageous to choose the radicals $R_7$, $R_{10}$ or $R'_{10}$, $R_8$, $R'_8$, $R'$ and $R_4$, $R'_4$, $R_9$ or $R'_9$ so that the various replacements can be carried out in a single step. For example, $R_7$, $R_{10}$ or $R'_{10}$ may represent or contain a benzyloxycarbonyl radical and the symbols $R_8$, $R'_8$, $R'$ and $R_4$, $R'_4$, $R_9$ or $R'_9$ may represent or contain a benzyloxy or benzyloxycarbonyl radical, and, under these conditions, the replacement of these radicals by hydrogen atoms or by a hydroxy or carboxy radical, depending on the particular case, is carried out by hydrogenolysis, the reaction being carried out in a suitable organic solvent, e.g. acetic acid (if appropriate mixed with another organic solvent, e.g. methanol), or in an aqueous-organic solvent, in the presence of a catalyst, for example palladium, e.g. palladium-on-charcoal, at a temperature of the order of 20° C. and under a pressure of the order of 760 mm Hg. However, it may be necessary to remove one or more of these protecting groups without affecting the others. In this case, one of the amino-protecting groups can be, e.g. a t-butoxycarbonyl radical (which can be removed by said hydrolysis) and the other can be, e.g. a benzyloxycarbonyl radical (which can be removed by hydrogenolysis), and one of the protecting groups of the acid groups can be, e.g. a methyl or t-butyl radical (which can be removed by acid or base hydrolysis) and the other can be e.g. a benzyl radical (which can be removed by hydrogenolysis).

More particularly, the peptides of general formula II wherein R, $R_1$, $R_2$ and $R_4$ are as hereinbefore defined and $R_3$ represents a glycyl or D-alanyl moiety in which the amine group is optionally substituted by a fatty acid residue are prepared by reacting an aminoacid of general formula III, wherein $R_6$ is as hereinbefore defined, $R_5$ represents a fatty acid residue or an amino-protecting group and R' represents a hydroxy radical, i.e. an aminoacid of the general formula:

$$R'_5-NH-COOH \atop R_6 \qquad \text{IIIB}$$

wherein $R_6$ is as hereinbefore defined and $R'_5$ represents a fatty acid residue or an amino-protecting group, with a tripeptide or tetrapeptide of the general formula:

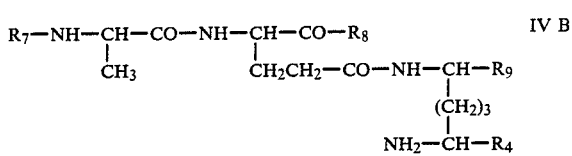

wherein $R_4$, $R_7$, $R_8$ and $R_9$ are as hereinbefore defined it being understood that at least one of the symbols $R'_5$ and $R_7$ represents a fatty acid residue, and then, if appropriate, replacing the radical $R'_5$ or $R_7$, if it represents an amino-protecting group, by a hydrogen atom, optionally replacing the radical $R_8$, if it represents an alkoxy radical containing 1 to 4 carbon atoms (which is optionally substituted by a phenyl or nitrophenyl radical), by a hydroxy radical, and if the radicals $R_4$ and/or $R_9$ represent or contain an alkoxycarbonyl radical in which the alkyl moiety contains 1 to 4 carbon atoms (which is optionally substituted by a phenyl or nitrophenyl radical), optionally replacing the alkoxycarbonyl radical by a carboxy radical.

In general, it is necessary to activate the carboxy acid group of the aminoacid of general formula IIIB before it is reacted with the peptide of general formula IVB. In general, the activated derivative of the aminoacid of general formula IIIB is a mixed anhydride prepared in situ by reacting an alkyl halogenoformate (such as isobutyl chloroformate) with the aminoacid of general formula IIIB. The reaction of the activated derivative of the aminoacid of general formula IIIB with the peptide of general formula IVB is carried out in an organic solvent, e.g. dioxan, tetrahydrofuran, chloroform, toluene or dimethylformamide, or in an aqueous-organic medium, in the presence of a base (an inorganic base, e.g. sodium hydroxide, or an organic base, e.g. triethylamine), at a temperature between $-10°$ and $+30°$ C.

If the acid of general formula IIIB is used, the condensation is generally carried out in the presence of a condensation agent, such as dicyclohexylcarbodiimide, the reaction being carried out in an organic solvent, e.g. methylene chloride or dimethylformamide, at a temperature between $-10°$ and $+30°$ C.

The replacement of the protecting radicals $R'_5$ or $R_7$ by a hydrogen atom and of the protecting radicals $R_8$ by a hydroxy radical and of an alkoxycarbonyl radical represented or contained by a $R_4$ and/or $R_9$ by a carboxy radical, depending on the particular case, can be carried out in accordance with the known methods, depending on the nature of these groups. It is particularly advantageous to carry out this replacement under the conditions given above.

According to a further feature of the present invention, the peptides of general formula II are prepared by reacting a dipeptide of the general formula:

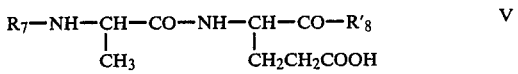

wherein $R_7$ and $R'_8$ are as hereinbefore defined, with a dipeptide or tripeptide of the general formula:

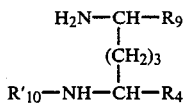   VI wherein $R_4$, $R_9$ and $R'_{10}$ are as hereinbefore defined, at least one of the symbols $R_4$, $R_9$ and $R'_{10}$ representing or containing a glycyl or D-alanyl moiety as hereinbefore defined, and at least one of the symbols $R_7$ and $R'_{10}$ representing or containing a fatty acid residue, and then, if appropriate, if the radical $R_7$ or $R'_{10}$ represents or contains an amino-protecting group, replacing the amino-protecting group by a hydrogen atom, and optionally replacing an alkoxy radical or an alkoxycarbonyl radical the alkyl moiety of which contains 1 to 4 carbon atoms, which is optionally substituted by a phenyl or nitrophenyl radical, represented or contained by a radical $R_4$, $R'_8$ or $R_9$ by a hydroxy or carboxy radical.

In general, it is necessary to activate the free acid group of the dipeptide of general formula V before it is reacted with the peptide of general formula VI. Preferably, the activated derivative of the dipeptide of general formula V is a mixed anhydride prepared in situ by reaction with an alkyl halogenoformate, e.g. isobutyl chloroformate. Under these conditions, the reaction of the dipeptide of general formula V with the peptide of general formula VI is carried out as indicated above for the reaction of an aminoacid of general formula III with a tripeptide of general formula IV.

The replacement, if appropriate, of the protecting radicals represented or contained by $R_7$ or $R'_{10}$ by a hydrogen atom and of the protecting radicals represented by $R_4$, $R'_8$ or $R_9$ by a hydroxy or carboxy radical is carried out in accordance with the known methods indicated above.

According to a further feature of the present invention, the peptides of general formula II are prepared by reacting a L-alanine derivative of the general formula:

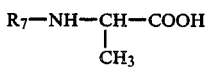   VII wherein $R_7$ is as hereinbefore defined, with a tripeptide or tetrapeptide of the general formula:

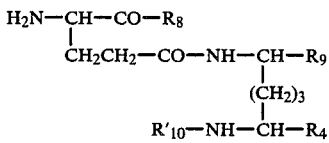   VIII wherein $R_4$, $R_8$, $R_9$ and $R'_{10}$ are as hereinbefore defined, at least one of the symbols $R_4$, $R_9$ and $R'_{10}$ representing or containing a glycyl or D-alanyl moiety as hereinbefore defined, and at least one of the symbols $R_7$ and $R'_{10}$ representing or containing a fatty acid residue, and then if appropriate, if the radical $R_7$ or $R'_{10}$ represents or contains an amino-protecting group replacing the amino-protecting group by a hydrogen atom and optionally replacing an alkoxy radical, or an alkoxycarbonyl radical the alkyl moiety of which contains 1 to 4 carbon atoms, which is optionally substituted by a phenyl or nitrophenyl radical, represented or contained by a radical $R_4$, $R_8$ or $R_9$ by a hydroxy or carboxy radical, under the conditions described above for the reaction of an aminoacid of general formula III with a tripeptide or tetrapeptide of general formula IV.

According to a further feature of the present invention, the peptides of general formula II are prepared by reacting an acid of the general formula:

   IX (wherein $R''$—CO— represents a fatty acid residue as hereinbefore defined) or an activated derivative thereof, with a tetrapeptide or pentapeptide of the general formula:

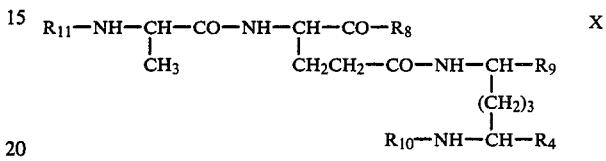   X wherein $R_4$, $R_8$, $R_9$ and $R_{10}$ are as hereinbefore defined and $R_{11}$ represents a hydrogen atom, a fatty acid residue or an amino-protecting group, it being understood that at least one of the symbols $R_4$, $R_9$ and $R_{10}$ represents or contains a glycyl or D-alanyl residue as hereinbefore defined, that at least one of the symbols $R_{10}$ and $R_{11}$ represents a hydrogen atom or, in the case of $R_{10}$, a glycyl or D-alanyl radical in which the amine group is free, and that if one of the radicals $R_{10}$ and $R_{11}$ represents or contains a fatty acid residue, that residue and the residue $R''$—CO— may be the same or different, and then, if appropriate, if the radical $R_{10}$ or $R_{11}$ represents or contains an amino-protecting group replacing the amino-protecting group by a hydrogen atom and optionally replacing an alkoxy radical or alkoxycarbonyl radical the alkyl moiety of which contains 1 to 4 carbon atoms, which is optionally substituted by a phenyl or nitrophenyl radical, represented or contained by a radical $R_4$, $R_8$ or $R_9$, by a hydroxy or carboxy radical.

If, in general formula X, the symbol $R_8$ represents an amino radical or an alkoxy radical containing 1 to 4 carbon atoms, which is optionally substituted by a phenyl or nitrophenyl radical, and one of the symbols $R_4$ or $R_9$ represents a N-carbonylglycine or N-carbonyl-D-alanine residue esterified by an alkyl radical containing 1 to 4 carbon atoms, which is optionally substituted by a phenyl or nitrophenyl radical, or an alkoxycarbonyl radical the alkyl moiety of which contains 1 to 4 carbon atoms, which is optionally substituted by a phenyl or nitrophenyl radical, and the other represents a hydrogen atom, a carbamoyl radical or an alkoxycarbonyl radical the alkyl moiety of which contains 1 to 4 carbon atoms, which is optionally substituted by a phenyl or nitrophenyl radical, the reaction of the acid of general formula IX with the peptide of general formula X is generally carried out in the presence of a condensation agent, e.g. dicyclohexylcarbodiimide, the reaction being carried out in an organic solvent, e.g. methylene chloride or dimethylformamide, at a temperature from $-10°$ to $+30°$ C.

If, in general formula X, one of the symbols $R_8$ represents or contains a hydroxy radical and $R_4$ and/or $R_9$ represents or contains a carboxy radical, it is necessary to activate the acid of general formula IX before it is reacted with the tetrapeptide or pentapeptide of general formula X. An acid halide or a mixed anhydride prepared in situ by reaction with an alkyl halogenoformate, e.g. isobutyl chloroformate, in the presence of a base, is particularly advantageously used as the activated derivative of the acid of general formula IX.

If the acid of general formula IX is used in the form of an acid halide, preferably the chloride, the reaction is carried out in an organic solvent, e.g. diethyl ether or methylene chloride, in the presence of a base (an inorganic base, e.g. sodium hydroxide, or an organic base, e.g. triethylamine), at a temperature from 0° to 30° C.

If the acid of general formula IX is used in the form of a mixed anhydride, the reaction is carried out in an organic solvent, e.g. dioxan, tetrahydrofuran, chloroform, toluene or dimethylformamide, or in an aqueous-organic medium, in the presence of a base (an inorganic base, e.g. as sodium hydroxide, or an organic base, e.g. triethylamine), at a temperature from $-10°$ to $+30°$ C.

The replacement, if appropriate, of the radicals $R_{10}$ and/or $R_{11}$ by a hydrogen atom and of alkoxy or alkoxycarbonyl radicals represented or contained by the radicals $R_4$, $R_8$ or $R_9$ by a hydroxy or carboxy radical is carried out in accordance with the known methods hereinbefore described.

To obtain a peptide of general formula II wherein R represents a fatty acid residue and $R_3$ represents the same fatty acid residue or a glycyl or D-alanyl residue in which the amine group is substituted by the same fatty acid residue, the acid of general formula IX is reacted with a peptide of general formula X wherein $R_{10}$ represents a hydrogen atom or a glycyl or D-alanyl residue and $R_{11}$ represents a hydrogen atom, or with a peptide of general formula X wherein $R_{10}$ represents or contains a fatty acid residue which is identical to the residue of the acid of general formula IX employed and $R_{11}$ represents a hydrogen atom, or alternatively with a peptide of general formula X wherein $R_{10}$ represents a hydrogen atom or a glycyl or D-alanyl residue and $R_{11}$ represents a fatty acid residue which is identical to the residue of the acid of general formula IX employed, the reaction being carried out under the conditions hereinbefore described.

To obtain a peptide of general formula II wherein the symbols R and $R_3$ represent or contain different fatty acid residues, it is necessary to condense an acid of general formula IX with a peptide of general formula X wherein $R_{10}$ represents or contains a fatty acid residue which is different from the residue of the acid of general formula IX employed, or an amino-protecting group, and $R_{11}$ represents a hydrogen atom, or alternatively with a peptide of general formula X wherein $R_{10}$ represents a hydrogen atom or a glycyl or D-alanyl residue and $R_{11}$ represents a fatty acid residue which is different from the residue of the acid of general formula IX employed, or an amino protecting group, and then, if necessary, after removal of the amino-protecting group, to react group, $R_8$ represents an amino radical or an alkoxy radical containing 1 to 4 carbon atoms, which is optionally substituted by a phenyl or nitrophenyl radical, and $R_{10}$ represents a fatty acid residue, an amino-protecting group or a glycyl or D-alanyl residue substituted by a fatty acid residue or by an amino-protecting group can be obtained by the reaction, under the conditions hereinbefore described, of a dipeptide of general formula V, wherein $R_7$ and $R'_8$ are as hereinbefore defined, with an aminoacid or a dipeptide of general formula VI, wherein $R'_{10}$ is as hereinbefore defined and one of the symbols $R_4$ and $R_9$ represents a carboxy radical or an alkoxycarbonyl radical the alkyl moiety of which contains 1 to 4 carbon atoms, which is optionally substituted by a phenyl or nitrophenyl radical, and the other represents a hydrogen atom, a carbamoyl radical or an alkoxycarbonyl radical the alkyl moiety of which contains 1 to 4 carbon atoms, which is optionally substituted by a phenyl or nitrophenyl radical, and then, if necessary replacing one of the radicals $R_4$ and $R_9$, if it represents an alkoxycarbonyl radical the alkyl moiety of which contains 1 to 4 carbon atoms (which is optionally substituted by a phenyl or nitrophenyl radical), by a carboxy radical, without affecting the rest of the molecule.

In particular, if $R'_8$, together with the carbonyl group to which it is bonded, forms an ester group and $R_4$ the amine group of the product obtained with another fatty acid of general formula IX, the reaction being carried out under the conditions hereinbefore described.

The aminoacid of general formula III wherein $R_6$ represents a hydrogen atom or a methyl radical, R' represents a hydroxy radical or an alkoxy radical containing 1 to 4 carbon atoms, which is optionally substituted by a phenyl or nitrophenyl radical, and $R_5$ represents a fatty acid residue can be obtained by reacting an acid of general formula IX, or an activated derivative thereof, with glycine or D-alanine in which the acid group is optionally protected in the form of an ester, this reaction being followed, if necessary, by the removal of the protecting group from the acid group.

Whether or not the acid group of the glycine or of the D-alanine is protected, the condensation is carried out under the conditions hereinbefore described for the reaction of the acid of general formula IX with the tetrapeptide or pentapeptide of general formula X.

The tripeptide or tetrapeptide of general formula IV wherein one of the symbols $R_4$ and $R_9$ represents a carboxy radical and the other represents a hydrogen atom, a carbamoyl radical or an alkoxycarbonyl radical the alkyl moiety of which contains 1 to 4 carbon atoms, which is optionally substituted by a phenyl or nitrophenyl radical, $R_7$ represents a fatty acid residue or an amino-protecting and $R_9$ represent an ester group, it may be necessary for the radicals $R_4$, $R'_8$ and $R_9$ to be different and to be chosen so that the replacement of one of the radicals $R_4$ and $R_9$ by a carboxy radical is carried out without affecting the radical $R'_8$ and the other radical $R_4$ or $R_9$. For example, one of the radicals $R_4$ and $R_9$ can represent a benzyloxycarbonyl radical, which can be removed by hydrogenolysis, and the radical $R'_8$ and the other radical $R_4$ or $R_9$ can represent a methoxy radical, which is not sensitive to hydrogenolysis.

The tripeptide or tetrapeptide of general formula IV wherein $R_7$ represents a fatty acid residue or an amino-protecting group, $R_8$ represents an amino radical or an alkoxy radical containing 1 to 4 carbon atoms, which is optionally substituted by a phenyl or nitrophenyl radical, one of the symbols $R_4$ and $R_9$ represents a hydrogen atom, a carboxy or carbamoyl radical or an alkoxycarbonyl radical the alkyl moiety of which contains 1 to 4 carbon atoms, which is optionally substituted by a phenyl or nitrophenyl radical, or a N-carbonylglycyl or N-carbonyl-D-alanyl radical which is optionally esterified by an alkyl radical containing 1 to 4 carbon atoms, which is optionally substituted by a phenyl or nitrophenyl radical, and the other represents a hydrogen atom, a carbamoyl radical or an alkoxycarbonyl radical the alkyl moiety of which contains 1 to 4 carbon atoms, which is optionally substituted by a phenyl or nitrophenyl radical, it being understood that $R_4$ and $R_9$ cannot simultaneously represent a hydrogen atom, and $R_{10}$ represents a hydrogen atom can be obtained by the reaction, under the conditions hereinbefore described, of a dipeptide of general formula V, wherein $R_7$ and $R'_8$ are as hereinbefore defined, with an aminoacid or a dipeptide of general formula VI, wherein $R_4$ and $R_9$ are as hereinbefore defined and $R'_{10}$ represents an amino-protecting group, and then replacing the amino-protecting group by a hydrogen atom, without affecting the rest of the molecule. In particular, the amino-protecting groups represented by $R_7$ and $R'_{10}$ must be different and must be chosen so that the replacement of the radical $R'_{10}$ by a hydrogen atom is carried out without affecting the radical $R_7$.

The dipeptide of general formula V can be obtained by reacting an activated derivate of L-alanine, of general formula VII, wherein $R_7$ represents a fatty acid residue or an amino-protecting group, with a D-glutamic acid derivative of the general formula:

$$\underset{\underset{CH_2CH_2-COOH}{|}}{H_2N-CH-CO-R'_8} \quad XI$$

wherein $R'_8$ is as hereinbefore described under the conditions hereinbefore described for the reaction of the aminoacid of general formula VII with the peptide of general formula VIII.

The dipeptide of general formula V wherein $R_7$ represents a fatty acid residue can also be obtained by reacting an acid of general formula IX with a dipeptide of the general formula:

$$\underset{\underset{CH_3}{|}}{H_2N-CH-CO-NH}-\underset{\underset{CH_2CH_2COOH}{|}}{CH-CO-R'_8} \quad XII$$

wherein $R'_8$ is as hereinbefore described, under the conditions hereinbefore described for the reaction of an acid of general formula IX with a tetrapeptide or pentapeptide of general formula X.

The aminoacid of general formula VI wherein $R_4$ represents a carbamoyl radical, $R_9$ represents a carboxy radical and $R'_{10}$ represents a benzyloxycarbonyl radical in the meso form, and more precisely the D-monoamide of benzyloxycarbonyl-(D)-meso-2,6-diaminopimelic acid, can be prepared in accordance with the process described in British Patent Specification No. 1496332.

The aminoacid or the dipeptide of general formula VI wherein $R_4$ represents a carbamoyl radical, $R_9$ represents a carboxy radical and $R'_{10}$ represents a fatty acid residue, an amino-protecting group or a glycyl or D-alanyl residue in which the amine group is substituted by a fatty acid residue or by an amino-protecting group, in the racemic, D,D or L,L form, can be prepared from the corresponding 2,6-diaminopimelic acid. For this purpose, the dibenzyl ester of 2,6-dibenzyloxycarbonylaminopimelic acid is prepared by known methods and is mono-saponified in accordance with the method described by A. Arendt et al., Roczniki Chemii Ann. Soc. Chim. Polonorum, 48, 1,305 (1974) [Chem. Abstr., 82, 31497 g (1975)], and the mono-saponified product is then converted, by reaction with ammoniacal methanol, into the monoamide of the general formula:

$$\underset{\underset{Z-NH-CH-CONH_2}{|}}{\underset{(CH_2)_3}{|}}{Z-NH-CH-COOH} \quad XIII$$

(wherein Z represents the benzyloxycarbonyl radical), which, after hydrogenolysis to convert the benzyloxycarbonyl radicals to hydrogen atoms in the presence of palladium-on-charcoal, yields 2,6-diaminopimelamic acid.

By reacting a copper salt, such as cupric bromide or basic copper carbonate, with the 2,6-diaminopimelamic acid, a complex is formed which can be represented by the formula:

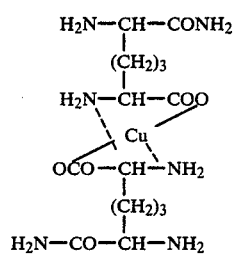

XIV wherein the amino radical in the α-position to the carbamoyl group can be acylated by reaction with an activated derivative of an acid of general formula IX or with an aminoacid of general formula III wherein $R_5$ represents a fatty acid residue or an amino-protecting group and R' represents a hydroxy radical, or protected by reaction with an alkyl halogenoformate or a benzyl halogenoformate. The complex formed in this way is dissociated by reaction with hydrogen sulphide in order to give the aminoacid or the dipeptide of general formula VI wherein $R_9$ represents a carboxy radical, $R_4$ represents a carbamoyl radical and $R'_{10}$ is as hereinbefore defined.

To obtain a product of general formula VI wherein $R_4$ represents a carboxy radical, $R_9$ represents a carbamoyl radical and $R'_{10}$ represents a fatty acid residue, an amino-protecting group or a glycyl or D-alanyl residue in which the amine group is substituted by a fatty acid residue or an amino-protecting group, the amine group in the α-position to the carbamoyl group in the product of general formula XIV is protected by reaction with an alkyl halogenoformate or a benzyl halogenoformate. The complex formed in this way is dissociated by reaction with hydrogen sulphide in order to give the aminoacid of general formula VI wherein $R_4$ represents a carbamoyl radical, $R_9$ represents a carboxy radical and $R'_{10}$ represents an amino-protecting group. The amino radical in the α-position to the carboxy group can be protected by a protecting group or acylated by reaction with an activated derivative of an acid of general formula IX or with an aminoacid of general formula III wherein $R_5$ represents a fatty acid residue or an amino-protecting group and R' represents a hydroxy radical. Replacement of the radical $R'_{10}$ by a hydrogen atom using methods which do not affect the rest of the molecule gives the product of general formula VI wherein $R_4$ represents a carboxy radical, $R_9$ represents a carbamoyl radical and $R'_{10}$ represents a fatty acid residue, an amino-protecting group or a glycyl or D-alanyl residue in which the amine group is substituted by a fatty acid residue or an amino-protecting group.

The aminoacid or the dipeptide of general formula VI wherein $R_4$ represents a carbamoyl radical, $R_9$ represents a carboxy radical and $R'_{10}$ represents a fatty acid residue, an amino-protecting group or a glycyl or D-alanyl residue in which the amine group is substituted by a fatty acid residue or by an amino-protecting group, in the meso form, in which the carbon atom carrying the radicals $R_4$ and $R'_{10}$ is in the D form, can be prepared by reacting an activated derivative of an acid of general formula IX or an aminoacid of general formula III wherein $R_5$ represents a fatty acid residue or an amino-protecting group, or an alkyl halogenoformate or a benzyl halogenoformate, with the copper complex of the (D)-monoamide of meso-2,6-diaminopimelic acid (obtained from the (D)-monoamide of benzyloxycarbonyl-(D)-meso-2,6-diaminopimelic acid by hydrogenolysis).

The aminoacid or the dipeptide of general formula VI wherein $R_4$ represents a carboxy radical, $R_9$ represents a carbamoyl radical and $R'_{10}$ represents a fatty acid residue, an amino-protecting group or a glycyl or D-alanyl residue in which the amine group is substituted by a fatty acid residue or by an amino-protecting group, in the meso form, in which the carbon atom carrying the radicals $R_4$ and $R'_{10}$ is in the L form, can be prepared by reacting a reagent for blocking the amine group, an activated derivative of an acid of general formula IX or an aminoacid of general formula III wherein $R_5$ represents a fatty acid residue or an amino-protecting group, with the (D)-monoamide of benzyloxycarbonyl-(D)-meso-2,6-diaminopimelic acid, this reaction being followed by the replacement of the benzyloxycarbonyl radical by a hydrogen atom, without affecting the rest of the molecule.

The aminoacid, dipeptide or tripeptide of general formula VI wherein $R_4$ represents a carbamoyl radical, $R_9$ represents an alkoxycarbonyl radical the alkyl moiety of which contains 1 to 4 carbon atoms, which is optionally substituted by a phenyl or nitrophenyl radical, or a N-carbonylglycine or N-carbonyl-D-alanine residue which is optionally esterified by an alkyl radical containing 1 to 4 carbon atoms, which is optionally substituted by a phenyl or nitrophenyl radical, and $R'_{10}$ represents a fatty acid residue, an amino-protecting group or a glycyl or D-alanyl residue in which the amine group is substituted by a fatty acid residue or by an amino-protecting group can be obtained by the reaction, by known methods, of an aminoacid of general formula III wherein $R_5$ represents a hydrogen atom, or of a corresponding aminoester, or of an aliphatic alcohol containing 1 to 4 carbon atoms, which is optionally substituted by a phenyl or nitrophenyl radical, or of a suitable derivative thereof, with an aminoacid or a dipeptide of the general formula:

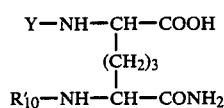
XV wherein $R'_{10}$ is as hereinbefore defined and Y represents an amino-protecting group, this reaction being followed by the replacement of the protecting group Y by a hydrogen atom and, if appropriate, the replacement of an ester group (carried by a glycyl or D-alanyl residue) by a hydroxy radical, without affecting the rest of the molecule. In particular, if $R'_{10}$ represents or contains an amino-protecting group, it is important to choose Y so that its replacement by a hydrogen atom is carried out without affecting the radical $R'_{10}$.

The dipeptide or tripeptide of general formula VI wherein $R_4$ represents a carbamoyl radical, $R_9$ represents an alkoxycarbonyl radical the alkyl moiety of which contains 1 to 4 carbon atoms and is optionally substituted by a phenyl or nitrophenyl radical, or an optionally esterified N-carbonylglycine or or N-carbonyl-D-alanine residue, and $R'_{10}$ represents a fatty acid residue or a glycyl or D-alanyl residue in which the amine group is substituted by a fatty acid residue or by an amino-protecting group can be obtained by the reaction, under the conditions hereinbefore described, of an activated derivative of an acid of general formula IX or an aminoacid of general formula III, wherein $R_5$ represents a fatty acid residue or an amino-protecting group and $R'$ represents a hydroxy radical, with a product of the general formula:

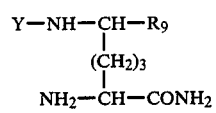
XVI wherein Y is as hereinbefore defined and $R^*_9$ represents an alkoxycarbonyl radical the alkyl moiety of which contains 1 to 4 carbon atoms and is optionally substituted by a phenyl or nitrophenyl radical or an optionally esterified N-carbonylglycine or N-carbonyl-D-alanine residue, under the conditions hereinbefore described, this reaction being followed by the replacement of the group Y by a hydrogen atom, without affecting the rest of the molecule.

The aminoacid, dipeptide or tripeptide of the general formula VI wherein $R_9$ represents a carbamoyl radical, $R_4$ represents an alkoxycarbonyl radical the alkyl moiety of which contains 1 to 4 carbon atoms and is optionally substituted by a phenyl or nitrophenyl radical or a N-carbonylglycine or N-carbonyl-D-alanine residue which is optionally esterified by an alkyl radical containing 1 to 4 carbon atoms, which is optionally substituted by a phenyl or nitrophenyl radical, and $R'_{10}$ represents a fatty acid residue, an amino-protecting group or a glycyl or D-alanyl residue in which the amine group is substituted by a fatty acid residue or by an amino-protecting group can be obtained by the reaction, by known methods, of an aminoacid of general formula III, wherein $R_5$ represents a hydrogen atom and $R'$ represents a hydroxy radical, or of a corresponding aminoester, or of an aliphatic alcohol containing 1 to 4 carbon atoms, which is optionally substituted by a phenyl or nitrophenyl radical, or of a derivative thereof, with an aminoacid or a dipeptide of the general formula:

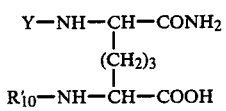
XVA wherein $R'_{10}$ and Y are as hereinbefore defined, this reaction being followed by the replacement of the protecting group Y by a hydrogen atom and, if appropriate, the replacement of an ester group (carried by a glycyl or D-alanyl residue) by a hydroxy radical, without affecting the rest of the molecule. In particular, if R′$_{10}$ represents or contains an amino-protecting group, it is important to choose Y so that its replacement by a hydrogen atom is carried out without affecting the radical R′$_{10}$.

If the optionally esterified aminoacid of general formula III is reacted with the aminoacid of general formula XVA, the reaction is carried out by known methods to create a peptide linkage without affecting the rest of the molecule. If an aliphatic alcohol containing 1 to 4 carbon atoms, which is optionally substituted by a phenyl or nitrophenyl radical, is reacted with a compound of general formula XV or XVA, the reaction is carried out under mild esterification conditions so as not to affect the protective groups Y and R′$_{10}$, and is carried out more particularly in accordance with the method of V. Bocchi, Synthesis, page 961 (1979).

The dipeptide or tripeptide of general formula VI wherein R$_9$ represents a carbamoyl radical, R$_4$ represents an alkoxycarbonyl radical the alkyl moiety of which contains 1 to 4 carbon atoms and is optionally substituted by a phenyl or nitrophenyl radical or an optionally esterified N-carbonylglycine or N-carbonyl-D-alanine residue and R′$_{10}$ represents a fatty acid residue or a glycyl or D-alanyl residue in which the amine group is substituted by a fatty acid residue or by an amino-protecting group can be obtained by the reaction, under the conditions hereinbefore described, of an activated derivative of an acid of general formula IX or an aminoacid of general formula III, wherein R$_5$ represents a fatty acid residue or an amino-protecting group and R′ represents a hydroxy radical, with an aminoacid or a dipeptide of the general formula:

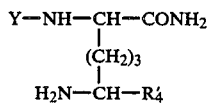

XVIA wherein Y is an hereinbefore defined and R*$_4$ represents an alkoxycarbonyl radical the alkyl moiety of which contains 1 to 4 carbon atoms and is optionally substituted by a phenyl or nitrophenyl radical or an optionally esterified N-carbonylglycine or N-carbonyl-D-alanine residue, this reaction being followed by the replacement of the group Y by a hydrogen atom, without affecting the rest of the molecule.

The products of general formulae XVI and XVIA can be obtained in accordance with known methods employed in peptide chemistry for the introduction of an amino-protecting group into an aminoacid or a dipeptide of general formula VI wherein one of the radicals R$_4$ and R$_9$ represents a carbamoyl radical and the other represents an alkoxycarbonyl radical in which the alkyl moiety contains 1 to 4 carbon atoms and is optionally substituted by a phenyl or nitrophenyl radical, or an optionally esterified N-carbonylglycine or N-carbonyl-D-alanine residue, and R′$_{10}$ represents an amino-protecting group, these methods being followed by the replacement of the protecting group R′$_{10}$ by a hydrogen atom, without affecting the rest of the molecule. In particular, the amino-protecting groups in 2,6-diaminopimelamic acid will be different and will be chosen so that the replacement of R′$_{10}$ does not cause the replacement of Y.

The dipeptide or tripeptide of general formula VI wherein one of the radicals R$_4$ and R$_9$ represents a hydrogen atom and the other represents a glycyl or D-alanyl residue and R′$_{10}$ represents a fatty acid residue or a glycyl or D-alanyl residue in which the amine group is substituted by a fatty acid residue or by an amino-protecting group can be obtained from L-lysine by applying the methods used for the preparation of the dipeptide or tripeptide of general formula VI wherein R$_9$ represents a carbamoyl radical and R$_4$ and R′$_{10}$ have the corresponding definitions.

The aminoacid of general formula VII wherein R$_7$ represents a fatty acid residue can be obtained by reacting an acid of general formula IX, or an activated derivative thereof, with L-alanine in which the acid group is optionally protected in the form of an ester, this reaction being followed, if appropriate, by the replacement of the ester group by a carboxy group, the reaction being carried out under the conditions indicated above for the reaction of the acid of general formula IX with the tetrapeptide or pentapeptide of general formula X.

The tripeptide or tetrapeptide of general formula VIII can be obtained by the reaction, under conditions hereinbefore described, of a D-glutamic acid derivative of general formula XI, wherein the amine group is protected and wherein R′$_8$ represents an amino radical or an alkoxy radical containing 1 to 4 carbon atoms, which is optionally substituted by a phenyl or nitrophenyl radical, with a dipeptide or tripeptide of general formula VI wherein R$_4$, R$_9$ and R′$_{10}$ are as hereinbefore defined, (at least one of the symbols R$_4$, R$_9$ and R′$_{10}$ representing a glycyl or D-alanyl radical as hereinbefore defined), this reaction being followed, if appropriate, by the optional replacement of an alkoxy radical containing 1 to 4 carbon atoms, which is optionally substituted by a phenyl or nitrophenyl radical represented by a radical R$_4$, R′$_8$ or R$_9$ by a hydroxy or carboxy radical, without affecting the rest of the molecule. However, if R′$_8$, together with the carbonyl group to which it is bonded, forms an ester group and R$_4$ and/or R$_9$ represent an ester group, it may be necessary for the radicals R′$_8$ and R$_4$ and/or R$_9$ to be different and to be chosen so that the replacement of one of the radicals R$_4$ or R$_9$ by a carboxy radical is carried out without affecting the radical R′$_8$ and the other radical R$_4$ or R$_9$. For example, one of the radicals R$_4$ or R$_9$ can represent a benzyloxycarbonyl radical, which can be removed by hydrogenolysis, and the radical R′$_8$ can represent an alkoxy radical and the other radical R$_4$ or R$_9$ can represent an alkoxycarbonyl radical, which latter radicals are not sensitive to hydrogenolysis.

The tetrapeptide or pentapeptide of general formula X can be obtained, under the conditions hereinbefore described, by the reaction of an activated derivative of L-alanine, of general formula VII, wherein R$_7$ represents a fatty acid residue or an amino-protecting group, with a tripeptide or tetrapeptide of general formula VIII wherein R$_8$ represents a hydroxy or amino radical or an alkoxy radical containing 1 to 4 carbon atoms, which is optionally substituted by a phenyl or nitrophenyl radical, one of the symbols R$_4$ and R$_9$ represents a hydrogen atom, a carboxy or carbamoyl radical, an alkoxycarbonyl radical the alkyl moiety of which contains 1 to 4 carbon atoms, and is optionally substituted by a phenyl or nitrophenyl radical, or a N-carbonylglycyl or N-carbonyl-D-alanyl residue which is optionally esterified by an alkyl radical containing 1 to 4 carbon atoms, which is optionally substituted by a phenyl or nitrophenyl radical, and the other represents a hydrogen atom, a carboxy or carbamoyl radical or an alkoxycarbonyl radical in which the alkyl part contains 1 to 4 carbon atoms and is optionally substituted by a phenyl or nitrophenyl radical, it being understood that $R_4$ and $R_9$ cannot simultaneously represent a hydrogen atom, and $R'_{10}$ represents fatty acid residue, an amino-protecting group or a glycyl or D-alanyl residue in which the amine group is substituted by a fatty acid residue or by an amino-protecting group, it being understood that at least one of the radicals $R_4$, $R_9$ and $R'_{10}$ represents a glycyl or D-alanyl residue as defined above, and that one of the radicals $R_7$ and $R'_{10}$ represents or contains an amino-protecting group, this reaction being followed, if the radicals $R_7$ and/or $R'_{10}$ represent or contain an amino-protecting group, by replacement of the amino-protecting group by a hydrogen atom, and, if appropriate, the optional replacement of an alkoxy radical or alkoxycarbonyl radical the alkyl moiety of which contains 1 to 4 carbon atoms, which is optionally substituted by a phenyl or nitrophenyl radical represented or contained by a radical $R_4$, $R_8$ or $R_9$ by a hydroxy or carboxy radical, without affecting the rest of the molecule. If the symbols $R_7$ and $R'_{10}$ represent or contain amino-protecting groups it is possible to choose different protecting groups so that the replacement of one of these groups is carried out without affecting the other.

If $R_8$, $R_4$ and $R_9$ form an ester group, it is possible for the radicals $R_8$, $R_4$ and $R_9$ to be different and to be chosen so that the replacement of one of the radicals $R_4$ and $R_9$ by a carboxy radical is carried out without affecting the radical $R_8$ and the other radical $R_4$ or $R_9$. For example, one of the radicals $R_4$ and $R_9$ can represent a benzyloxycarbonyl radical, which can be removed by hydrogenolysis, and the radical $R_8$ can represent a methoxy radical and the other radical $R_4$ or $R_9$ can represent an alkoxycarbonyl radical (such a radical is not sensitive to hydrogenolysis).

The tetrapeptide or pentapeptide of general formula X can be obtained by the reaction, under conditions hereinbefore described, of a dipeptide of general formula V with the dipeptide or tripeptide of general formula VI, under the conditions described above for preparing the tripeptide or tetrapeptide of general formula IV, this reaction being followed by the removal of the protecting groups $R_7$ and/or $R'_{10}$ under the conditions described above.

The present invention also relates to a process for the preparation of the peptides of general formula II by means of the Merrifield peptide synthesis in the solid phase. This process comprises fixing, to a suitable support, a dipeptide or tripeptide of the general formula:

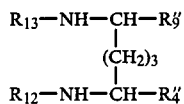

XVII wherein one of the symbols $R''_4$ and $R''_9$ represents a carboxy, N-carbonylglycine or N-carbonyl-D-alanine radical and the other represents a hydrogen atom, a carbamoyl radical or an alkoxycarbonyl radical in which the alkyl moiety contains 1 to 4 carbon atoms and is optionally substituted by a phenyl or nitrophenyl radical, $R_{12}$ represents a fatty acid residue, an amino-protecting group or a glycyl or D-alanyl radical in which the amine group is substituted by a fatty acid residue or an amino-protecting group, and $R_{13}$ represents an amino-protecting group, it being understood that if $R_{12}$ and $R_{13}$ each represent or contain an amino-protecting group, these protecting groups are different, and, after unblocking the amine group protected by $R_{13}$, reacting with the peptide fixed to the support:

(i) D-glutamic acid in which the amine and α-carboxyl groups are suitably protected, i.e. the product of the general formula:

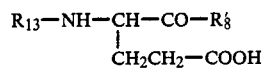

XVIII wherein $R'_8$ and $R_{13}$ are as hereinbefore defined, and, after unblocking the amine group protected by the radical $R_{13}$, reacting the product obtained with either:

(a) a L-alanine derivative of the general formula:

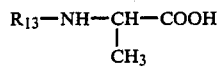

XIX wherein $R_{13}$ is as hereinbefore defined, and after unblocking the amine groups protected by $R_{13}$ and/or $R_{12}$, optionally reacting the product obtained with a fatty acid of general formula IX, to convert the amine group to a group $R''$—CO—NH— wherein $R''$ is as hereinbefore defined, or (b) a L-alanine derivative of the general formula:

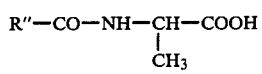

XX wherein $R''$ is as hereinbefore defined, or (ii) a dipeptide of the general formula:

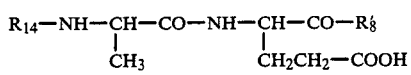

XXI wherein $R'_8$ is as hereinbefore defined and $R_{14}$ represents a fatty acid residue or an amino-protecting group, it being understood that if $R_{14}$ represents an amino-protecting group, the said protecting group can be different from the protecting group $R_{12}$ of the peptide of general formula XVII, and that the acid of general formula IX is then optionally reacted with the product obtained, if appropriate, after unblocking the amine groups protected by the radicals $R_{14}$ and/or $R_{12}$, and then separating the resulting product from its support and, if necessary, removing the protecting groups from the amine and carboxy groups.

A variant of this process comprises fixing, to a suitable support, a peptide of the general formula:

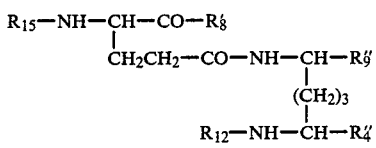

XXII wherein $R''_4$, $R'_8$, $R''_9$ and $R_{12}$ are as hereinbefore defined and $R_{15}$ represents an amino-protecting group, it being understood that if $R_{12}$ and $R_{15}$ each represent or contain an amino-protecting group, these protecting groups are different, and, after unblocking the amine group protected by $R_{15}$, reacting with the peptide fixed to the support:

either a L-alanine derivative of the general formula XIX, and, after unblocking the amine groups protected by $R_{13}$ and/or $R_{12}$, optionally reacting the product obtained with a fatty acid of general formula IX, to convert the amine group to a group R''—CO—NH— in which R'' is as hereinbefore defined, or a L-alanine derivative of general formula XX, and then separating the resulting product from its support and, if necessary, removing the protecting groups from the amine and carboxyl groups.

Another variant of this process comprises fixing, to a suitable support, a peptide of the general formula:

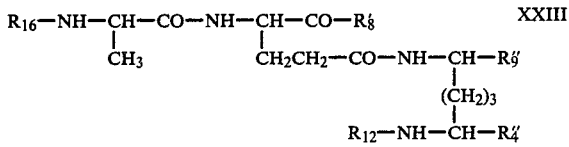

XXIII wherein $R''_4$, $R'_8$, $R''_9$ and $R_{12}$ are as hereinbefore defined and $R_{16}$ represents an amino-protecting group, it being understood that if $R_{12}$ and $R_{16}$ each represent or contain an amino-protecting group, these protecting groups can be different, and, after unblocking the amine groups protected by $R_{16}$ and/or $R_{12}$, optionally reacting the product obtained with a fatty acid of general formula IX, to convert the amine group to a group R''—CO—NH— in which R'' is as hereinbefore defined, and then separating the resulting product from its support and, if necessary, removing the protecting groups from the amine and carboxy groups.

The Merrifield peptide synthesis can also be carried out by fixing, to a suitable support, a product of general formula XVIII or XXI, in which formulae $R'_8$ represents a hydroxy radical, the symbols $R_{13}$ and $R_{14}$ are as hereinbefore defined as above and the γ-carboxyl radical is protected, and, after unblocking the protecting group and subsequently activating the acid group, reacting the dipeptide or tripeptide of the general formula XVII, in which the amine and carboxy groups are suitably protected, and optionally reacting the product obtained with an acid of general formula IX, if necessary after removal of amino-protecting groups.

If, in general formula II, one of the symbols $R_2$ and $R_4$ represents a N-carbonylglycine or N-carbonyl-D-alanine radical and the other represents a hydrogen atom, a carboxy or carbamoyl radical or an alkoxycarbonyl radical in which the alkyl moiety contains 1 to 4 carbon atoms and is optionally substituted by a phenyl or nitrophenyl radical, it is possible to fix, to a suitable support, gylcine or D-alanine in which the amine group is protected, and, after unblocking the amine group, to react, with the glycine or D-alanine fixed to the support, an aminoacid or a peptide of the general formula:

XXIV wherein $R'_4$, $R'_9$ and $R_{12}$ are as hereinbefore defined and $R_{17}$ represents an amino-protecting group or a D-aminoacid residue of the general formula:

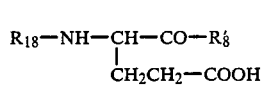

XXV wherein $R'_8$ is as hereinbefore defined and $R_{18}$ represents an amino-protecting group or a L-aminoacid residue of the general formula:

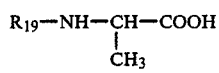

XXVI wherein $R_{19}$ represents an amino-protecting group or a fatty acid residue as hereinbefore defined, it being understood that if $R_{17}$, $R_{18}$ or $R_{19}$ represent an amino-protecting group, this protecting group is different from an amino-protecting group represented or contained by $R_{12}$, it being possible, however, for $R_{12}$ to be identical to $R_{19}$, and: if $R_{17}$ represents an amino-protecting group to remove this protecting group and to react with the product obtained:

either a D-glutamic acid derivative of general formula XXV wherein $R_{18}$ represents an amino-protecting group, and, after removing $R_{18}$, to react with the product obtained a L-alanine derivative of general formula XXVI wherein $R_{19}$ is as hereinbefore defined, and, if $R_{19}$ and/or $R_{12}$ represents an amino-protecting group, to remove the radicals $R_{19}$ and/or $R_{12}$ and then, optionally, to react the product obtained with an acid of general formula IX, or a D-glutamic acid derivative of general formula XXV wherein $R_{18}$ represents a L-aminoacid residue of general formula XXVI, in which $R_{19}$ is as hereinbefore defined, and, if $R_{19}$ and/or $R_{12}$ represent or contain an amino-protecting group, to remove the amino-protecting group and then react the product obtained with a fatty acid of general formula IX, if $R_{17}$ represents an aminoacid residue of general formula XXV wherein $R_{18}$ represents an amino-protecting group, to remove this protecting group and then to react the product obtained with a L-alanine derivative of general formula XXVI wherein $R_{19}$ is as hereinbefore defined, and, if $R_{19}$ and/or $R_{12}$ represent or contain an amino-protecting group, to remove the radicals $R_{19}$ and/or $R_{12}$ and then to react the product obtained with a fatty acid of general formula IX, and if $R_{17}$ represents an aminoacid residue of general formula XXV wherein $R_{18}$ represents a L-aminoacid residue of general formula XXVI wherein $R_{19}$ represents an amino-protecting group, to remove the radicals $R_{19}$ and/or $R_{12}$ and then optionally to react the product obtained with a fatty acid of general formula IX.

If, in general formula II, $R_3$ represents a glycyl or D-alanyl radical in which the amine group is optionally substituted by a fatty acid residue, the introduction of such a radical can be carried out at any stage of the Merrifield synthesis. For example, it is possible to fix, to a suitable support, the product of general formula XVII wherein $R_{12}$ represents an amino-protecting group which is different from $R_{13}$, then to remove $R_{12}$ without affecting $R_{13}$ and to react with the product obtained a glycine or D-alanine derivative in which the amine group is substituted by an amino-protecting group or a fatty acid residue, and then, after removing $R_{13}$, to react with the product obtained a product of general formula XVIII or under the conditions described above. Alternatively it is possible to fix, to a suitable support, a product of general formula XVII wherein $R_{12}$ represents an amino-protecting group, and to react with the product fixed to the support a product of general formula XVIII or XXI under the conditioning described above, and then, after removing $R_{12}$, to react with the product obtained glycine or D-alanine in which the amine group is substituted by an amino-protecting group or a fatty acid residue.

Particularly suitable supports are chloromethylated or hydroxymethylated styrene/divinylbenzene copolymers. Preferably, a chloromethylated styrene/divinylbenzene copolymer (98/2 or 99/1) is used.

The peptides of general formula XVII, XVIII, XXI, XXII or XXIII are fixed to the support by known methods. When a chloromethylated support is used the reaction with the support is generally effected by reacting the peptide of general formula XVII, XVIII, XXI, XXII or XXIII in solution in an organic solvent, e.g. ethanol, and in the presence of an acid acceptor, e.g. triethylamine. It is particularly advantageous to heat the reaction mixture to a temperature close to the boiling point of the solvent.

The amino-protecting groups of the peptides of general formula XVII, XVIII, XXI, XXII or XXIII must be chosen so that their removal may be carried out without affecting the peptide-support bond. In particular, the radicals $R_{13}$, $R_{14}$, $R_{15}$ and $R_{16}$ must be different from the radical $R_{12}$ if the latter represents or contains an amino-protecting group, and must be such that their removal may be carried out without affecting the protecting group $R_{12}$ and without affecting the peptide-support bond.

In general, the ester groups represented by $R'_4$, $R''_4$, $R'_8$ $R'_9$ or $R''_9$ are chosen so that, during the breaking of the peptide-support bond, the radicals $R'_4$, $R''_4$, $R'_8$, $R'_9$ or $R''_9$ can either be retained or be converted into carboxy or carbamoyl radicals, depending on whether the said bond is broken by acid hydrolysis, alcoholysis or ammonolysis.

More particularly, the peptide-support bond, which is generally of the benzyl type, is broken by treatment with a mixture of hydrogen bromide and trifluoroacetic acid, an acid group being regenerated.

If necessary, the peptides of general formula II can be purified by physical methods (e.g. crystallisation or chromatography) or chemical methods (e.g. the formation of a salt, crystallisation of the salt and then decomposition).

The products according to the invention can be converted by known methods into addition salts with acids or into metal salts or into addition salts with organic bases, depending on the nature of the substituents.

The addition salts with acids can be obtained by reacting the compounds of general formula II with an acid in a suitable solvent. In general, the product is solubilised in water by adding the theoretical amount of acid and the resulting solution is then lyophilised.

The metal salts or the addition salts with organic bases can be obtained by reacting the compounds of general formula II with a base in a suitable solvent. In general, the product is solubilised in water by adding the theoretical amount of base and the resulting solution is then lyophilised.

Preferably the salts of the compounds of general formula II are non-toxic salts, i.e. salts the cations, or in the case of acid addition salts, the anions, of which are relatively innocuous to the animal organism in therapeutic doses of the salts so that the beneficial physiological properties inherent in the compounds of general formula II are not vitiated by side effects ascribable to the cations or anions.

Suitable acid addition salts are, for example, the hydrochlorides, sulphates, nitrates, phosphates, acetates, propionates, succinates, benzoates, fumarates, maleates, theophylline-acetates, salicylates, phenolphthalinates and methylene-bis-$\beta$-hydroxynaphthoates.

The new compounds according to the present invention are useful as vaccine adjuvants and immunostimulants; they increase hypersensitivity reactions and/or the production of circulating antibodies against antigens with which they are administered, and they stimulate, in a non-specific manner, defence reactions against certain infections (e.g. the infection caused in mice by the intracellular bacterium Listeria monocytogenes).

In vitro, the compounds of general formula II are active at molar concentrations which are generally from $10^{-3}$ to $10^{-8}$, in particular in the following tests:

stimulating the synthesis of DNA (mitogenetic power), in accordance with the technique of G. Marchal, Ann. Immunol. (Inst. Pasteur), 125 C, 519 (1974), stimulating the allogenic reaction (histo-incompatibility reaction) in accordance with the technique of R. W. Dutton, J. exp. Med., 122, 759 (1966), and A. B. Peck and F. H. Bach, J. Immunol. Methods, 3, 147 (1973), stimulating the production of antibodies, in accordance with the technique of P. H. Klesius, Proc. Soc. exp. Biol. Med. (N.Y.), 135, 155 (1970), and H. van Dijk and N. Bloksma, J. Immunol. Methods, 14, 325 (1977), increasing the number of phagocytic macrophages, in accordance with the technique of J. Michl et al., J. exp. Med., 144, 1,465 (1976), and stimulating the acid phosphatase and N-acetylglucosamidinase activity (lysosome enzymes of macrophages) in the absence of an increase in the lactate dehydrogenase, in accordance with the technique of P. Davies et al., J. exp. Med., 139, 1,262 (1974).

In vivo, in mice, at doses of between 1 and 30 mg/kg, they increase the delayed hypersensitivity and the production of antibodies, in particular in accordance with the technique of T. E. Miller et al., J. Nath. Cancer Inst., 51, 1,669 (1973).

In guinea-pigs, they increase the hypersensitivity reaction and the production of antibodies against bovine gamma-globulin coupled with the hapten dinitrophenol, in accordance with the technique of F. Floc'h et al., Immunol. Communic., 7, 41 (1978).

In mice, they stimulate the defence reactions against the infection caused in mice by Listeria monocytogenes, at doses of between 1 and 100 mg/kg, in accordance with the technique of R. M. Fauve and B. Hevin, C. R. Acad, Sci. (D), 285, 1,589 (1977).

In mice, they stimulate the ability of the reticuloendothelial system to take up colloidal carbon, in accordance with the technique of B. N. Halpern et al., Ann. Institut Pasteur, 80, 582 (1951).

In rabbits, at doses which are generally between 0.1 and 3 mg/kg, they stimulate the formation of serum antibodies against influenza virus, in accordance with the technique of G. H. Werner et al., Biomedicine, 22, 440 (1975).

The symbol R in formula II preferably represents an alkanoyl radical containing 3 to 22 carbon atoms optionally substituted by a cyclohexyl radical. Of very particular value are the peptides of general formula II wherein R represents an alkanoyl radical containing 8 to 16 carbon atoms, $R_1$ represents a hydroxy radical, $R_2$ represents a carboxy radical, an alkoxycarbonyl radical in which the alkyl moiety contains 1 to 4 carbon atoms, or a N-carbonylglycine or N-carbonyl-D-alanine residue, $R_4$ represents a hydrogen atom or a carbamoylradical and $R_3$ represents a hydrogen atom or a glycyl or D-alanyl residue.

The following Examples, illustrate the invention.

The new products of general formula II can form complexes with alkali metals or alkaline earth metals. Consequently, the results of elementary analysis can deviate substantially from the theoretical values. However the products are identified by their amino-acid content, by the C/N ratio and by their homogeneity in thin-layer chromatography on silica gel.

EXAMPLE 1

Isobutyl chloroformate (0.27 cc) is added to a solution, kept at −5° C., of N-t-butoxycarbonylglycine (363 mg) in tetrahydrofurane (40 cc) and triethylamine (0.29 cc). The mixture is stirred for 20 minutes at −5° C. and a solution, cooled to 5° C., of $N^2$-(N-lauroyl-L-alanyl-γ-D-glutamyl)-D,D/L,L-2,6-diaminopimelamic acid hydrochloride (1.26 g) in a mixture of water (14.5 cc) and 1N sodium hydroxide solution (6.2 cc) is then added. The reaction mixture is stirred for 20 hours at a temperature of the order of 20° C. The tetrahydrofurane is evaporated off by concentration under reduced pressure (20 mm Hg) at 40° C.; the concentrate is cooled to about 10° C., acidified to pH 2 by adding 1N hydrochloric acid and then extracted 4 times with ethyl acetate (400 cc in total). The combined organic phases are washed with water (20 cc), dried over magnesium sulphate and concentrated to dryness under reduced pressure (20 mm Hg) at 45° C. The residue thus obtained is triturated in ether (50 cc) until it has all been converted to powder. Filtration and drying under reduced pressure (20 mm Hg) yields a powder (1.11 g) to which a product (440 mg) prepared under the same conditions is added, and the mixture is chromatographed on neutral silica gel (0.0635–0.20 mm) (77 g) contained in a column of diameter 2.3 cm. Elution is carried out successively with ethyl acetate (120 cc), a mixture of ethyl acetate and methanol (9/1 by volume) (210 cc), a mixture of ethyl acetate and methanol (85/15 by volume) (120 cc), a mixture of ethyl acetate and methanol (8/2 by volume) (120 cc), a mixture of ethyl acetate and methanol (7/3 by volume) (90 cc), a mixture of ethyl acetate and methanol (6/4 by volume) (240 cc) and a mixture of ethyl acetate and methanol (1/1 by volume) (150 cc), 30 cc fractions being collected. Fractions 15 to 34 are combined and concentrated to dryness under reduced pressure (20 mm Hg) at 40° C. The resulting residue is triturated in ether (50 cc), filtered off and dried. $N^2$-[N-(N-lauroyl-L-alanyl)-γ-D-glutamyl]-$N^6$-(N-t-butoxycarbonylglycyl)-D,D/L,L-2,6-diaminopimelamic acid (1.12 g) is thus obtained.

Rf=0.65 [silica gel; n-butanol/pyridine/acetic acid/water (50/20/6/24 by volume)].

$N^2$-[N-(N-lauroyl-L-alanyl)-γ-D-glutamyl]-$N^6$-(N-t-butoxycarbonylglycyl)-D,D/L,L-2,6-diaminopimelamic acid (1.12 g) is dissolved in a 1.65N anhydrous solution of hydrogen chloride in acetic acid (5 cc). The resulting solution is stirred for 4 hours at a temperature of the order of 20° C. and the reaction medium is then added to anhydrous ether (100 cc). The resulting white precipitate is filtered off, washed with ether (20 cc) and dried under reduced pressure (20 mm Hg). This yields a white powder (1.05 g) which is chromatographed on a Sephadex G 15 column (diameter: 2 cm; height: 2 m). Elution is carried out with water, 14 cc fractions being collected. Fractions 26 to 29 are combined and lyophilised. $N^2$-[N-(N-lauroyl-L-alanyl)-γ-D-glutamyl]-$N^6$-glycyl-D,D/L,L-2,6-diaminopimelamic acid hydrchloride (0.5 g) is thus obtained.

Rf=0.29 [silica gel; n-butanol/pyridine/acetic acid/water (50/20/6/24 by volume)].

Analysis: calculated % C, 52.36; H, 8.03; N, 12.63; found C, 52.5; H, 7.0; N, 12.4.

After total hydrolysis, analysis on a Technicon autoanalyser shows the presence of the following aminoacids:
Ala 1.10 (theory=1)
Dap 1.01 (theory=1)
Glu 1.12 (theory=1)
Gly 1.00 (theory=1)

$N^2$-(N-Lauroyl-L-alanyl-γ-D-glutamyl)-D,D/L,L-2,6-diaminopimelamic acid can be prepared in the following manner:

$N^2$-[$O^1$-Benzyl-N-(N-lauroyl-L-alanyl)-γ-D-glutamyl]-$N^6$-benzyloxycarbonyl-D,D/L,L-2,6-diaminopimelamic acid (4.07 g) is dissolved in acetic acid (200 cc). Palladium-on-charcoal (containing 3% of palladium) (4 g) is added and a slow stream of hydrogen is passed through the mixture for 7 hours. After filtering and concentrating the filtrate to dryness under reduced pressure (20 mm Hg) at 60° C., the resulting hard foam is taken up 3 times in methylcyclohexane (45 cc in total) and the mixture is concentrated to dryness each time under reduced pressure (20 mm Hg) at 60° C. The powder thus obtained is dried under reduced pressure (0.3 mm Hg) at 50° C. $N^2$-(N-Lauroyl-L-alanyl-γ-D-glutamyl)-D,D/L,L-2,6-diaminopimelamic acid (2.76 g) is obtained.

Rf=0.49 (silica gel; acetic acid).

Analysis: calculated=C, 56.72%; H, 8.64%; N, 12.25%; found=C, 53.4%; H, 8.5%; N, 10.9%.

After total hydrolysis, analysis on a Technicon autoanalyser shows the presence of the following aminoacids:
Ala 1.00 (theory=1)
Dap 0.99 (theory=1)
Glu 1.05 (theory=1)

$N^2$-[$O^1$-Benzyl-N-(N-lauroyl-L-alanyl)-γ-D-glutamyl]-$N^6$-benzyloxycarbonyl-D,D/L,L-2,6-diaminopimelamic acid can be prepared in the following manner:

Isobutyl chloroformate (3.17 cc) is added to a solution, kept at about 10° C., of benzyl N-lauroyl-L-alanyl-α-D-glutamate (11.96 g) in a mixture of dioxane (490 cc) and triethylamine (3.43 cc). The solution is stirred for 20 minutes at about 10° C. and a solution of $N^6$-benzyloxycarbonyl-D,D/L,L-2,6-diaminopimelamic acid (8.87 g), of 88.8% strength (perchloric acid determination), in a mixture of water (219 cc) and 1N sodium hydroxide solution (24.4 cc) is then added. The reaction mixture is stirred for 2 hours at a temperature of the order of 10° C. and then for 15 hours at a temperature of the order of 20° C.; it is then filtered. Water (360 cc) is added to the filtrate, and the small amount of insoluble material formed is filtered off. The filtrate is acidified to pH 2 by adding 1N hydrochloric acid (49 cc). The precipitate formed is filtered off, washed 3 times with water (750 cc in total) and dried. This yields a white powder (16.3 g) which is chromatographed on neutral silica gel (0.0635–0.20 mm) (800 g) contained in a column of diameter 6 cm. To do this, the powder (16.3 g) is dissolved in methanol (800 cc), and Fontainebleau sand (160 g) is added to the resulting solution. The mixture is evaporated to dryness under reduced pressure (20 mm Hg) at 60° C. and the residue thus obtained is introduced onto the silica column. Elution is carried out successively with ethyl acetate (1 liter), a mixture of ethyl acetate and methanol (9/1 by volume) (4 liters), a mixture of ethyl acetate and methanol (85/15 by volume) (7 liters) and a mixture of ethyl acetate and methanol (1/1 by volume) (4 liters), 250 cc fractions being collected. Fractions 45 to 60 are combined and concentrated to dryness under reduced pressure (20 mm Hg) at 60° C. This yields $N^2$-[$O^1$-benzyl-N-(N-lauroyl-L-alanyl)-$\gamma$-D-glutamyl]-$N^6$-benzyloxycarbonyl-D,D/L,L-2,6-diaminopimelamic acid (9.4 g).

Rf=0.83 [silica gel; n-butanol/pyridine/acetic acid/water (50/20/6/24 by volume)].

Benzyl N-lauroyl-L-alanyl-$\alpha$-D-glutamate can be prepared in accordance with one of the following two methods:

(a) Lauroyl chloride (8 g) dissolved in ether (75 cc) is added, in the course of 37 minutes, to a solution of benzyl L-alanyl-$\alpha$-D-glutamate hydrochloride (12.75 g) in 1N sodium hydroxide solution (75 cc), and 1N sodium hydroxide solution (37.4 cc) is added simultaneously so as to keep the pH of the reaction mixture at between 8 and 9. The mixture is stirred for 1 hour 20 minutes. After decantation, the aqueous phase is acidified to pH 2 by adding 1N hydrochloric acid (60 cc) and extracted 3 times with ethyl acetate (300 cc in total). The combined organic extracts are washed with water (25 cc), dried over anhydrous sodium sulphate and concentrated to dryness under reduced pressure (20 mm Hg) at 45° C. This yields a white solid (7.4 g) which is chromatographed on neutral silica gel (80 g) contained in a column of diameter 2 cm. Elution is carried out successively with a mixture of ethyl acetate and methanol (8/2 by volume) (100 cc) and a mixture of ethyl acetate and methanol (1/1 by volume) (200 cc), 50 cc fractions being collected. Fraction 1 is concentrated to dryness under reduced pressure (20 mm Hg) at 45° C. This yields benzyl N-lauroyl-L-alanyl-$\alpha$-D-glutamate (2 g) which melts at 130° C. Fractions 2 to 4 are likewise concentrated to dryness and chromatographed on neutral silica gel (0.063-0.20 mm) (100 g) contained in a column of diameter 2 cm. Elution is carried out with acetone (250 cc), 25 cc fractions being collected. Fractions 1 and 2 are concentrated to dryness under reduced pressure (20 mm Hg) at 45° C. This yields benzyl N-lauroyl-L-alanyl-$\alpha$-D-glutamate (4.07 g) which melts at 130° C. and has the following characteristics:

Rf=0.9 [silica gel; n-butanol/pyridine/acetic acid/water (50/20/6/24 by volume)].

Analysis calculated % C, 66.10; H, 8.63; N, 5.71; found C, 66.3; H, 8.8; N, 5.6.

(b) Isobutyl chloroformate (31 cc) is added to a solution, kept at a temperature of the order of 10° C., of lauric acid (47.75 g) in dioxane (3 liters) and triethylamine (33.3 cc). The mixture is stirred for 20 minutes at 10° C. and a solution, cooled to 10° C., of benzyl L-alanyl-$\alpha$-D-glutamate hydrochloride (88.95 g) in a mixture of dioxane (1 liter), water (476 cc) and 1N sodium hydroxide solution (476 cc) is then added in the course of 10 minutes. The reaction mixture is stirred for 1 hour at 10° C. and then for 18 hours at a temperature of the order of 20° C.; it is then diluted by adding water (4 liters), acidified to pH 2 by adding 1N hydrochloric acid (about 475 cc) and kept for 2 hours at 0° C. The resulting precipitate is filtered off, washed successively with water (500 cc) and ether (500 cc) and then dried under reduced pressure (20 mm Hg) at 20° C. The product is suspended in ether (800 cc), the suspension is stirred for 1 hour and the product is filtered off and washed twice with ether (200 cc in total). After drying under reduced pressure (20 mm Hg) at 20° C., benzyl N-lauroyl-L-alanyl-$\alpha$-D-glutamate (71.79 g), which melts at 130° C., is obtained.

Rf=0.77 [silica gel; ethyl acetate/methanol (4/1 by volume)].

Benzyl L-alanyl-$\alpha$-D-glutamate hydrochloride can be prepared in the following manner:

Benzyl N-t-butoxycarbonyl-L-alanyl-$\alpha$-D-glutamate (97.16 g) is dissolved in a 1.7N anhydrous solution of hydrogen chloride in acetic acid (970 cc). The resulting solution is stirred for 2 hours, anhydrous ether (3.8 liters) is then added rapidly and the mixture is left to stand for 2 hours at 0° C. The oily precipitate which has formed is separated from the supernatant liquor by decantation and dissolved in acetone (500 cc); the solution thus obtained is concentrated to dryness under reduced pressure (20 mm Hg) at 50° C. This yields benzyl L-alanyl-$\alpha$-D-glutamate hydrochloride (88.9 g).

Benzyl N-t-butoxycarbonyl-L-alanyl-$\alpha$-D-glutamate can be prepared in accordance with the method of E. BRICAS et al., Biochemistry 9, 823 (1970).

$N^6$-Benzyloxycarbonyl-D,D/L,L-2,6-diaminopimelamic acid can be prepared in the following manner:

Cupric bromide (4.35 g) dissolved in water (44 cc) is added to a solution of D,D/L,L-2,6-diaminopimelamic acid dihydrochloride (9.7 g) in water (63 cc), brought to pH 10 by adding 1N sodium hydroxide solution (37 cc). The reaction mixture is stirred for 2 hours at about 20° C. A small amount of insoluble material is filtered off and the filtrate is then cooled to a temperature between −3° C. and 0° C. Sodium bicarbonate (9.2 g) is added and benzyl chloroformate (7.9 cc) is then added dropwise in the course of 30 minutes. The reaction mixture is stirred for 18 hours at a temperature of the order of 20° C. The blue precipitate formed is filtered off and washed with water (15 cc), twice with ethanol (30 cc in total) and with ether (15 cc). Drying under reduced pressure (20 mm Hg) at 50° C. yields the copper complex of $N^6$-benzyloxycarbonyl-D,D/L,L-2,6-diaminopimelamic acid (9.6 g) which is added to 1N hydrochloric acid (60 cc). The mixture is stirred for 1 hour at a temperature of the order of 20° C. An insoluble material is filtered off. Methanol (30 cc) is added to the filtrate and a stream of hydrogen sulphide is passed through the mixture for 1½ hours. The mixture is left to stand for 16 hours. The resulting black slurry is filtered and the solid is washed 4 times with water (160 cc in total). The combined filtrates are concentrated to a volume of 30 cc under reduced pressure (20 mm Hg) at 50° C., brought to pH 9 by adding triethylamine (7.5 cc), diluted by adding water (20 cc) and brought to pH 6 by adding 1N hydrochloric acid (5.5 cc). The white slurry thus obtained is kept at 0° C. for 2 hours. The product is filtered off, washed successively with water (20 cc) and ethanol (20 cc) and dried under reduced pressure. This yields $N^6$-benzyloxycarbonyl-D,D/L,L-2,6-diaminopimelamic acid (5.8 g) of 96% strength (perchloric acid determination).

D,D/L,L-2,6-Diaminopimelamic acid dihydrochloride can be prepared in the following manner:

D,D/L,L-2,6-Dibenzyloxycarbonylaminopimelamic acid (83 g) is dissolved in a mixture of methanol (1.6 liters) and concentrated hydrochloric acid (d=1.19) (14.6 cc). Palladium-on-charcoal (containing 3% of palladium) (83 g) is added and a stream of hydrogen is passed through the mixture for 10 hours. After filtering and concentrating the filtrate to dryness under reduced pressure (20 mm Hg) at 60° C., D,D/L,L-2,6-diaminopimelamic acid dihydrochloride (40.5 g) is obtained in the form of a hard foam.

D,D/L,L-2,6-Dibenzyloxycarbonylaminopimelamic acid can be prepared in the following manner:

The monobenzyl ester of D,D/L,L-2,6-dibenzyloxycarbonylaminopimelic acid (168 g) is dissolved in methanol (1.68 liters). This solution is cooled to about 0° C. and saturated with ammonia. As soon as it is saturated, it is transferred into three 1 liter autoclaves. After these autoclaves have been closed, they are kept for 40 hours at about 20° C. After degassing, the solution thus obtained is concentrated under reduced pressure (20 mm Hg) at 60° C. The residue is dissolved in water (2 liters) and the resulting solution is brought to pH 2 by adding 4N hydrochloric acid. A gummy precipitate is formed and this is isolated by decantation, triturated with ether (2 liters), filtered off and washed twice with ether (400 cc in total) and twice with water (400 cc in total). After drying, D,D/L,L-2,6-dibenzyloxycarbonylaminopimelamic acid (83.5 g) which melts at 145°–150° C., is obtained.

Rf=0.69 [silica gel; n-butanol/ethanol/water/concentrated ammonia (4/4/1/1 by volume)].

The monobenzyl ester of D,D/L,L-2,6-dibenzyloxycarbonylaminopimelic acid can be prepared in accordance with the method of A. ARENDT et al., Roczniki Chemii Ann. Soc. Chim. Polonorum 48, 1,305 (1974) [Chem. Abstr., 82, 31497 g (1975)].

EXAMPLE 2

Isobutyl chloroformate (0.42 cc) is added to a solution, kept at 0° C., of N-t-butoxycarbonylglycine (557 mg) in a mixture of tetrahydrofurane (60 cc) and triethylamine (0.45 cc). The mixture is stirred for 20 minutes at 0° C. and a solution, cooled to 0° C., of N-α-[N-(N-lauroyl-L-alanyl)-γ-D-glutamyl]-L-lysine (1.68 g) in a mixture of water (14 cc) and 1N sodium hydroxide solution (6.36 cc) is then added. The reaction mixture is stirred for 10 minutes at 0° C. and then for 18 hours at about 20° C. It is then concentrated to dryness under reduced pressure (20 mm Hg) at 40° C. The residue is taken up in water (60 cc) brought to pH 2 by adding 1N hydrochloric acid (7 cc). The aqueous phase thus obtained, which contains an oily precipitate, is extracted 4 times with ethyl acetate (200 cc in total). The combined organic phases are washed with water (25 cc) and dried over anhydrous magnesium sulphate. Concentration to dryness under reduced pressure (20 mm Hg) at 40° C. yields a product (2.9 g) which is chromatographed on a column of diameter 2 cm, containing neutral silica gel (60 g). Elution is carried out successively with ethyl acetate (150 cc), a mixture of ethyl acetate and methanol (95/5 by volume) (200 cc), a mixture of ethyl acetate and methanol (9/1 by volume) (50 cc) and a mixture of ethyl acetate and methanol (8/2 by volume) (300 cc), 50 cc fractions being collected. Fractions 9 to 15 are combined and concentrated to dryness under reduced pressure (20 mm Hg) at 40° C. N-α-[N-(N-Lauroyl-L-alanyl)-γ-D-glutamyl]-N-ε-(t-butoxycarbonylglycyl)-L-lysine (1.44 g) is thus obtained.

Rf=0.55 [silica gel; n-butanol/pyridine/acetic acid/water (50/20/6/24 by volume)].

N-α-[N-(N-Lauroyl-L-alanyl)-γ-D-glutamyl]-N-ε-(t-butoxycarbonylglycyl)-L-lysine (1.44 g) is dissolved in a 1.7N anhydrous solution of hydrogen chloride in acetic acid (22 cc). The resulting solution is stirred for 2 hours and anhydrous ether (220 cc) is then added. The resulting precipitate is filtered off, washed with anhydrous ether (20 cc) and dried under reduced pressure (0.15 mm Hg) at 20° C. This yields a white powder (1.31 g) which is dissolvd in water (5 cc) and chromatographed on Sephadex G 10 (column of diameter 2.5 cm and height 2 m). Elution is carried out with water (400 cc), 14 cc fractions being collected. Fractions 23 to 28 are combined and lyophilised. The lyophilisate is dissolved in water (50 cc) and 1N hydrochloric acid (1.5 cc) and again lyophilised. N-α-[N-(N-Lauroyl-L-alanyl)-γ-D-glutamyl]-N-ε-glycyl-L-lysine hydrochloride (710 mg) is thus obtained.

Rf=0.25 [silica gel; n-butanol/pyridine/acetic acid/water (50/20/6/24 by volume)].

Analysis: calculated % C, 54.05; H, 8.42; Cl, 5.70; N, 11.26; found C, 54.0; H, 7.9; Cl, 5.4; N, 11.2.

After total hydrolysis, analysis on a Technicon autoanalyser shows the presence of the following aminoacids:
Ala 0.99 (theory=1)
Glu 1.04 (theory=1)
Gly 1.00 (theory=1)
Lys 0.97 (theory=1)

N-α-[N-(N-Lauroyl-L-alanyl)-γ-D-glutamyl]-L-lysine can be prepared in accordance with one of the following methods:

(a) N-α-[O$^1$-Benzyl-N-(N-lauroyl-L-alanyl)-γ-D-glutamyl]-N-ε-benzyloxycarbonyl-L-lysine (1.77 g) is dissolved in methanol (177 cc). Palladium-on-charcoal (containing 3% of palladium) (1.77 g) is added and a slow stream of hydrogen is then passed through the mixture for 4 hours. After filtering and concentrating the filtrate to dryness, the residual oil is taken up in acetone (20 cc). This yields a white solid (1.06 g) which is recrystallised from a mixture of ethanol (12 cc) and acetone (24 cc). This yields N-α-[N-(N-lauroyl-L-alanyl)-γ-D-glutamyl]-L-lysine (0.9 g) which melts at 180°–186° C. (to give a paste).

Rf=0.29 [silica gel; n-butanol/pyridine/acetic acid/water (50/20/6/24 by volume)].

Analysis calculated % C, 59.07; H, 9.15; N, 10.60; found C, 58.4; H, 8.8; N, 10.0.

(b) Benzyl N-α-[O$^1$-benzyl-N-(N-lauroyl-L-alanyl)-γ-D-glutamyl]-N-ε-benzyloxycarbonyl-L-lysinate (2.65 g) is dissolved in acetic acid (265 cc). Palladium-on-charcoal (containing 3% of palladium) (2.65 g) is added and a slow stream of hydrogen is passed through the mixture for 3 hours. Filtering and concentrating the filtrate to dryness under reduced pressure (20 mm Hg) at 50° C. yields N-α-[N-(N-lauroyl-L-alanyl)-γ-D-glutamyl]-L-lysine (1.81 g) which is identical to the product obtained under (a).

N-α-[O$^1$-Benzyl-N-(N-lauroyl-L-alanyl)-γ-D-glutamyl]-N-ε-benzyloxycarbonyl-L-lysine can be prepared in the following manner:

Isobutyl chloroformate (1.88 cc) is added to a solution, kept at 10° C., of benzyl N-lauroyl-L-alanyl-α-D-glutamate (7.03 g) in a mixture of dioxane (280 cc) and triethylamine (2.0 cc). The mixture is stirred for 20 minutes at 10° C. and a solution of N-ε-benzyloxycarbonyl-L-lysine (4.04 g) in a mixture of dioxane (30 cc) and 1N sodium hydroxide solution (14.4 cc) is then added. The reaction mixture is stirred for 20 hours at about 18° C. The insoluble material formed is dissolved by adding water (280 cc). The resulting solution is stirred for a further 1 hour and then acidified to pH 3 by adding 1N hydrochloric acid (20 cc). The insoluble material formed is filtered off, washed with water (20 cc) and dried under reduced pressure (0.3 mm Hg) at 20° C. This yields a white solid (7.72 g) which is chromatographed on a column of diameter 3.5 cm, containing neutral silica gel (230 g). Elution is carried out successively with a mixture of acetone and cyclohexane (9/1 by volume) (700 cc), acetone (1.1 liters) and methanol (1.7 liters). 100 cc fractions being collected. Fractions 22 to 35 are combined and concentrated to dryness under reduced pressure (20 mm Hg) at 45° C. This yields N-α-[O$^1$-benzyl-N-(N-lauroyl-L-alanyl)-γ-D-glutamyl]-N-ε-benzyloxycarbonyl-L-lysine (5.97 g).

Rf=0.84 [silica gel; n-butanol/pyridine/acetic acid/water (50/20/6/24 by volume)].

N-ε-Benzyloxycarbonyl-L-lysine can be prepared in accordance with the method of A. Neuberger et al., Biochem. J., 37, 515 (1943).

Benzyl N-α-[O$^1$-benzyl-N-(N-lauroyl-L alanyl)-γ-D-glutamyl]-N-ε-benzyloxycarbonyl-L-lysinate can be prepared in the following manner:

Isobutyl chloroformate (0.65 cc) is added to a solution, kept at −10° C., of benzyl N-lauroyl-L-alanyl-α-D-glutamate (2.45 g) in a mixture of tetrahydrofurane (80 cc) and triethylamine (0.70 cc). The mixture is stirred for 20 minutes at −10° C. and a solution, cooled to −10° C., of benzyl N-ε-benzyloxycarbonyl-L-lysinate hydrochloride (2.24 g) in a mixture of tetrahydrofurane (40 cc) and triethylamine (0.77 cc) is then added. The reaction mixture is stirred for 2 hours at −10° C. and then for 2 days at about 20° C. The reaction mixture is then concentrated to dryness under reduced pressure (20 mm Hg) at 40° C. The resulting white solid is taken up in ethyl acetate (100 cc) at 40° C., triturated to a powder, filtered off, triturated again in 0.1N hydrochloric acid (50 cc), filtered off and dried under reduced pressure (0.3 mm Hg). This yields benzyl N-α-[O$^1$-benzyl-N-(N-lauroyl-L-alanyl)-γ-D-glutamyl]-N-ε-benzyloxycarbonyl-L-lysinate (2.69 g).

Rf=0.80 [silica gel; ethyl acetate/methanol (9/1 by volume)].

Benzyl N-ε-benzyloxycarbonyl-L-lysinate can be prepared in accordance with the method of T. Shiba et al., Bull. Chem. Soc. Japan, 33, 1,721 (1960).

EXAMPLE 3

Isobutyl chloroformate (0.48 cc) is added to a solution, kept at about −10° C., of benzyl N-lauroyl-L-alanyl-α-D-glutamate (1.82 g) in a mixture of tetrahydrofurane (90 cc) and triethylamine (0.52 cc). The mixture is stirred for 20 minutes at −10° C. and a solution, cooled to −10° C., of benzyl N-ε-(benzyloxycarbonylglycyl)-L-lysinate (1.74 g) in tetrahydrofurane (90 cc) is then added. The reaction mixture is stirred for 2 hours at a temperature between −10° C. and 0° C. and then for 18 hours at about 20° C. This yields a reaction mixture of gelatinous appearance, which is concentrated to dryness under reduced pressure (20 mm Hg) at 40° C. The residue is taken up in a mixture of ethyl acetate (50 cc) and water (50 cc), the mixture is stirred and the insoluble material is filtered off and washed successively twice with N/10 sodium hydroxide solution (50 cc in total) and with water (25 cc). After drying, the insoluble material is washed 4 times with ethyl acetate (100 cc in total) at 20° C. and then with ethyl acetate (25 cc) at 75° C. and finally dried. Benzyl N-α-[O$^1$-benzyl-N-(N-lauroyl-L-alanyl)-γ-D-glutamyl]-N-ε-(benzyloxycarbonylglycyl)-L-lysinate (1.51 g) is thus obtained.

The ethyl acetate phase obtained from washing (125 cc) is introduced onto a column of diameter 3 cm, containing neutral silica gel (150 g). Elution is carried out with ethyl acetate (835 cc), a mixture of ethyl acetate and acetic acid (95/5 by volume) (320 cc) and a mixture of ethyl acetate and acetic acid (90/10 by volume) (400 cc), 40 cc fractions being collected. Fractions 34 to 38 are combined and concentrated to dryness under reduced pressure (20 mm Hg) at 45° C. Benzyl N-α-[O$^1$-benzyl-N-(N-lauroyl-L-alanyl)-γ-D-glutamyl]-N-ε-(benzyloxycarbonylglycyl)-L-lysinate (0.42 g) is thus obtained.

Rf=0.84 [silica gel; ethyl acetate/methanol (8/2 by volume)].

Benzyl N-α-[O$^1$-benzyl-N-(N-lauroyl-L-alanyl)-γ-D-glutamyl]-N-ε-(benzyloxycarbonylglycyl)-L-lysinate (1.93 g) is dissolved in acetic acid (100 cc). Palladium-on-charcoal (containing 3% of palladium) (1.93 g) is added and a slow stream of hydrogen is passed through the mixture for 2 hours. After filtering and concentrating the filtrate to dryness under reduced pressure (20 mm Hg) at 50° C., the residual oil is triturated in ether (50 cc). This yields a precipitate which is filtered off and is dissolved in acetic acid (15 cc). This solution is filtered and ether (100 cc) is then added to the filtrate. After stirring for 30 minutes, the resulting precipitate is filtered off. After drying under reduced pressure (0.15 mm Hg) at 20° C., N-α-[N-(N-lauroyl-L-alanyl)-γ-D-glutamyl]-N-ε-glycyl-L-lysine (1.16 g), which melts at 140°–142° C. (to give a paste), is obtained.

Rf=0.31 [silica gel; n-butanol/pyridine/acetic acid/water (50/20/6/24 by volume)].

Analysis calculated % C, 57.41; H, 8.78; N, 11.96; found C, 55.3; H, 8.6; N, 11.2.

After total hydrolysis, analysis on a Technicon autoanalyser shows the presence of the following aminoacids:

Ala 1.00 (theory=1)
Glu 1.11 (theory=1)
Gly 1.00 (theory=1)
Lys 0.95 (theory=1)

Benzyl N-ε-(N-benzyloxycarbonylglycyl)-L-lysinate can be prepared in accordance with the method of M. KHOSLA et al., J. Sci. Ind. Res. (India), 21 B, 318 (1962).

EXAMPLE 4

Isobutyl chloroformate (0.13 cc) is added to a solution, kept at −10° C., of benzyl N-lauroyl-L-alanyl-α-D-glutamate (491 mg) in a mixture of tetrahydrofurane (25 cc) and triethylamine (0.14 cc). The mixture is stirred for 10 minutes at −10° C. and a solution, cooled to 0° C., of N-ε-(benzyloxycarbonylglycyl)-L-lysine (337 mg) in tetrahydrofurane (25 cc) and 1N sodium hydroxide solution (1 cc) is then added. The reaction medium is stirred for 2 hours at 10° C. and then for 20 hours at a temperature of the order of 20° C. It is then acidified to pH 1 by adding 1N hydrochloric acid (2 cc). The tetrahydrofurane is evaporated off under reduced pressure (20 mm Hg) at 40° C. The remaining aqueous solution is extracted with ethyl acetate (50 cc) and the organic phase is washed twice with 0.1N hydrochloric acid (20 cc in total) and with a saturated solution of sodium chloride (10 cc) and dried over anhydrous magnesium sulphate. Concentration to dryness under reduced pressure (20 mm Hg) at 40° C. yields a white solid (600 mg) which is chromatographed on a column of diameter 2 cm, containing neutral silica gel (30 g).

Elution is carried out successively with ethyl acetate (60 cc), a mixture of ethyl acetate and methanol (9/1 by volume) (100 cc), a mixture of ethyl acetate and methanol (8/2 by volume) (60 cc) and a mixture of ethyl acetate and methanol (1/1 by volume ) (80 cc), 20 cc fractions being collected. Fractions 10 to 13 are combined and concentrated to dryness under reduced pressure (20 mm Hg) at 45° C. N-α-[O$^1$-Benzyl-N-(N-lauroyl-L-alanyl)-γ-D-glutamyl]-N-ε-(benzyloxycarbonylglycyl)-L-lysine (430 mg) is thus obtained.

Rf=0.77 [silica gel; n-butanol/acetic acid/water (7/1/2 by volume)].

N-α-[O$^1$-Benzyl-N-(N-lauroyl-L-alanyl)-γ-D-glutamyl]-N-ε-(benzyloxycarbonylglycyl)-L-lysine (420 mg) is dissolved in methanol (25 cc). Palladium-on-charcoal (containing 3% of palladium) (420 mg) is added and a slow stream of hydrogen is passed through the mixture for 3 hours. After filtering and concentrating the filtrate to dryness, N-α-[N-(N-lauroyl-L-alanyl)-γ-D-glutamyl]-N-ε-glycyl-L-lysine (270 mg) is obtained.

N-ε-(Benzyloxycarbonylglycyl)-L-lysine can be prepared in accordance with the method of D. THEODOROPOULOS, J. Org. Chem. 23, 140 (1958).

EXAMPLE 5

Isobutyl chloroformate (1.2 cc) is added to a solution, kept at 10° C., of benzyl N-lauroyl-L-alanyl-α-D-glutamate (4.42 g) in a mixture of dioxane (180 cc) and triethylamine (1.3 cc). The solution is stirred for 20 minutes at a temperature of the order of 10° C. and a solution, cooled to 10° C., of benzyl N-ε-benzyloxycarbonyl-L-lysyl-D-alaninate hydrochloride (4.09 g) in a mixture of dioxane (30 cc), water (5 cc) and triethylamine (1.3 cc) is then added. The reaction mixture is stirred for 20 hours at a temperature of the order of 20° C. Water (500 cc) is then added and the mixture is cooled to 0° C. After 2 hours at 0° C., the insoluble material is filtered off, washed with water (100 cc) and dried. Benzyl N-α-[O$^1$-benzyl-N-(N-lauroyl-L-alanyl)-γ-D-glutamyl]-N-ε-benzyloxycarbonyl-L-lysyl-D-alaninate (7.86 g) is thus obtained.

Rf=0.92 [silica gel; ethyl acetate/methanol (4/1 by volume)].

Benzyl N-α-[O$^1$-benzyl-N-(N-lauroyl-L-alanyl)-γ-D-glutamyl]-N-ε-benzyloxycarbonyl-L-lysyl-D-alaninate (7.80 g) is dissolved in a mixture of methanol (250 cc) and dioxane (530 cc). Palladium-on-charcoal (containing 3% of palladium) (7.80 g) is added and a slow stream of hydrogen is passed through the mixture for 5 hours. Crystallisation on the palladium-on-charcoal is observed. The catalyst is filtered off and washed with a mixture of methanol and dioxane (½ by volume) (100 cc) and then 5 times with methanol (500 cc in total), thus entraining the crystalline product. The methanol phase is concentrated to dryness under reduced pressure (20 mm Hg) at 50° C. This yields a powder (1.5 g) which is chromatographed on a Sephadex LH 20 column (diameter: 2 cm; height: 2 m). Elution is carried out with methanol, 5 cc fractions being collected. Fractions 41 to 69 are combined and concentrated to dryness under reduced pressure (20 mm Hg) at 50° C. The residue is dissolved in boiling methanol (50 cc), and dioxane (120 cc) is then added. The mixture is left to return to a temperature of the order of 20° C. After standing for 5 hours, the precipitate which has appeared is filtered off, washed with dioxane (10 cc) and then dried under reduced pressure (0.2 mm Hg) at 60° C. N-α-[N-(N-Lauroyl-L-alanyl)-γ-D-glutamyl]-L-lysyl-D-alanine (1.37 g), which melts at 170° C. (to give a paste), is thus obtained.

Rf=0.26 [silica gel; n-butanol/pyridine/acetic acid/water (50/20/6/24 by volume)].

Analysis calculated %; C, 58.07; H, 8.91; N, 11.68; found C, 57.4; H, 8.9; N, 11.4.

After total hydrolysis, analysis on a Technicon autoanalyser shows the presence of the following aminoacids:

Ala 2.00 (theory=2)
Glu 1.04 (theory=1)
Lys 1.01 (theory=1)

Benzyl N-ε-benzyloxycarbonyl-L-lysyl-D-alaninate hydrochloride can be prepared in accordance with the method of S. KUSUMOTO et al., Bull. Chem. Soc. Japan, 49, 533 (1976).

EXAMPLE 6

Isobutyl chloroformate (1.3 cc) is added to a solution, kept at 10° C., of benzyl N-lauroyl-L-alanyl-α-D-glutamate (4.91 g) in a mixture of dioxane (200 cc) and triethylamine (1.4 cc). The solution is stirred for 20 minutes at a temperature of the order of 10° C. and a solution of benzyl N-ε-benzyloxycarbonyl-L-lysyl-glycinate hydrochloride (4.64 g) in a mixture of dioxane (30 cc), water (5 cc) and triethylamine (1.4 cc) is then added. The reaction mixture is stirred for 20 hours at about 20° C. The reaction mixture is then poured into water (500 cc). The insoluble material formed is filtered off, washed with water (50 cc) and then dried. This yields a white powder (8.94 g) which is dissolved in dimethylformamide (500 cc) at 60° C. Water (500 cc) is added. After cooling to 0° C., the insoluble material is filtered off, drained, washed with water (100 cc) and then dried. Benzyl N-α-[O$^1$-benzyl-N-(N-lauroyl-L-alanyl)-γ-D-glutamyl]-N-ε-benzyloxycarbonyl-L-lysyl-glycinate (6.26 g) is thus obtained.

Rf=0.89 [silica gel; ethyl acetate/methanol (5/1 by volume)].

Benzyl N-α-[O$^1$-benzyl-N-(N-lauroyl-L-alanyl)-γ-D-glutamyl]-N-ε-benzyloxycarbonyl-L-lysyl-glycinate (6.20 g) is dissolved in a mixture of dioxane (425 cc) and methanol (125 cc) at 60° C. The solution is cooled to 40° C., palladium-on-charcoal (containing 3% of palladium) (6.20 g) is added and a stream of hydrogen is then passed through the mixture for 4 hours. Filtering and concentrating the filtrate to dryness under reduced pressure (20 mm Hg) at 50° C. yields a mixture (5.44 g) which still contains starting product. The residue is dissolved in a mixture of methanol (1 liter) and dioxane (200 cc) at 60° C. The solution is cooled to 30° C., palladium-on-charcoal (containing 3% of palladium) (5.44 g) is added and a stream of hydrogen is passed through the mixture for 4 hours. The reaction mixture is filtered, and the filter is washed twice with methanol (200 cc in total) and 4 times with boiling methanol (800 cc in total). The washing phase obtained with the boiling methanol is concentrated to dryness under reduced pressure (20 mm Hg) at 40° C. The resulting residue is triturated in ether (100 cc) to a powder. After the powder has been filtered off and dried, N-α-[N-(N-lauroyl-L-alanyl)-γ-D-glutamyl]-L-lysyl-glycine (1.74 g), which melts at 165°–170° C. (to give a paste), is obtained.

Rf=0.39 [silica gel; methanol].

Analysis calculated % C, 57.41; H, 8.78; N, 11.96. found C, 57.4; H, 9.1; N, 11.8.

After total hydrolysis, analysis on a Technicon autoanalyser shows the presence of the following aminoacids:
Ala 1.00 (theory=1)
Glu 1.01 (theory=1)
Gly 1.01 (theory=1)
Lys 0.84 (theory=1)

Benzyl N-ε-benzyloxycarbonyl-L-lysyl-glycinate hydrochloride can be prepared in accordance with the method of V. Bondar et al., Dokl. Akad. Nauk. Tadzh. SSR, 13, 14 (1970) (Chem. Abstr. 73, 66884 e).

EXAMPLE 7

Isobutyl chloroformate (0.85 cc) is added to a solution, kept at −4° C., of N-lauroylglycine (1.67 g) in tetrahydrofurane (150 cc) and triethylamine (0.91 cc). The solution is stirred for 20 minutes at −4° C. and a solution, cooled to 2° C., of N-α-[N-(N-t-butoxycarbonyl-L-alanyl)-γ-D-glutamyl]-N-lysine (3.74 g) in a mixture of tetrahydrofurane (50 cc) and 1N sodium hydroxide solution (13 cc) is then added. The reaction mixture is stirred for 1 hour at 0° C. and then for 18 hours at about 20° C. The tetrahydrofurane is then evaporated off by concentration under reduced pressure (20 mm Hg) at 40° C.; the concentrate is diluted by adding water (50 cc) and acidified to pH 2 by adding 1N hydrochloric acid. The insoluble material is filtered off, washed with water (50 cc) and then dried. This yields a powder (5.8 g) which is chromatographed on a column of diameter 12 mm, containing neutral silica gel (0.04–0.063 mm) (50 g). Elution is carried out successively with ethyl acetate (220 cc), a mixture of ethyl acetate and methanol (95/5 by volume) (120 cc), a mixture of ethyl acetate and methanol (9/1 by volume) (80 cc), a mixture of ethyl acetate and methanol (8/2 by volume) (180 cc), a mixture of ethyl acetate and methanol (7/3 by volume) (100 cc) and a mixture of ethyl acetate and methanol (1/1 by volume) (60 cc), 20 cc fractions being collected. Fractions 21 to 38 are combined and concentrated to dryness under reduced pressure (20 mm Hg) at 50° C. This yields a powder (780 mg) to which a product (270 mg) prepared under the same conditions is added, and the whole is dissolved in methanol (25 cc) containing neutral silica gel (0.04–0.063 mm) (5 g). The mixture is concentrated to dryness and the whole is introduced onto a column of diameter 12 mm, containing neutral silica gel (0.04–0.063 mm) (50 g). Elution is carried out successively with ethyl acetate (200 cc), a mixture of ethyl acetate and methanol (98/2 by volume) (200 cc), a mixture of ethyl acetate and methanol (96/4 by volume) (560 cc), a mixture of ethyl acetate and methanol (9/1 by volume) (680 cc) and methanol (280 cc), 40 cc fractions being collected. Fractions 43 and 44 are combined and concentrated to dryness under reduced pressure (20 mm Hg) at 50° C. N-α-[N-(N-t-butoxycarbonyl-L-alanyl)-γ-D-glutamyl]-N-ε-(N-lauroylglycyl L-lysine (850 mg) is thus obtained.

Rf=0.50 [silica gel; n-butanol/pyridine/acetic acid/water (50/20/6/24 by volume)].

N-α-[N-(N-t-butoxycarbonyl-L-alanyl)-γ-D-glutamyl]-N-ε-(N-lauroylglycyl)-L-lysine (830 mg) is dissolved in a 1.7N anhydrous solution of hydrogen chloride in acetic acid (20 cc). The resulting solution is stirred for 2 hours and ether (100 cc) is then added. The resulting precipitate is filtered off, washed with ether (50 cc) and dried under reduced pressure (0.2 mm Hg) at 50° C. N-α-[N-L-Alanyl-γ-D-glutamyl]-N-ε-(N-lauroylglycyl)-L-lysine hydrochloride (790 mg) is thus obtained.

Rf=0.34 [silica gel; n-butanol/pyridine/acetic acid/water (50/20/6/24 by volume)].

After total hydrolysis, analysis on a Technicon autoanalyser shows the presence of the following aminoacids:
Ala 1.04 (theory=1)
Glu 1.02 (theory=1)
Gly 1.00 (theory=1)
Lys 1.00 (theory=1)

N-α-[N-(N-t-Butoxycarbonyl-L-alanyl)-γ-D-glutamyl]-L-lysine can be prepared in the following manner:

Benzyl N-α-[O$^1$-benzyl-N-(N-t-butoxycarbonyl-L-alanyl)-γ-D-glutamyl]-N-ε-benzyloxycarbonyl-L-lysinate (4.95 g) is dissolved in acetic acid (250 cc). Palladium-on-charcoal (containing 3% of palladium (4.95 g) is added and a slow stream of hydrogen is passed through the mixture for 2 hours. After filtering and concentrating the filtrate to dryness under reduced pressure (0.2 mm Hg), N-α-[N-(N-t-butoxycarbonyl-L-alanyl)-γ-D-glutamyl]-L-lysine (3.74 g) is obtained.

Rf=0.20 [silica gel; n-butanol/pyridine/acetic acid/water (50/20/6/24 by volume)].

Benzyl N-α-[O$^1$-benzyl-N-(N-t-butoxycarbonyl-L-alanyl)-γ-D-glutamyl]-N-ε-benzyloxycarbonyl-L-lysinate can be prepared in the following manner:

Isobutyl chloroformate (1.95 cc) is added to a solution, kept at −10° C., of benzyl t-butoxycarbonyl-L-alanyl-α-D-glutamate (6.13 g) in tetrahydrofurane (200 cc) and triethylamine (2.1 cc). The solution is stirred for 20 minutes at −10° C. and a solution of benzyl N-ε-benzyloxycarbonyl-L-lysinate hydrochloride (6.71 g) in tetrahydrofurane (100 cc) and triethylamine (2.3 cc) is then added. The reaction mixture is stirred for 30 minutes at −5° C. and then for 66 hours at about 20° C. The reaction mixture is then concentrated to dryness under reduced pressure (20 mm Hg) at 30° C. This yields an oil (15.95 g) which is chromatographed on a column of diameter 3 cm, containing neutral silica gel (0.063–0.20 mm) (150 g). Elution is carried out successively with a mixture of ethyl acetate and cyclohexane (4/6 by volume) (400 cc), a mixture of ethyl acetate and cyclohexane (6/4 by volume) (240 cc) and ethyl acetate (560 cc), 40 cc fractions being collected. Fractions 15 to 23 are combined and concentrated to dryness under reduced pressure (20 mm Hg) at 40° C. This yields a partially crystalline oil (9.25 g) which is dissolved in ethyl acetate (40 cc) at 45° C. Cyclohexane (100 cc) is added. The mixture is left to return to a temperature of the order of 20° C. The insoluble material is filtered off, washed with a mixture of ethyl acetate and cyclohexane (4/6 by volume) (25 cc) and then dried. Benzyl N-α-[O$^1$-benzyl-N-(N-t-butoxycarbonyl-L-alanyl)-γ-glutamyl]-N-ε-benzyloxycarbonyl-L-lysinate (4.99 g) is thus obtained.

Rf=0.80 [silica gel; ethyl acetate/methanol (9/1 by volume)].

Mass spectrometry: M=760 (theory=760).

EXAMPLE 8

Isobutyl chloroformate (0.41 cc) is added to a solution, kept at −5° C., of N-lauroylglycine (808 mg) in tetrahydrofurane (50 cc) and triethylamine (0.44 cc). The solution is stirred for 20 minutes at −5° C. and a solution, cooled to 0° C., of N-α-[N-(N-lauroyl-L-alanyl)-γ-D-glutamyl]-L-lysine (1.81 g) in a mixture of tetrahydrofurane (20 cc) and 1N sodium hydroxide solution (6.3 cc) is then added. The reaction mixture is stirred for 1 hour at about −5° C. and then for 18 hours at about 20° C. The reaction mixture is then acidified to about pH 1 by adding 1N hydrochloric acid (10 cc), the tetrahydrofurane is evaporated off by concentration under reduced pressure (20 mm Hg) at 45° C. and ethyl acetate (50 cc) and water (30 cc) are then added to the concentrate. The insoluble material is filtered off, washed with ethyl acetate (20 cc) and water (10 cc) and dried under reduced pressure (20 mm Hg). This yields a powder (1.18 g) which is chromatographed on a column of diameter 12 mm, containing neutral silica gel (0.063–0.20 mm) (50 g). Elution is carried out successively with a mixture of ethyl acetate and methanol (75/25 by volume) (80 cc), a mixture of ethyl acetate and methanol (1/1 by volume) (320 cc) and methanol (120 cc), 40 cc fractions being collected. Fractions 4 to 8 are combined and concentrated to dryness under reduced pressure (20 mm Hg) at 50° C. The resulting residue is triturated in ether (50 cc), filtered off and dried. This yields a powder (0.88 g) which is chromatographed on a column of diameter 12 mm, containing neutral silica gel (0.04–0.063 mm) (20 g). Elution is carried out successively with ethyl acetate (180 cc), a mixture of ethyl acetate and methanol (99/1 by volume) (60 cc), a mixture of ethyl acetate and methanol (98/2 by volume) (100 cc), a mixture of ethyl acetate and methanol (95/5 by volume) (260 cc), a mixture of ethyl acetate and methanol (9/1 by volume) (120 cc), a mixture of ethyl acetate and methanol (85/15 by volume) (60 cc), a mixture of ethyl acetate and methanol (8/2 by volume) (280 cc), a mixture of ethyl acetate and methanol (7/3 by volume) (40 cc), a mixture of ethyl acetate and methanol (6/4 by volume) (40 cc) and a mixture of ethyl acetate and methanol (1/1 by volume) (60 cc), 20 cc fractions being collected. Fractions 41 to 60 are combined and concentrated to dryness under reduced pressure (20 mm Hg) at 50° C. N-$\alpha$-[N-(N-Lauroyl-L-alanyl)-$\gamma$-D-glutamyl]-N-$\epsilon$-(N-lauroylglycyl)-L-lysine (740 mg), which melts at 167°–171° C. (to give a paste), is thus obtained.

Rf=0.58 [silica gel; n-butanol/pyridine/acetic acid/water (50/20/6/24 by volume)].

Analysis: calculated %=C, 62.55; H, 9.58; N, 9.12; found (corrected) C, 62.5; H, 9.6; N, 9.3.

After total hydrolysis, analysis on a Technicon autoanalyser shows the presence of the following aminoacids:
Ala 1.01 (theory=1)
Glu 0.95 (theory=1)
Gly 1.00 (theory=1)
Lys 0.97 (theory=1)

EXAMPLE 9

Isobutyl chloroformate (0.5 cc) is added to a solution, kept at 12° C., of benzyl N-lauroyl-L-alanyl-$\alpha$-D-glutamate (1.89 g) in dioxane (75 cc) and triethylamine (0.54 cc). The mixture is stirred for 20 minutes at 12° C. and a solution, cooled to 10° C., of benzyl N$^6$-benzyloxycarbonyl-D,D/L,L-2,6-diaminopimelamoylglycinate hydrochloride (1.95 g) in a mixture of dioxane (20 cc), water (1.5 cc) and triethylamine (0.54 cc) is then added. The reaction mixture is stirred for 18 hours at a temperature of the order of 20° C. and then diluted by adding water (150 cc) and acidified to pH 1 by adding 1N hydrochloric acid (5 cc). The precipitate thus obtained is filtered off, washed 3 times with water (75 cc in total) and dried. This yields a white product (3.36 g) which is chromatographed on a column of diameter 2.5 cm, containing neutral silica gel (0.04–0.063 mm) (60 g). To do this, the product is dissolved in acetic acid (30 cc). Silica (20 g) is added to the resulting solution and the mixture is then concentrated to dryness under reduced pressure (20 mm Hg) at 45° C. The residue thus obtained is introduced onto the column and elution is carried out successively with a mixture of ethyl acetate and acetic acid (95/5 by volume) (160 cc), a mixture of ethyl acetate and acetic acid (9/1 by volume) (1,040 cc), a mixture of ethyl acetate and acetic acid (8/2 by volume) (360 cc) and acetic acid (360 cc), 40 cc fractions being collected. Fractions 10 to 16 are combined and concentrated to dryness under reduced pressure (20 mm Hg) at 45° C. Benzyl N$^2$-[O$^1$-benzyl-N-(N-lauroyl-L-alanyl)-$\gamma$-D-glutamyl]-N$^6$-benzyloxycarbonyl-D,D/L,L-2,6-diaminopimelamoyl-glycinate (1.09 g), which melts at 204°–206° C., is thus obtained. Fractions 17 to 48 are combined and concentrated to dryness. The residue is chromatographed on a column of diameter 2 cm, containing neutral silica gel (0.04–0.063 mm) (40 g). Elution is carried out with a mixture of ethyl acetate and acetic acid (1/1 by volume) (280 cc), 20 cc fractions being collected. Fractions 4 and 5 are combined and concentrated to dryness. The residue is triturated in ether (20 cc), filtered off and dried. Benzyl N$^2$-[O$^1$-benzyl-N-(N-lauroyl-L-alanyl)-$\gamma$-D-glutamyl]-N$^6$-benzyloxycarbonyl-D,D/L,L-2,6-diaminopimelamoyl-glycinate (0.7g), which melts at 204°–206° C., is thus obtained.

Rf=0.83 [silica gel; ethyl acetate/acetic acid (3/1 by volume)].

Benzyl N$^2$-[O$^1$-benzyl-N-(N-lauroyl-L-alanyl)-$\gamma$-D-glutamyl]-N$^6$-benzyloxycarbonyl-D,D/L,L-2,6-diaminopimelamoyl-glycinate (1.74 g) is dissolved in acetic acid (50 cc). Palladium-on-charcoal (containing 3% of palladium) (1.74 g) is added and a slow stream of hydrogen is then passed through the mixture for 2 hours. After filtration, ether (200 cc) is added to the filtrate. After standing for 1 hour at 20° C., the precipitate formed is filtered off, washed with ether (25 cc) and dried under reduced pressure (0.2 mm Hg) at 50° C. N$^2$[N-(N-Lauroyl-L-alanyl)-$\gamma$-D-glutamyl]-D,D/L,L-2,6-diaminopimelamoyl-glycine (1.09 g), which melts at 180°–182° C. (to give a paste) and contains 1.4% of water (Fischer's method), is thus obtained.

Rf=0.30 [silica gel; n-butanol/pyridine/acetic acid/water (50/20/6/24 by volume)].

Analysis: calculated %=C, 55.40; H, 8.34; N, 13.36; found=C, 53.4; H, 8.5; N, 12.4.

Sulphuric ash %=0.8.

After total hydrolysis, analysis on a Technicon autoanalyser shows the presence of the following aminoacids:
Ala=1.02 (theory=1)
Glu=1.01 (theory=1)
Gly=1.00 (theory=1)
Dap=0.98 (theory=1)

Benzyl N$^6$-benzyloxycarbonyl-D,D/L,L-2,6-diaminopimelamoyl-glycinate hydrochloride can be prepared in the following manner:

Benzyl N$^2$-t-butoxycarbonyl-N$^6$-benzyloxycarbonyl-D,D/L,L-2,6-diaminopimelamoyl-glycinate (2.48 g) is dissolved in a 1.7N anhydrous solution of hydrogen chloride in acetic acid (12.5 cc). The resulting solution is stirred for 2 hours and ether (200 cc) is then added. The pasty precipitate which has formed is separated from the supernatant liquor by decantation and is dissolved in hot acetone (⅛cc). After cooling, ether (150 cc) is added. The crystals formed are filtered off, washed twice with ether (40 cc in total) and dried under reduced pressure (0.2 mm Hg) at 20° C. Benzyl N⁶-benzyloxycarbonyl-D,D/L,L-2,6-diaminopimelamoyl-glycinate hydrochloride (1.95 g) is thus obtained.

Rf=0.61 [silica gel; n-butanol/pyridine/acetic acid/water (50/20/6/24 by volume)].

Benzyl N²-t-butoxycarbonyl-N⁶-benzyloxycarbonyl-D,D/L,L-2,6-diaminopimelamoyl-glycinate can be prepared in the following manner:

Isobutyl chloroformate (1.17 cc) is added to a solution, kept at −1° C., of N²-t-butoxycarbonyl-N⁶-benzyloxycarbonyl-D,D/L,L-2,6-diaminopimelamic acid (3.81 g) in tetrahydrofurane (90 cc) and triethylamine (1.26 cc). The mixture is stirred for 20 minutes at −1° C. and a solution, cooled to −1° C., of benzyl glycinate p-toluenesulphonate (3.028 g) in tetrahydrofurane (90 cc) and triethylamine (1.33 cc) is then added. The reaction mixture is stirred for 2 hours at −1° C. and then for 70 hours at about 20° C. It is then concentrated to dryness under reduced pressure (20 mm Hg) at 35° C. The residue is taken up in ethyl acetate (100 cc). The resulting solution is washed successively with water (20 cc), 3 times with a 5% strength solution of sodium bicarbonate (60 cc in total), 3 times with a saturated solution of citric acid (60 cc in total) and then with a saturated solution of sodium chloride (10 cc). The organic phase is dried over anhydrous magnesium sulphate and concentrated to dryness under reduced pressure (20 mm Hg) at 45° C. This yields a hard cream foam (4.8 g) which is chromatographed on a column of diameter 2 cm, containing neutral silica gel (0.04–0.063 mm) (100 g). Elution is carried out successively with a mixture of cyclohexane and ethyl acetate (1/1 by volume) (320 cc), a mixture of cyclohexane and ethyl acetate (1/3 by volume) (360 cc) and ethyl acetate (640 cc), 40 cc fractions being collected. Fractions 13 to 23 are combined and concentrated to dryness under reduced pressure (20 mm Hg) at 45° C. Benzyl N²-t-butoxycarbonyl-N⁶-benzyloxycarbonyl-D,D/L,L-2,6-diaminopimelamoyl-glycinate (2.29 g) is thus obtained.

Rf=0.26 [silica gel; ethyl acetate].

N²-t-Butoxycarbonyl-N⁶-benzyloxycarbonyl-D,D/L,L-2,6-diaminopimelamic acid can be prepared in the following manner:

A solution of di-t-butyl dicarbonate (6 g) in dioxane (50 cc) is added to a suspension of N⁶-benzyloxycarbonyl-D,D/L,L-2,6-diaminopimelamic acid (8.08 g) and sodium carbonate (2.65 g) in a mixture of water (50 cc) and dioxane (150 cc). The reaction mixture is stirred for 16 hours at a temperature of the order of 20° C. The insoluble material is filtered off and the filtrate is concentrated to dryness under reduced pressure (20 mm Hg) at 45° C. The residue is taken up in water (50 cc) and ethyl acetate (50 cc). The aqueous phase is acidified to pH 3 by adding a saturated solution of citric acid (20 cc). The organic phase is separated off by decantation and the aqueous phase is then extracted twice with ethyl acetate (50 cc in total). The organic phases are combined, washed with a saturated solution of sodium chloride (20 cc), dried over anhydrous magnesium sulphate and concentrated to dryness under reduced pressure (20 mm Hg) at 45° C. N²-t-Butoxycarbonyl-N⁶-benzyloxycarbonyl-D,D/L,L-2,6-diaminopimelamic acid (7.47 g) is thus obtained in the form of a hard white foam.

Rf=0.62 [silica gel; ethyl acetate/methanol (1/1 by volume)].

EXAMPLE 10

Isobutyl chloroformate (0.30 cc) is added to a solution, kept at −5° C., of N-benzyloxycarbonylglycine (484 mg) in tetrahydrofurane (50 cc) and triethylamine (0.323 cc). The mixture is stirred for 20 minutes at −5° C. and a solution of N²-[N-(N-lauroyl-L-alanyl)-D-isoglutaminyl]-D,D/L,L-2,6-diaminopimelamic acid (1.32 g) in a mixture, cooled to 2° C., of water (50 cc), tetrahydrofurane (25 cc) and 1N sodium hydroxide solution (2.31 cc) is then added. The mixture is stirred for 1 hour at 5° C. and for 18 hours at about 20° C. The tetrahydrofurane is then evaporated off under reduced pressure (20 mm Hg) at 50° C. and the concentrate is acidified to pH 1 by adding 1N hydrochloric acid (10 cc). The precipitate formed is filtered off, washed 3 times with water (30 cc in total) and dried. This yields a beige powder (1.57 g) which is chromatographed on neutral silica gel (0.04–0.063 mm) (30 g) contained in a column of diameter 15 mm. Elution is carried out successively with a mixture of ethyl acetate and methanol (9/1 by volume) (60 cc), a mixture of ethyl acetate and methanol (8/2 by volume) (60 cc), a mixture of ethyl acetate and methanol (7/3 by volume) (60 cc), a mixture of ethyl acetate and methanol (6/4 by volume) (60 cc) and a mixture of ethyl acetate and methanol (1/3 by volume) (60 cc), 20 cc fractions being collected. Fractions 11 to 17 are combined and concentrated to dryness under reduced pressure (20 mm Hg) at 50° C. The residual oil is triturated in ether (50 cc). After filtration and drying, N²-[N-(N-lauroyl-L-alanyl)-D-isoglutaminyl]-N⁶-(benzyloxycarbonylglycyl)-D,D/L,L-2,6-diaminopimelamic acid (1.02 g) is obtained in the form of a white solid which melts at 115°–120° C. (to give a paste).

Rf=0.41 [silica gel; ethyl acetate/acetic acid (1/1 by volume)].

N²-[N-(N-Lauroyl-L-alanyl)-D-isoglutaminyl]-N⁶-(benzyloxycarbonylglycyl)-D,D/L,L-2,6-diaminopimelamic acid (1 g) is dissolved in acetic acid (25 cc). Palladium-on-charcoal (containing 3% of palladium) (1 g) is added and a slow stream of hydrogen is then passed through the mixture for 3 hours. After filtering and concentrating the filtrate to dryness under reduced pressure (20 mm Hg) at 50° C., the resulting residue is triturated in ether (30 cc), filtered off, washed with ether (10 cc) and dried under reduced pressure (0.2 mm Hg) at 50° C. N²-[N-(N-Lauroyl-L-alanyl)-D-isoglutaminyl]-N⁶-(glycyl)-D,D/L,L-2,6-diaminopimelamic acid (790 mg), which melts at 170°–174° C. (to give a paste), is thus obtained.

Rf=0.34 [silica gel; n-butanol/pyridine/acetic acid/water (50/20/6/24 by volume)].

Analysis: calculated %=C, 55.48; H, 8.51; N, 15.62; found=C, 54.25; H, 8.31; N, 14.82.

Sulphuric ash %=3.7

After total hydrolysis, analysis on a Technicon autoanalyser shows the presence of the following amino-acids:

Ala 1.02 (theory=1)
Dap 0.98 (theory=1)
Glu 1.05 (theory=1)
Gly 1.00 (theory=1)

N²-[N-(N-Lauroyl-L-alanyl)-D-isoglutaminyl]-D,D/L,L-2,6-diaminopimelamic acid can be prepared in the following manner:

N²-[N-(N-Lauroyl-L-alanly)-D-isoglutaminyl]-N⁶-benzyloxycarbonyl-D,D/L,L-2,6-diaminopimelamic acid (1.76 g) is dissolved in acetic acid (80 cc). Palladium-on-charcoal (containing 3% of palladium) (1.76 g) is added and a stream of hydrogen is then passed through the mixture for 2 and a half hours. After filtration, the filtrate is concentrated to about 5 cc and diluted by adding ether (100 cc). The precipitate formed is filtered off, washed twice with ether (40 cc in total) and dried. This yields $N^2$-[N-(N-lauroyl-L-alanyl)-D-isoglutaminyl]-D,D/L,L-2,6-diaminopimelamic acid (1.37 g).

Rf=0.40 [silica gel; n-butanol/pyridine/acetic acid/water (50/20/6/24 by volume)].

$N^2$-[N-(N-Lauroyl-L-alanyl)-D-isoglutaminyl]-$N^6$-benzyloxycarbonyl-D,D/L,L-2,6-diaminopimelamic acid can be prepared in the following manner:

Isobutyl chloroformate (0.81 cc) is added to a solution, kept at −5° C., of N-lauroyl-L-alanyl-D-isoglutamine (2.5 g) in dimethylformamide (150 cc) and triethylamine (0.87 cc). The mixture is stirred for 20 minutes, at −5° C. and a solution, cooled to +2° C., of $N^6$-benzyloxycarbonyl-D,D/L,L-2,6-diaminopimelamic acid (2.02 g) in a mixture of water (62.5 cc) and 1N sodium hydroxide solution (6.25 cc) is then added. The reaction mixture is stirred for 1 hour at 0° C. and then for 18 hours at about 20° C. and is subsequently filtered. The filtrate, diluted by adding water (300 cc), is acidified to pH 1 by adding 1N hydrochloric acid (15 cc). The precipitate which has appeared is filtered off, washed 3 times with water (30 cc in total) and then dried. This yields a white solid (2.03 g) to which a product (680 mg) obtained under similar conditions is added. The mixture is dissolved in acetic acid (30 cc) containing neutral silica gel (0.04–0.063 mm) (5 g). The mixture is concentrated to dryness and the residue is then deposited on a column of diameter 2 cm, containing neutral silica gel (0.04–0.063 mm) (60 g). Elution is carried out successively with a mixture of ethyl acetate and acetic acid (9/1 by volume) (400 cc), a mixture of ethyl acetate and acetic acid (8/2 by volume) (360 cc), a mixture of ethyl acetate and acetic acid (7/3 by volume) (240 cc), a mixture of ethyl acetate and acetic acid (1/1 by volume) (160 cc) and acetic acid (480 cc), 40 cc fractions being collected. Fractions 17 to 49 are combined and concentrated to dryness. This yields $N^2$-[N-(N-lauroyl-L-alanyl)-D-isoglutaminyl]-$N^6$-benzyloxycarbonyl-D,D/L,L-2,6-diaminopimelamic acid (1.78 g).

Rf=0.65 [silica gel; ethyl acetate/acetic acid (3/1 by volume)].

N-Lauroyl-L-alanyl-D-isoglutamine can be prepared in the following manner:

Benzyl N-lauroyl-L-alanyl-D-isoglutaminate (6.6 g) is dissolved in acetic acid (330 cc). Palladium-on-charcoal (containing 3% of palladium) (6.6 g) is added and a slow stream of hydrogen is then passed through the mixture for 2 hours. After filtering the reaction mixture, the filtrate is poured into water (3 liters). After standing for 2 hours at 0° C., the precipitate which has appeared is filtered off, washed twice with water (80 cc in total) and then dried. This yields a product (5.16 g) to which a product (0.5 g) obtained under similar conditions is added. This mixture is dissolved in boiling methanol (90 cc), and water (45 cc) is added to the resulting solution. After standing for 2 hours at a temperature of the order of 20° C., the crystals which have appeared are filtered off, washed twice with water (60 cc in total) and dried under reduced pressure (20 mm Hg). This yields N-lauroyl-L-alanyl-D-isoglutamine (5.1 g) which melts at 163° C.

Rf=0.18 [silica gel; ethyl acetate/methanol (4/1 by volume)].

Analysis: calcuated %=C, 60.12; H, 9.33; N, 10.52; found=C, 60.2; H, 9.5; N, 10.9.

Benzyl N-lauroyl-L-alanyl-D-isoglutaminate can be prepared in the following manner:

Isobutyl chloroformate (2.54 cc) is added to a solution, kept at 0° C., of lauric acid (3.9 g) in anhydrous toluene (156 cc) and triethylamine (2.7 cc). The mixture is stirred for 20 minutes at 0° C. and a solution, cooled to 0° C., of benzyl L-alanyl-D-isoglutaminate hydrochloride (6.7 g) in water (52 cc) and triethylamine (2.7 cc) is then added. The reaction mixture is stirred for 65 hours at a temperature of the order of 20° C. This yields a reaction mixture of gelatinous appearance, to which ethyl acetate (150 cc) is added. The precipitate is filtered off, washed with water (30 cc) and then dried. This yields benzyl N-lauroyl-L-alanyl-D-isoglutaminate (7.6 g) in the form of a white powder. The aqueous phase of the above filtrate is extracted twice with ethyl acetate (100 cc in total), this ethyl acetate phase is combined with the organic phase of the filtrate and the combined phase is washed with 0.1N hydrochloric acid (125 cc) and water (120 cc), dried over magnesium sulphate and then concentrated to dryness under reduced pressure (20 mm Hg) at 50° C. This yields a further amount of benzyl N-lauroyl-L-alanyl-D-isoglutaminate (1.5 g). The product (7.6 g and 1.5 g) is recrystallised from methanol (120 cc). This yields benzyl N-lauroyl-L-alanly-D-isoglutaminate (6.6 g) which melts at 169° C.

Rf=0.13 [silica gel; ethyl acetate].

Benzyl L-alanyl-D-isoglutaminate hydrochloride can be prepared in accordance with the process of S. KUSUMOTO, Bull. Chem. Soc. Japan, 49, 533 (1976).

EXAMPLE 11

Isobutyl chloroformate (0.44 cc) is added to a solution, kept at −5° C., of N-benzyloxycarbonylglycine (710 mg) in tetrahydrofurane (67 cc) and triethylamine (0.475 cc). The mixture is stirred for 20 minutes at −5° C. and a solution of $N^2$[N-(N-octanoyl-L-alanyl)-γ-D-glutamyl]-D,D/L,L-2,6-diaminopimelamic acid (1.75 g) in a mixture, cooled to 2° C., of water (6.7 cc) and 1N sodium hydroxide (6.78 cc) is then added. The reaction mixture is stirred for ½ hour at 0° C. and for 18 hours at about 20° C. The tetrahydrofurane is then evaporated off under reduced pressure (20 mm Hg) at 45° C.; the remaining aqueous phase is diluted with water (50 cc) and acidified to pH 1 by adding 1N hydrochloric acid (10 cc). The precipitate formed is filtered off, washed 3 times with water (30 cc in total) and dried. This yields a whitish powder (1.65 g) which is chromatographed on neutral silica gel (0.04–0.063 mm) (33 g) contained in a column of diameter 22 mm. To do this, the powder is dissolved in acetic acid (20 cc), silica (5 g) is added and the mixture is concentrated to dryness under reduced pressure (20 mm Hg) at 50° C. The residue thus obtained is introduced onto the column and elution is carried out successively with a mixture of ethyl acetate and acetic acid (9/1 by volume) (280 cc), a mixture of ethyl acetate and acetic acid (85/15 by volume) (160 cc) and a mixture of ethyl acetate and acetic acid (8/2 by volume) (560 cc), 40 cc fractions being collected. Fractions 11 to 24 are combined and concentrated to dryness under reduced pressure (20 mm Hg) at 50° C. The residual oil is triturated in ether (40 cc). After filtration and drying, $N^2$-[N-(N-octanoyl-L-alanyl)-γ-D-glutamyl]-

$N^6$-(benzyloxycarbonylglycyl)-D,D/L,L-2,6-diaminopimelamic acid (1.37 g) is obtained in the form of a white solid which melts at about 100° C. (to give a paste).

Rf=0.47 [silica gel; ethyl acetate/acetic acid (1/1 by volume)].

$N^2$-[N-(N-Octanoyl-L-alanyl)-γ-D-glutamyl]-$N^6$-(benzyloxycarbonylglycyl)-D,D/L,L-2,6-diaminopimelamic acid (1.35 g) is dissolved in acetic acid (30 cc). Palladium-on-charcoal (containing 3% of palladium) (1.35 g) is added and a slow stream of hydrogen is passed through the mixture for 3 hours. After filtering and concentrating the filtrate to dryness under reduced pressure (20 mm Hg) at 50° C., the resulting residue is triturated in ether (50 cc), filtered off, washed with ether (10 cc) and dried under reduced pressure (0.2 mm Hg) at 50° C. $N^2$-[N-(N-Octanoyl-L-alanyl)-γ-D-glutamyl]-$N^6$-(glycyl)-D,D/L,L-2,6-diaminopimelamic acid (1.05 g), which melts at 170°–174° C. (to give a paste), is thus obtained.

Rf=0.24 [silica gel; n-butanol/pyridine/acetic acid/water (50/20/6/24 by volume)].

Analysis: calculated %=C, 52.44; H, 7.74; N, 14.68; found C, 51.29; H, 7.96; N, 14.00.

Sulphuric ash %=4.

After total hydrolysis, analysis on a Technicon autoanalyser shows the presence of the following aminoacids:

Ala 1.01 (theory=1)
Dap 0.98 (theory=1)
Glu 1.03 (theory=1)
Gly 1.00 (theory=1)

$N^2$-[N-(N-Octanoyl-L-alanyl)-γ-D-glutamyl]-D,D/L,L-2,6-diaminopimelamic acid can be prepared in the following manner:

$N^2$-[$O^1$-Benzyl-N-(N-octanoly-L-alanyl)-γ-D-glutamyl]-$N^6$-benzyloxycarbonyl-D,D/L,L-2,6-diaminopimelamic acid (2.82 g) is dissolved in acetic acid (80 cc). Palladium-on-charcoal (containing 3% of palladium) (2.82 g) is added and a stream of hydrogen is then passed through the mixture for 2½ hours. After filtration, the filtrate is concentrated to about 5 cc under reduced pressure (20 mm Hg) at 50° C. and diluted by adding ether (100 cc). This yields a precipitate which is filtered off, washed with ether (20 cc) and then dried. This yields $N^2$-[N-(N-octanoyl-L-alanyl)-γ-D-glutamyl]-D,D/L,L-2,6-diaminopimelamic acid (2.0 g) which melts at 160°–164° C. (to give a paste).

Rf=0.30 [silica gel; n-butanol/pyridine/acetic acid/water (50/20/6/24 by volume)].

Analysis: calculated %=C, 53.58; H, 8.02; N, 13.58; found=C, 53.05; H, 8.17; N, 13.06.

Sulphuric ash %=1.8.

After total hydrolysis, analysis on a Technicon autoanalyser shows the presence of the following aminoacids:

Ala 1.00 (theory=1)
Dap 0.95 (theory=1)
Glu 1.02 (theory=1)

$N^2$-[$O^1$-Benzyl-N-(N-octanoyl-L-alanyl)-γ-D-glutamyl]-$N^6$-benzyloxycarbonyl-D,D/L,L-2,6-diaminopimelamic acid can be prepared in the following manner:

Isobutyl chloroformate (0.91 cc) is added to a solution, kept at 0° C., of benzyl N-octanoyl-L-alanyl-α-D-glutamate (3.04 g) in tetrahydrofurane (150 cc) and triethylamine (0.98 cc). The mixture is stirred for 20 minutes at 0° C. and a solution, cooled to 2° C., of $N^6$-benzyloxycarbonyl-D,D/L,L-2,6-diaminopimelamic acid (2.26 g) in a mixture of water (70 cc) and 1N sodium hydroxide solution (7 cc) is then added. The reaction mixture is stirred for 1 hour at 0° C. and then for 20 hours at a temperature of the order of 20° C. The tetrahydrofurane is then evaporated off under reduced pressure (20 mm Hg) at 50° C. The concentrate is diluted by adding water (50 cc) and acidified to pH 1 by adding 1N hydrochloric acid (10 cc). The resulting white precipitate is filtered off, washed 3 times with water (75 cc in total) and then dried. This yields a white solid (4.73 g) which is chromatographed on a column of diameter 2.2 cm, containing neutral silica gel (0.04–0.063 mm) (100 g). To do this, the product is dissolved in acetic acid (20 cc). Neutral silica gel (10 g) is added to the resulting solution, and the mixture is concentrated to dryness under reduced pressure (20 mm Hg) at 50° C. The residue thus obtained is introduced onto the column and elution is carried out successively with ethyl acetate (280 cc), a mixture of ethyl acetate and acetic acid (9/1 by volume) (360 cc), a mixture of ethyl acetate and acetic acid (8/2 by volume) (200 cc) and a mixture of ethyl acetate and acetic acid (1/1 by volume) (160 cc), 40 cc fractions being collected. Fractions 13 to 23 are combined and concentrated to dryness under reduced pressure (20 mm Hg) at 50° C. This yields an oil which solidifies in ether. After filtering off and drying the solid, $N^2$-[$O^1$-benzyl-N-(N-octanoyl-L-alanyl)-γ-D-glutamyl]-$N^6$-benzyloxycarbonyl-D/D/L,L-2,6-diaminopimelamic acid (2.84 g) is obtained.

Rf=0.68 [silica gel; ethyl acetate/acetic acid (3/1 by volume)].

Benzyl N-octanoyl-L-alanyl-α-D-glutamate can be prepared in the following manner:

Isobutyl chloroformate (3.6 cc) is added to a solution, kept at −1° C., of octanoic acid (3.95 g) in tetrahydrofurane (140 cc) and triethylamine (3.8 cc). The mixture is stirred for 20 minutes at −1° C. and a solution, cooled to 0° C., of benzyl L-alanyl-α-D-glutamate hydrochloride (9.45 g) in a mixture of 1N sodium hydroxide solution (54.8 cc) and water (30 cc) is then added. The reaction mixture is stirred for 1 hour at −1° C. and then for 20 hours at about 20° C. It is then acidified to pH 1 by adding 1N hydrochloric acid. The tetrahydrofurane is evaporated off under reduced pressure (20 mm Hg) at 45° C. and the concentrate is then extracted with ethy acetate (100 cc). The organic phase thus obtained is washed twice with 1N hydrochloric acid (50 cc in total) and with a saturated solution of sodium chloride (25 cc) and concentrated to dryness under reduced pressure (20 mm Hg) at 45° C. This yields a pale yellow oil (10 g) which is chromatographed on a column of diameter 2.5 cm, containing neutral silica gel (0.063–0.20 mm) (200 g). Elution is carried out with ethyl acetate, 100 cc fractions being collected. Fractions 7 to 9 are combined and concentrated to dryness under reduced pressure (20 mm Hg) at 45° C. The resulting residue is triturated in a mixture of ether and petroleum ether (b.p.=35°–60° C.) (¼ by volume) (100 cc), filtered off and dried. Benzyl N-octanoyl-L-alanyl-α-D-glutamate (3.27 g) is thus obtained in the form of a white powder.

Rf=0.56 [silica gel; ethyl acetate/methanol (8/2 by volume)].

EXAMPLE 12

Isobutyl chloroformate (0.32 cc) is added to a solution, kept at −5° C., of N-benzyloxycarbonylglycine (512 mg) in tetrahydrofurane (25 cc) and triethylamine (0.35 cc). The mixture is stirred for 20 minutes at −5° C. and a solution of $N^2$-[N-(N-palmitoyl-L-alanyl)-γ-D-glutamyl]-D,D/L,L-2,6-diaminopimelamic acid (1.54 g) in a mixture, cooled to 2° C., of water (5 cc) and 1N sodium hydroxide solution (4.9 cc) is then added. The reaction mixture is stirred for 1 hour at −5° C. and for 18 hours at about 20° C. The tetrahydrofurane is then evaporated off under reduced pressure (20 mm Hg) at 50° C. The remaining aqueous phase is diluted with water (50 cc) and acidified to pH 1 by adding 1N hydrochloric acid (10 cc). The precipitate formed is filtered off, washed 3 times with water (30 cc in total) and dried. This yields a beige powder (1.80 g) which is chromatographed on neutral silica gel (0.04–0.063 mm) (36 g) contained in a column of diameter 22 mm. To do this, the powder is dissolved in acetic acid (20 cc), silica (5 g) is added and the mixture is concentrated to dryness under reduced pressure (20 mm Hg) at 50° C. The residue thus obtained is introduced onto the column and elution is carried out successively with a mixture of ethyl acetate and acetic acid (9/1 by volume) (120 cc), a mixture of ethyl acetate and acetic acid (8/2 by volume) (60 cc), a mixture of ethyl acetate and acetic acid (7/3 by volume) (60 cc), a mixture of ethyl acetate and acetic acid (1/1 by volume (60 cc) and acetic acid (80 cc), 20 cc fractions being collected. Fractions 10 to 16 are combined and concentrated to dryness under reduced pressure (20 mm Hg) at 50° C. The residual oil is triturated in ether (50 cc). After filtration and drying, $N^2$-[N-(N-palmitoyl-L-alanyl)-γ-D-glutamyl]-$N^6$-(benzyloxycarbonylglycyl)-D,D/L,L-2,6-diaminopimelamic acid (0.83 g), which melts at 124°–128° C. (to give a paste), is obtained.

Rf=0.50 [silica gel; ethyl acetate/acetic acid (1/1 by volume)].

$N^2$-[N-(N-Palmitoyl-L-alanyl)-γ-D-glutamyl]-$N^6$-(benzyloxycarbonylglycyl)-D,D/L,L-2,6-diaminopimelamic acid (1.14 g) is dissolved in acetic acid (30 cc). Palladium-on-charcoal (containing 3% of palladium) (1.14 g) is added and a slow stream of hydrogen is passed through the mixture for 3 hours. The reaction medium is then heated to about 65° C. and filtered and the filtrate is concentrated to dryness under reduced pressure (20 mm Hg) at 50° C.; the resulting residue is triturated in ether (50 cc), filtered off, washed with ether (10 cc) and dried under reduced pressure (0.2 mm Hg) at 50° C. $N^2$-[N-(N-Palmitoyl-L-alanyl)-γ-D-glutamyl]-$N^6$-(glycyl)-D,D/L,L-2,6-diaminopimelamic acid (880 mg), which melts at 198°–200° C. (to give a paste), is thus obtained.

Rf=0.28 [silica gel; n-butanol/pyridine/acetic acid/water (50/20/6/24 by volume)].

Analysis: calculated %=C, 57.87; H, 8.83; N, 12.27; found=C, 54.64; H, 8.76; N, 10.98.

Sulphuric ash %=4.7.

After total hydrolysis, analysis on a Technicon autoanalyser shows the presence of the following aminoacids:

Ala 1.00 (theory=1)
Dap 1.02 (theory=1)
Glu 1.05 (theory=1)
Gly 1.00 (theory=1)

$N^2$-[N-(N-Palmitoyl-L-alanyl)-γ-D-glutamyl]-D,D/L,L-2,6-diaminopimelamic acid can be prepared in the following manner:

$N^2$-[$O^1$-Benzyl-N-(N-palmitoyl-L-alanyl)-γ-D-glutamyl]-$N^6$-benzyloxycarbonyl-D,D/L,L-2,6-diaminopimelamic acid (2.14 g) is dissolved in acetic acid (80 cc). Palladium-on-charcoal (containing 3% of palladium) (2.14 g) is added and a slow stream of hydrogen is then passed through the mixture for 2½ hours. After filtration, the filtrate is concentrated to about 5 cc under reduced pressure (20 mm Hg) at 50° C. and is then diluted by adding ether (100 cc). This yields a precipitate which is filtered off, washed twice with ether (20 cc in total) and dried. $N^2$-[N-(N-Palmitoyl-L-alanyl)-γ-D-glutamyl]-D,D/L,L-2,6-diaminopimelamic acid (1.58 g) is thus obtained.

Rf=0.30 [silica gel; n-butanol/pyridine/acetic acid/water (50/20/6/24 by volume)].

$N^2$-[$O^1$-Benzyl-N-(N-palmitoyl-L-alanyl)-γ-D-glutamyl]-$N^6$-benzyloxycarbonyl-D,D/L,L-2,6-diaminopimelamic acid can be prepared in the following manner:

Isobutyl chloroformate (0.70 cc) is added to a solution, kept at 2° C., of benzyl N-palmitoyl-L-alanyl-α-D-glutamate (2.91 g) in tetrahydrofurane (120 cc) and triethylamine (0.75 cc). The mixture is stirred for 20 minutes at 2° C. and a solution, cooled to 2° C., of $N^6$-benzyloxycarbonyl-D,D/L,L-2,6-diaminopimelamic acid (1.726 g) in a mixture of water (53.4 cc) and 1N sodium hydroxide solution (5.34 cc) is then added. The reaction mixture is stirred for 1 hour at 2° C. and then for 18 hours at a temperature of the order of 20° C. The tetrahydrofurane is evaporated off under reduced pressure (20 mm Hg) at 50° C. The concentrate is diluted by adding water (50 cc) and acidified to pH 1 by adding 1N hydrochloric acid (10 cc). The resulting white precipitate is filtered off, washed 3 times with water (75 cc in total) and dried. This yields a white solid (4.15 g) which is chromatographed on a column of diameter 3 cm, containing neutral silica gel (0.04–0.063 mm) (85 g). To do this, the product is dissolved in acetic acid at 60° C. Neutral silica gel (10 g) is added to the resulting solution and the mixture is then concentrated to dryness under reduced pressure (20 mm Hg) at 50° C. The residue thus obtained is introduced onto the column and elution is carried out successively with ethyl acetate (320 cc), a mixture of ethyl acetate and acetic acid (9/1 by volume) (360 cc) and a mixture of ethyl acetate and acetic acid (8/2 by volume) (320 cc), 40 cc fractions being collected. Fractions 14 to 22 are combined and concentrated to dryness under reduced pressure (20 mm Hg) at 50° C.

The resulting residue is triturated in ether (50 cc), filtered off and dried. $N^2$-[$O^1$-Benzyl-N-(N-palmitoyl-L-alanyl)-γ-D-glutamyl]-$N^6$-benzyloxycarbonyl-D,D/L,L-2,6-diaminopimelamic acid (2.20 g) is thus obtained.

Rf=0.75 [silica gel; ethyl acetate/acetic acid (3/1 by volume)].

Benzyl N-palmitoyl-L-alanyl-α-D-glutamate can be prepared in the following manner:

Isobutyl chloroformate (3.6 cc) is added to a solution, kept at 0° C., of palmitic acid (7.03 g) in tetrahydrofurane (140 cc) and triethylamine (3.8 cc). The mixture is stirred for 20 minutes at 0° C. and a solution, cooled to 0° C., of benzyl L-alanyl-α-D-glutamate hydrochloride (9.45 g) in a mixture of 1N sodium hydroxide solution (54.8 cc) and water (30 cc) is then added. The reaction mixture is stirred for 1 hour at 0° C. and then for 18 hours at about 20° C.; it is then acidified to pH 1 by adding 1N hydrochloric acid (70 cc). The precipitate formed is filtered off, washed 5 times with water (200 cc in total) and dried. This yields a white powder (12.11 g) which is chromatographed on a column of diameter 2.5 cm, containing neutral silica gel (0.063–0.20 mm) (200 g). Elution is carried out successively with ethyl acetate (200 cc), a mixture of ethyl acetate and methanol (9/1 by volume) (300 cc), a mixture of ethyl acetate and methanol (8/2 by volume) (1.6 liters) and a mixture of ethyl acetate and methanol (6/4 by volume) (400 cc), 100 cc fractions being collected. Fractions 5 to 23 are combined and concentrated to dryness under reduced pressure (20 mm Hg) at 45° C. This yields a solid (5.18 g) which is triturated in boiling ether (50 cc) for ½ hour. After cooling to a temperature of the order of 20° C., the insoluble material is filtered off, washed 3 times with ether (75 cc in total) and then dried. Benzyl N-palmitoyl-L-alanyl-α-D-glutamate (2.94 g) is then obtained.

Rf=0.77 [silica gel; ethyl acetate].

EXAMPLE 13

Isobutyl chloroformate (0.46 cc) is added to a solution, kept at −7° C., of N-benzyloxycarbonylglycine (738 mg) in tetrahydrofurane (65 cc) and triethylamine (0.494 cc). The mixture is stirred for 20 minutes at −7° C. and a solution, cooled to 2° C., of $N^2$-[N-(N-lauroyl-L-alanyl)-γ-D-glutamyl]-D,D/L,L-2,6-diaminopimelamic acid (2.02 g) in water (10 cc) and 1N sodium hydroxide solution (7.06 cc) is then added. The reaction mixture is stirred for 1 hour at about −5° C. and for 18 hours at about 20° C. The tetrahydrofurane is then evaporated off under reduced pressure (20 mm Hg) at 50° C. The remaining aqueous phase is diluted by adding water (50 cc) and acidified to pH 1 by adding 1N hydrochloric acid (10 cc). The precipitate formed is filtered off, washed with water (25 cc) and dried. The resulting residue is dissolved in acetic acid (5 cc). Silica (10 g) is added and the mixture is then concentrated to dryness under reduced pressure (20 mm Hg) at 50° C. The resulting residue is introduced onto a column of diameter 35 mm, containing neutral silica gel (0.04–0.063 mm) (100 g). Elution is carried out successively with ethyl acetate (160 cc), a mixture of ethyl acetate and acetic acid (9/1 by volume) (200 cc), a mixture of ethyl acetate and acetic acid (8/2 by volume) (360 cc), a mixture of ethyl acetate and acetic acid (7/3 by volume) (200 cc), a mixture of ethyl acetate and acetic acid (6/4 by volume) (240 cc) and a mixture of ethyl acetate and acetic acid (1/1 by volume) (440 cc), 40 cc fractions being collected. Fractions 23 to 32 are combined and concentrated to dryness under reduced pressure (20 mm Hg) at 50° C. The residual oil is triturated in ether (50 cc) until all the product has been converted to powder. The product is filtered off and dried. $N^2$-[N-(N-Lauroyl-L-alanyl)-γ-D-glutamyl]-$N^6$-(benzyloxycarbonylglycyl)-D,D/L,L-2,6-diaminopimelamic acid (1.7 g) is thus obtained in the form of a white powder which melts at 134°–136° C. (to give a paste).

Rf=0.76 [silica gel; ethyl acetate/acetic acid (1/1 by volume)].

Analysis: calculated %=C, 58.25; H, 7.66; N, 11.02; found=C, 55.7; H, 7.6; N, 10.2.

After total hydrolysis, analysis on a Technicon autoanalyser shows the presence of the following amino-acids:

Ala 1.00 (theory=1)
Dap 0.93 (theory=1)
Glu 1.02 (theory=1)
Gly 1.00 (theory=1)

$N^2$-[N-(N-Lauroyl-L-alanyl)-γ-D-glutamyl]-$N^6$-(benzyloxycarbonylglycyl)-D,D/L,L-2,6-diaminopimelamic acid (1.7 g) is dissolved in acetic acid (45 cc). Palladium-on-charcoal (containing 3% of palladium) (1.7 g) is added and a slow stream of hydrogen is passed through the mixture for 3 hours. After filtering and concentrating the filtrate to dryness under reduced pressure (20 mm Hg) at 50° C., the resulting residue is triturated in ether (50 cc), filtered off, washed with ether (10 cc) and dried under reduced pressure (0.2 mm Hg) at 50° C. $N^2$-[N-(N-Lauroyl-L-alanyl)-γ-D-glutamyl]-$N^6$-(glycyl)-D,D/L,L-2,6-diaminopimelamic acid (1.32 g), which melts at 180°–184° C. (to give a paste), is thus obtained.

Rf=0.23 [silica gel; n-butanol/pyridine/acetic acid/water (50/20/6/24 by volume)].

Analysis: calculated %=C, 55.40; H, 8.74; N. 13.36; found=C, 54.31; H, 7.96; N, 12.55.

After total hydrolysis, analysis on a Technicon autoanalyser shows the presence of the following amino-acids:

Ala 0.99 (theory=1)
Dap 0.96 (theory=1)
Glu 1.01 (theory=1)
Gly 1.00 (theory=1)

EXAMPLE 14

Isobutyl chloroformate (0.52 cc) is added to a solution, kept at 12° C., of benzy N-lauroyl-L-alanyl-α-D-glutamate (1.96 g) in dioxane (80 cc) and triethylamine (0.56 cc). The solution is stirred for 20 minutes at 12° C. and a solution, cooled to 5° C., of N-ε-benzyloxycarbonylglycyl-L-lysyl-D-alanine hydrochloride (1.78 g) in a mixture of water (10 cc) and 1N sodium hydroxide solution (8 cc) is then added. The reaction mixture is stirred for 20 hours at a temperature of the order of 20° C. The reaction medium is then acidified to pH 2 by adding 1N hydrochloric acid (10 cc), and water (150 cc) is added. The insoluble material is filtered off and washed with water (100 cc). Drying yields a white powder (3.14 g) which is recrystallised from a boiling mixture of ethyl acetate (500 cc) and methanol (60 cc). After standing for 18 hours at 5° C., the crystals which have appeared are filtered off and dried. N-α-[$O^1$-Benzyl-N-(N-lauroyl-L-alanyl)-γ-D-glutamyl]-N-ε-benzyloxycarbonylglycyl-L-lysyl-D-alanine (2.26 g) which melts at 193°–196° C., is thus obtained.

Rf=0.76 [silica gel; n-butanol/pyridine/acetic acid/water (50/20/6/24 by volume)].

N-α-[$O^1$-Benzyl-N-(N-lauroyl-L-alanyl)-γ-D-glutamyl]-N-ε-benzyloxycarbonylglycyl-L-lysyl-D-alanine (2.23 g) is dissolved in methanol (250 cc) at 60° C. The solution is cooled to 40° C., palladium-on-charcoal (containing 3% of palladium) (2.23 g) is then added and a slow stream of hydrogen is passed through the mixture for 5 hours. The reaction mixture is filtered and the palladium-on-charcoal is washed 5 times with boiling methanol (300 cc in total). The combined filtrates are concentrated to dryness under reduced pressure (20 mm Hg) at 50° C. The resulting residue is triturated in ether (100 cc). After filtration, washing with ether (100 cc) and drying, N-α-[N-(N-lauroyl-L-alanyl-γ-D-glutamyl]-N-ε-glycyl-L-lysyl-D-alanine (1.31 g), which melts at 155°–158° C., is obtained.

Rf=0.48 [silica gel; methanol].

Analysis: calculated %=C, 56.69; H, 8.59; N, 12.80; found=C, 57.0; H, 9.1; N, 13.1.

After total hydrolysis, analysis on a Technicon autoanalyser shows the presence of the following aminoacids:

Ala 1.98 (theory=2)
Glu 1.06 (theory=1)
Gly 1.00 (theory=1)
Lys 1.00 (theory=1)

N-ε-Benzyloxycarbonylglycyl-L-lysyl-D-alanine hydrochloride can be prepared in the following manner:

N-α-t-Butoxycarbonyl-N-ε-benzyloxycarbonylglycyl-L-lysyl-D-alanine (3.20 g) is dissolved in a 1.7N anhydrous solution of hydrogen chloride in acetic acid (15 cc). After stirring the reaction mixture for 5 minutes, a precipitate forms. After standing for 2 hours, ether (50 cc) is added and the precipitate is filtered off, washed twice with ether (50 cc in total) and then dried. N-ε-Benzyloxycarbonylglycyl-L-lysyl-D-alanine hydrochloride (2.73 g) is thus obtained.

Rf=0.40 [silica gel; n-butanol/pyridine/acetic acid/water (50/20/6/24 by volume)].

N-α-t-Butoxycarbonyl-N-ε-benzyloxycarbonylglycyl-L-lysyl-D-alanine can be prepared in the following manner:

Isobutyl chloroformate (2.60 cc) is added to a solution, kept at 10° C., of N-benzyloxycarbonylglycine (3.54 g) in dioxane (200 cc) and triethylamine (2.8 cc). The solution is stirred for 20 minutes at about 10° C. and a solution, cooled to 10° C., of N-α-t-butoxycarbonyl-L-lysyl-D-alanine (6.35 g) in a mixture of water (40 cc) and 1N sodium hydroxide solution (20 cc) is then added. The reaction mixture is stirred for 20 hours at about 20° C. It is then acidified to pH 3 by adding 1N hydrochloric acid. The dioxane is evaporated off by concentration under reduced pressure (20 mm Hg) at 45° C. The concentrate is extracted 3 times with ethyl acetate (300 cc in total); the organic phase is washed twice with a saturated solution of citric acid (100 cc in total) and with a saturated solution of sodium chloride (20 cc) and is then concentrated to dryness under reduced pressure (20 mm Hg) at 45° C. This yields an oil (12.89 g) which is chromatographed on a column of diameter 3 cm, containing neutral silica gel (0.063–0.2 mm) (200 g). Elution is carried out with acetone, 100 cc fractions being collected. Fractions 5 and 6 are combined and concentrated to dryness under reduced pressure (20 mm Hg) at 45° C. This yields an oil (10.15 g) which is chromatographed on a column of diameter 3 cm, containing neutral silica gel (0.063–0.2 mm) (200 g). Elution is carried out successively with a mixture of cyclohexane and acetone (9/1 by volume) (100 cc), a mixture of cyclohexane and acetone (8/2 by volume) (500 cc), a mixture of cyclohexane and acetone (7/3 by volume) (500 cc), a mixture of cyclohexane and acetone (6/4 by volume) (400 cc), a mixture of cyclohexane and acetone (1/1 by volume) (500 cc), a mixture of cyclohexane and acetone (4/6 by volume) (1 liter) and acetone (200 cc), 100 cc fractions being collected. Fractions 25 to 32 are combined and concentrated to dryness under reduced pressure (20 mm Hg) at 45° C. N-α-t-Butoxycarbonyl-N-ε-benzyloxycarbonylglycyl-L-lysyl-D-alanine (3.21 g) is thus obtained.

Rf=0.69 [silica gel; n-butanol/pyridine/acetic acid/water (50/20/6/24 by volume)].

N-α-t-Butoxycarbonyl-L-lysyl-D-alanine can be prepared in the following manner:

Benzyl N-α-t-butoxycarbonyl-N-ε-benzyloxycarbonyl-L-lysyl-D-alaninate (16.23 g) is dissolved in methanol (200 cc). Palladium-on-charcoal (containing 3% of palladium) (16.23 g) is added and a slow stream of hydrogen is then passed through the mixture for 4 hours. The reaction mixture is filtered and the palladium-on-charcoal is then washed 3 times with methanol (60 cc in total). The combined filtrates are concentrated to dryness under reduced pressure (20 mm Hg) at 45° C. N-α-t-Butoxycarbonyl-L-lysyl-D-alanine (8.87 g) is thus obtained in the form of a hard foam.

Rf=0.08 [silica gel; ethyl acetate/methanol (4/1 by volume)].

EXAMPLE 15

Isobutyl chloroformate (0.5 cc) is added to a solution, kept at 13° C., of benzyl N-(N-lauroyl-L-alanyl)-α-D-glutamate (1.91 g) in dioxane (80 cc) and triethylamine (0.55 cc). The mixture is stirred for 20 minutes at 13° C. and a solution, cooled to 4° C., of $N^6$-(benzyloxycarbonylglycyl)-D,D/L,L-2,6-diaminopimelamoyl-D-alanine hydrochloride (1.90 g) in 1N sodium hydroxide solution (7.8 cc) is then added. The reaction mixture is stirred for 18 hours at about 20° C. and then acidified to pH 1 by adding 1N hydrochloric acid (10 cc) and diluted by adding water (120 cc). The precipitate formed is filtered off, washed with water (20 cc) and dried. This yields a white powder (3.21 g) which is chromatographed on a column of diameter 3 cm, containing neutral silica gel (0.04–0.063 mm) (60 g). Elution is carried out with acetic acid (40 cc) and a mixture of ethyl acetate and acetic acid (1/1 by volume) (240 cc), 20 cc fractions being collected. Fractions 5 to 10 are combined and concentrated to dryness under reduced pressure (20 mm Hg) at 45° C. This yields a white powder (2.88 g) which is chromatographed on a column of diameter 3 cm, containing neutral silica gel (0.04–0.063 mm) (60 g). Elution is carried out successively with a mixture of ethyl acetate and acetic acid (9/1 by volume) (180 cc), a mixture of ethyl acetate and acetic acid (8/2 by volume) (180 cc) and a mixture of ethyl acetate and acetic acid (6/4 by volume) (100 cc), 20 cc fractions being collected. Fractions 4 to 17 are combined and concentrated to dryness under reduced pressure (20 mm Hg) at 45° C. The resulting residue is dissolved in boiling acetic acid (25 cc) and the resulting solution, to which decolorising charcoal (0.2 g) is added, is filtered hot; the filtrate is diluted by adding ethyl acetate (100 cc). After standing for 1 hour at about 20° C., the crystals which have appeared are filtered off, washed twice with ethyl acetate (10 cc in total) and dried. $N^2$-[$O^1$-Benzyl-N-(N-lauroyl-L-alanyl)-γ-D-glutamyl]-$N^6$-(benzyloxycarbonylglycyl)-D,D/L,L-2,6-diaminopimelamoyl-D-alanine (1.53 g), which melts at 225°–227° C., is thus obtained.

Rf=0.71 [silica gel; n-butanol/pyridine/acetic acid/water (50/20/6/24 by volume)].

$N^2$-[$O^1$-Benzyl-N-(N-lauroyl-L-alanyl)-γ-D-glutamyl]-$N^6$-(benzyloxycarbonylglycyl)-D,D/L,L-2,6-diaminopimelamoyl-D-alanine (1.51 g) is dissolved in acetic acid (75 cc). Palladium-on-charcoal (containing 3% of palladium) (1.51 g) is added and a slow stream of hydrogen is then passed through the mixture for 2 hours. After filtration, ether (500 cc) is added to the filtrate. The precipitate formed is filtered off, washed with ether (50 cc) and dried under reduced pressure (0.2 mm Hg) at 20° C. This yields $N^2$-[N-(N-lauroyl-L-alanyl)-γ-D-glutamyl]-$N^6$-glycyl-D,D/L,L-2,6- diaminopimelamoyl-D-alanine (710 mg) which contains 0.4% of water (Fischer's method).

Rf=0.32 [silica gel; n-butanol/pyridine/acetic acid/water (50/20/6/24 by volume)].

Analysis: calculated %=C, 54.92; H, 8.21; N, 14.01; found=C, 52.6; H, 8.0; N, 12.3.

Sulphuric ash %=1.1.

After total hydrolysis, analysis on a Technicon autoanalyser shows the presence of the following amino-acids:

Ala 2.00 (theory=2)
Dap 0.98 (theory=1)
Glu 1.05 (theory=1)
Gly 0.95 (theory=1)

$N^6$-(Benzyloxycarbonylglycyl)-D,D/L,L-2,6-diaminopimelamoyl-D-alanine hydrochloride can be prepared in the following manner:

$N^2$-t-Butoxycarbonyl-$N^6$-(benzyloxycarbonylglycyl)-D,D/L,L-2,6-diaminopimelamoyl-D-alanine (2.21 g) is dissolved in a 1.7N anhydrous solution of hydrogen chloride in acetic acid (20 cc). The resulting solution is stirred for 2 hours at about 20° C. and ether (250 cc) is then added. The precipitate formed is separated off by decantation and triturated in acetone (100 cc). After filtration, washing with ether (25 cc) and drying, $N^6$-(benzyloxycarbonylglycyl)-D,D/L,L-2,6-diaminopimelamoyl-D-alanine hydrochloride (1.96 g) is obtained.

Rf=0.46 [silica gel; n-butanol/pyridine/acetic acid/water (50/20/6/24 by volume)].

$N^2$-t-Butoxycarbonyl-$N^6$-(benzyloxycarbonylglycyl)-D,D/L,L-2,6-diaminopimelamoyl-D-alanine can be prepared in the following manner:

Isobutyl chloroformate (0.89 cc) is added to a solution, kept at 1° C., of N-benzyloxycarbonylglycine (1.20 g) in tetrahydrofurane (68 cc) and triethylamine (0.95 cc). The mixture is stirred for 20 minutes at 1° C. and a solution, cooled to 2° C., of $N^2$-t-butoxycarbonyl-D,D/L,L-pimelamoyl-D-alanine (2.45 g) in 0.5N sodium hydroxide solution (13.6 cc) is then added. The reaction mixture is stirred for 4 hours at about 5° C. The tetrahydrofurane is then evaporated off by concentration under reduced pressure (20 mm Hg) at 45° C.; the remaining aqueous phase is diluted by adding water (50 cc), acidified to pH 3 by adding a saturated solution of citric acid and extracted 5 times with ethyl acetate (125 cc in total). The combined organic phases are washed with a saturated solution of sodium chloride (10 cc), dried over anhydrous magnesium sulphate and concentrated to dryness under reduced pressure (20 mm Hg) at 45° C. This yields a hard white foam which is chromatographed on a column of diameter 2 cm, containing neutral silica gel (0.04–0.063 mm) (90 g). Elution is carried out successively with ethyl acetate (800 cc), a mixture of ethyl acetate and methanol (9/1 by volume) (200 cc) and a mixture of ethyl acetate and methanol (1/1 by volume) (400 cc), 40 cc fractions being collected. Fractions 25 to 28 are combined and concentrated to dryness under reduced pressure (20 mm Hg) at 45° C. $N^2$-t-Butoxycarbonyl-$N^6$-(benzyloxycarbonylglycyl)-D,D/L,L-2,6-diaminopimelamoyl-D-alanine (2.4 g) is thus obtained.

Rf=0.67 [silica gel; n-butanol/pyridine/acetic acid/water (50/20/6/24 by volume)].

$N^2$-t-Butoxycarbonyl-D,D/L,L-2,6-diaminopimelamoyl-D-alanine can be prepared in the following manner:

Benzyl $N^2$-t-butoxycarbonyl-$N^6$-benzyloxycarbonyl-D,D/L,L-2,6-diaminopimelamoyl-D-alaninate (4.52 g) is dissolved in acetic acid (45 cc). Palladium-on-charcoal (containing 3% of palladium) (4.52 g) is added and a slow stream of hydrogen is then passed through the mixture for 3 hours. After filtration, the filtrate is poured into ether (800 cc); after stirring for 30 minutes, the precipitate formed is filtered off, washed with ether (100 cc) and dried. $N^2$-t-Butoxycarbonyl-D,D/L,L-2,6-diaminopimelamoyl-D-alanine (2.5 g) is thus obtained.

Rf=0.37 [silica gel; n-butanol/pyridine/acetic acid/water (50/20/6/24 by volume)].

Benzyl $N^2$-t-butoxycarbonyl-$N^6$-benzyloxycarbonyl-D,D/L,L-2,6-diaminopimelamoyl-D-alaninate can be prepared in the following manner:

Isobutyl chloroformate (1.53 cc) is added to a solution, kept at −1° C., of $N^2$-t-butoxycarbonyl-$N^6$-benzyloxycarbonyl-D,D/L,L-2,6-diaminopimelamic acid (5 g) in tetrahydrofurane (120 cc) and triethylamine (1.65 cc). The mixture is stirred for 20 minutes at −1° C. and a solution, cooled to 0° C., of benzyl D-alaninate p-toluenesulphonate (4.15 g) in tetrahydrofurane (120 cc) and triethylamine (1.65 cc) is then added. The reaction mixture is stirred for 1 hour at −1° C. and then for 18 hours at about 20° C. It is then concentrated under reduced pressure (20 mm Hg) at 45° C. The residue is taken up in ethyl acetate (100 cc). The resulting solution is washed successively with water (25 cc), 4 times with a saturated solution of sodium bicarbonate (80 cc in total), 4 times with a saturated solution of citric acid (80 cc in total) and with a saturated solution of sodium chloride (10 cc), dried over anhydrous magnesium sulphate and then concentrated to dryness under reduced pressure (20 mm Hg) at 45° C. This gives a hard pink foam (6.64 g) which is chromatographed on a column of diameter 2 cm, containing neutral silica gel (0.04–0.063 mm) (120 g). Elution is carried out successively with a mixture of ethyl acetate and cyclohexane (1/1 by volume) (40 cc), a mixture of ethyl acetate and cyclohexane (3/1 by volume) (80 cc), ethyl acetate (1.16 liters) and acetone (520 cc), 40 cc fractions being collected. Fractions 10 to 39 are combined and concentrated to dryness under reduced pressure (20 mm Hg) at 45° C. Benzyl $N^2$-t-butoxycarbonyl-$N^6$-benzyloxycarbonyl-D,D/L,L-2,6-diaminopimelamoyl-D-alaninate (4.52 g) is thus obtained.

Rf=0.37 [silica gel; ethyl acetate].

EXAMPLE 16

Isobutyl chloroformate (0.52 cc) is added to a solution, kept at 10° C., of benzyl N-docosanoyl-L-alanyl-α-D-glutamate (2.52 g) in a mixture of tetrahydrofurane (120 cc) and triethylamine (0.56 cc). The mixture is stirred for 20 minutes at 6° C. and a solution, cooled to 6° C., of N-ε-benzyloxycarbonylglycyl-L-lysine (1.484 g) in a mixture of 1N sodium hydroxide solution (4.4 cc) and water (4.4 cc) is then added. The reaction mixture is stirred for a few minutes at 6° C. and then for 2 days at about 20° C. The tetrahydrofurane is then evaporated off under reduced pressure (20 mm Hg) at 45° C.; the concentrate is acidified with 1N hydrochloric acid (10 cc). The insoluble material obtained after stirring for 1 hour is filtered off, washed 5 times with 0.1N hydrochloric acid (50 cc in total) and with water (10 cc) and then dried under reduced pressure (20 mm Hg) at 20° C. This yields a powder (5.46 g) which is dissolved in acetic acid (40 cc) containing neutral silica gel (0.04–0.063 mm) (20 g). The mixture is concentrated to dryness under reduced pressure (20 mm Hg) at 50° C. and the whole is introduced onto a column of diameter 38 mm, containing neutral silica gel (0.04–0.063 mm) (200 g). Elution is carried out successively with ethyl acetate (600 cc), a mixture of ethyl acetate and acetic acid (9/1 by volume) (440 cc), a mixture of ethyl acetate and acetic acid (8/2 by volume) (360 cc), a mixture of ethyl acetate and acetic acid (7/3 by volume) (360 cc), a mixture of ethyl acetate and acetic acid (6/4 by volume) (360 cc) and a mixture of ethyl acetate and acetic acid (1/1 by volume) (240 cc), 40 cc fractions being collected.

Fractions 26 to 57 are combined and concentrated to dryness under reduced pressure (20 mm Hg) at 45° C. The concentrate is triturated in ether (50 cc), filtered off and dried. $N^2$-[$O^1$-Benzyl-N-(N-docosanoyl-L-alanyl)-$\gamma$-D-glutamyl]-$N^6$-benzyloxycarbonylglycyl-L-lysine (1.71 g) is thus obtained.

Rf=0.76 [silica gel; n-butanol/pyridine/acetic acid/water (50/20/6/24 by volume)].

$N^2$-[$O^1$-Benzyl-N-(N-docosanoyl-L-alanyl)-$\gamma$-D-glutamyl]-$N^6$-benzyloxycarbonylglycyl-L-lysine (2.17 g) is dissolved in acetic acid (80 cc) warmed to 30° C. Palladium-on-charcoal (containing 3% of palladium) (2.17 g) is added and a slow stream of hydrogen is passed through the mixture for 2½ hours. The reaction medium is then heated to 50° C. and filtered and the insoluble material is washed 3 times with acetic acid (30 cc in total) heated to 50° C. The filtrates are combined and concentrated to dryness under reduced pressure (20 mm Hg) at 50° C. This yields a powder (1.74 g) which is chromatographed on a column of diameter 2.5 cm, containing neutral silica gel (0.04–0.063 mm) (35 g). Elution is carried out with acetic acid, 20 cc fractions being collected. Fractions 23 to 41 are combined and concentrated to dryness under reduced pressure (20 mm Hg) at 50° C. The resulting solid is taken up in ether (50 cc), triturated to a powder, filtered off and dried under reduced pressure (0.3 mm Hg). $N^2$-[N-(N-Docosanoyl-L-alanyl)-$\gamma$-D-glutamyl]-$N^6$-glycyl-L-lysine (410 mg) is thus obtained.

Rf=0.30 [silica gel; acetic acid].

Analysis=calculated % C, 62.87; H, 9.86; N, 9.64; found C, 61.5; H, 9.3; N, 9.2.

Sulphuric ash=0.5%.

After total hydrolysis, analysis on a Technicon autoanalyser shows the presence of the following aminoacids:
Ala 1.00 (theory=1)
Glu 0.95 (theory=1)
Gly 1.03 (theory=1)
Lys 1.00 (theory=1)

Benzyl N-docosanoyl-L-alanyl-$\alpha$-D-glutamate can be prepared in the following manner:

Isobutyl chloroformate (1.95 cc) is added to a solution, kept at 25° C., of docosanoic acid (5.19 g) in a mixture of tetrahydrofuran (150 cc) and triethylamine (2.1 cc). The mixture is stirred for 20 minutes at 25° C. and a solution of benzyl L-alanyl-$\alpha$-D-glutamate hydrochloride (5.69 g) in a mixture of 1N sodium hydroxide solution (33 cc) and water (17 cc) is then added. The reaction mixture is stirred for 30 minutes at about 30° C. and then for 18 hours at about 20° C. Water (100 cc) is then added and the mixture is acidified to pH 1. This yields a precipitate which is filtered off, washed 3 times with water (75 cc in total) and dried under reduced pressure (0.3 mm Hg) at 20° C. This yields a white powder (6.53 g). This powder (6 g) is dissolved in tetrahydrofurane (50 cc) containing neutral silica gel (0.04–0.063 mm) (20 g). The mixture is concentrated to dryness under reduced pressure (20 mm Hg) at 50° C. and the whole is introduced onto a column of diameter 3.5 cm, containing neutral silica gel (0.04–0.063 mm) (180 g). Elution is carried out successively with a mixture of cyclohexane and ethyl acetate (1/1 by volume) (1,300 cc), ethyl acetate (600 cc), a mixture of ethyl acetate and tetrahydrofurane (95/5 by volume) (500 cc), a mixture of ethyl acetate and tetrahydrofurane (9/1 by volume) (900 cc), a mixture of ethyl acetate and tetrahydrofurane (8/2 by volume) (800 cc), a mixture of ethyl acetate and tetrahydrofurane (6/4 by volume) (1,000 cc), a mixture of ethyl acetate and tetrahydrofurane (4/6 by volume) (900 cc), a mixture of ethyl acetate and tetrahydrofurane (2/8 by volume) (500 cc) and tetrahydrofurane (600 cc), 100 cc fractions being collected.

Fractions 17 to 68 are combined and concentrated to dryness under reduced pressure (20 mm Hg) at 50° C. This yields benzyl N-docosanoyl-L-alanyl-$\alpha$-D-glutamate (3.31 g).

Rf=0.54 [silica gel; ethyl acetate/tetrahydrofurane (8.2 by volume)].

EXAMPLE 17

Isobutyl chloroformate (0.94 cc) is added to a solution, kept at −2° C., of benzyl N-(3-cyclohexylpropionyl)-L-alanyl-$\alpha$-D-glutamate (3.23 g) in a mixture of tetrahydrofurane (200 cc) and triethylamine (1 cc). The mixture is stirred for 20 minutes at −2° C. and a solution, cooled to 2° C., of N-$\epsilon$-benzyloxycarbonylglycyl-L-lysine (2.44 g) in a mixture of 1N sodium hydroxide solution (7.23 cc) and water (7 cc) is then added. The reaction mixture is stirred for 15 minutes at −2° C. and then for 20 hours at about 20° C. It is then acidified to pH 1 by adding 1N hydrochloric acid (20 cc). The tetrahydrofurane is evaporated off by concentration under reduced pressure (20 mm Hg) at 45° C. A precipitate appears in the concentrate and is filtered off, washed 5 times with water (50 cc in total) and dried under reduced pressure (0.3 mm Hg) at 20° C. The product thus obtained (5.3 g) is dissolved in acetic acid (50 cc) containing neutral silica gel (0.04–0.063 mm) (10 g). The mixture is concentrated to dryness and the whole is introduced onto a column of diameter 2.2 cm, containing neutral silica gel (0.04–0.063 mm) (100 g). Elution is carried out successively with ethyl acetate (100 cc), a mixture of ethyl acetate and acetic acid (1/1 by volume) (700 cc) and acetic acid (1.2 liters), 100 cc fractions being collected.

Fractions 5 to 13 are combined and concentrated to dryness under reduced pressure (20 mm Hg) at 45° C. The concentrate is triturated in ether (50 cc), filtered off and dried. $N^2$-{$O^1$-Benzyl-N-[N-(3-cyclohexylpropionyl)-L-alanyl]-$\alpha$-D-glutamyl}-$N^6$-benzyloxycarbonylglycyl-L-lysine (4.21 g) is thus obtained.

Rf=0.84 [silica gel; n-butanol/pyridine/acetic acid/water (50/20/6/24 by volume)].

$N^2$-{$O^1$-Benzyl-N-[N-(3-cyclohexylpropionyl)-L-alanyl]-$\alpha$-D-glutamyl}-$N^6$-benzyloxycarbonylglycyl-L-lysine (2 g) is dissolved in acetic acid (50 cc). Palladium-on-charcoal (containing 3% of palladium) (2 g) is added and a slow stream of hydrogen is passed through the mixture for 2 hours. The catalyst is filtered off and washed 3 times with acetic acid (15 cc in total); The combined filtrates are concentrated to dryness under reduced pressure (20 mm Hg) at 50° C. This yields a powder (1.42 g) which is chromatographed on a column of diameter 2.3 cm, containing neutral silica gel (0.04–0.063 mm) (28 g). Elution is carried out successively with acetic acid (560 cc) and a mixture of n-butanol, pyridine, acetic acid and water (50/20/6/24 by volume) (120 cc), 20 cc fractions being collected. Fractions 8 to 32 are combined and concentrated to dryness under reduced pressure (20 mm Hg) at 50° C. The residue thus obtained (990 mg) is dissolved in acetic acid (30 cc) containing neutral silica gel (0.04–0.063 mm) (5 g). The mixture is concentrated to dryness under reduced pressure (20 mm Hg) at 50° C. and the whole is introduced onto a column of diameter 2.3 cm, containing neutral silica gel (0.04–0.063 mm) (20 g). Elution is carried out successively with a mixture of ethyl acetate and acetic acid (3/1 by volume) (880 cc), a mixture of ethyl acetate and acetic acid (1/1 by volume) (320 cc), a mixture of ethyl acetate and acetic acid (1/3 by volume) (240 cc) and acetic acid (440 cc), 40 cc fractions being collected. Fractions 35 to 46 are combined and concentrated to dryness under reduced pressure (20 mm Hg) at 50° C. The concentrate is triturated to a powder in ether (40 cc), filtered off and dried. $N^2$-{N-[N-(3-Cyclohexylpropionyl)-L-alanyl]-γ-D-glutamyl}-$N^6$-glycyl-L-lysine (840 mg), which melts at about 147°–150° C. (to give a paste), is thus obtained.

Rf=0.23 [silica gel. n-butanol/pyridine/acetic acid/water (50/20/6/24 by volume)].

Analysis=calculated % C, 55.44; H, 8.00; N, 12.93; found C, 53.8; H, 7.4; N, 11.8.

Sulphuric ash=1.6%.

After total hydrolysis, analysis on a Technicon autoanalyser shows the presence of the following aminoacids:

Ala 1.00 (theory=1)
Glu 0.97 (theory=1)
Gly 1.00 (theory=1)
Lys 0.98 (theory=1)

Benzyl N-(3-cyclohexylpropionyl)-L-alanyl-α-D-glutamate can be prepared in the following manner:

Isobutyl chloroformate (3 cc) is added to a solution, kept at −5° C., of 3-cyclohexanepropionic acid (3.605 g) in a mixture of tetrahydrofurane (100 cc) and triethylamine (3.23 cc). The mixture is stirred for 20 minutes at −5° C. and a solution, cooled to 5° C., of benzyl L-alanyl-α-D-glutamate hydrochloride (7.96 g) in a mixture of 1N sodium hydroxide solution (46.2 cc) and water (13.8 cc) is then added. The reaction mixture is stirred for 10 minutes at 0° C. and then for 2 days at about 20° C. The tetrahydrofurane is then evaporated off under reduced pressure (20 mm Hg) at 50° C. The concentrate is extracted twice with ether (80 cc in total) and acidified to pH 1 by adding 1N hydrochloric acid (50 cc). The oil which separates out from the reaction medium is extracted 4 times with ethyl acetate (200 cc in total). The combined ethyl acetate phases are washed with a saturated solution of sodium chloride (25 cc) and dried over anhydrous magnesium sulphate. Concentration to dryness under reduced pressure (20 mm Hg) at 50° C. yields an oil which crystallises spontaneously. These crystals (7.3 g) are dissolved in acetic acid (40 cc) containing neutral silica gel (0.04–0.063 mm) (20 g). The mixture is concentrated to dryness and the whole is introduced onto a column of diameter 2.5 cm, containing neutral silica gel (0.04–0.063 mm) (50 g). Elution is carried out with ethyl acetate, 100 cc fractions being collected. The fourth fraction is concentrated to dryness under reduced pressure (20 mm Hg) at 45° C. This yields benzyl N-(3-cyclohexylpropionyl)-L-alanyl--D-glutamate (1.86 g) which melts at 126°–128° C. Fractions 3 and 5 are combined and concentrated to dryness. The amorphous solid is chromatographed on a column of diameter 2.5 cm, containing neutral silica gel (0.04–0.063 mm) (68 g). Elution is carried out successively with a mixture of cyclohexane and ethyl acetate (1/1 by volume) (520 cc) and ethyl acetate (520 cc), 40 cc fractions being collected. Fractions 11 to 28 are combined and concentrated to dryness under reduced pressure (20 mm Hg) at 45° C. This yields benzyl N-(3-cyclohexylpropionyl)-L-alanyl-α-D-glutamate (1.37 g) which melts at 128°–130° C.

Rf=0.14 [silica gel; ethyl acetate].

EXAMPLE 18

Isobutyl chloroformate (0.468 cc) is added to a solution, kept at −3° C., of N-benzyloxycarbonylglycine (753 mg) in a mixture of tetrahydrofurane (36 cc) and triethylamine (0.5 cc). The mixture is stirred for 20 minutes at −3° C. and a solution, cooled to 0° C., of $N^2$-{N-[N-(3,5,5-trimethylhexanoyl)-L-alanyl]-γ-D-glutamyl}-D,D/L,L-2,6-diaminopimelamic acid (2.07 g) in a mixture of 1N sodium hydroxide solution (7.2 cc) and water (30 cc) is then added. The reaction mixture is stirred for 1 hour at about 0° C. and then for 20 hours at about 20° C. It is then acidified to pH 1 by adding 1N hydrochloric acid (12 cc). The tetrahydrofurane is evaporated off by concentration under reduced pressure (20 mm Hg) at 50° C. The concentrate is extracted 4 times with ethyl acetate (100 cc in total). The combined ethyl acetate phases are washed with 0.1N hydrochloric acid (25 cc) and dried over sodium sulphate. Filtration and concentration to dryness under reduced pressure (20 mm Hg) at 50° C. yields an amorphous solid (2.13 g) which is dissolved in acetic acid (20 cc) containing neutral silica gel (0.04–0.063 mm) (5 g). The mixture is concentrated to dryness under reduced pressure (20 mm Hg) at 50° C. and the whole is introduced onto a column of diameter 2 cm, containing neutral silica gel (0.04–0.063 mm) (40 g). Elution is carried out successively with a mixture of ethyl acetate and acetic acid (9/1 by volume) (400 cc), a mixture of ethyl acetate and acetic acid (8/2 by volume) (160 cc), a mixture of ethyl acetate and acetic acid (7/3 by volume) (200 cc) and a mixture of ethyl acetate and acetic acid (1/1 by volume) (200 cc), 40 cc fractions being collected. Fractions 9 to 19 are combined and concentrated to dryness under reduced pressure (20 mm Hg) at 50° C. The resulting amorphous solid is taken up in ether (40 cc), triturated until it has all been converted to powder, filtered off and dried under reduced pressure (0.3 mm Hg). $N^2$-{N-[N-(3,5,5-Trimethylhexanoyl)-L-alanyl]-γ-D-glutamyl}-$N^6$-benzyloxycarbonylglycyl-D,D/L,L-2,6-diaminopimelamic acid (1.49 g) is thus obtained.

Rf=0.70 [silica gel; acetic acid].

Rf=0.53 [silica gel; ethyl acetate/acetic acid (1/1 by volume)].

$N^2$-{N-[N-(3,5,5-Trimethylhexanoyl)-L-alanyl]-γ-D-glutamyl}-$N^6$-benzyloxycarbonylglycyl-D,D/L,L-2,6-diaminopimelamic acid (1.45 g) is dissolved in acetic acid (40 cc). Palladium-on-charcoal (containing 3% of palladium) (1.45 g) is added and a slow stream of hydrogen is passed through the mixture for 1½ hours. After filtering and concentrating the filtrate to dryness under reduced pressure (20 mm Hg) at 50° C., the amorphous solid is triturated in ether (50 cc). This yields a solid (1.18 g) which is suspended in water (150 cc). After stirring for 68 hours a clear solution is obtained and this is introduced onto a column of diameter 2.3 cm, containing Sephadex G-10 (250 g). Elution is carried out with water, 100 cc fractions being collected. Fractions 2 and 3 are combined, lyophilised and dried in vacuo (0.3 mm Hg). $N^2$-{N-[N-(3,5,5-Trimethylhexanoyl)-L-alanyl]-$\gamma$-D-glutamyl}-$N^6$-glycyl-D,D/L,L-2,6-diaminopimelamic acid (930 mg) is thus obtained.

Rf=0.23 [silica gel; n-butanol/pyridine/acetic acid/water (50/20/6/24 by volume)].

Analysis=calculated % C, 53.23; H, 7.90; N, 14.33; found C, 49.9; H, 6.5; N, 13.3.

Sulphuric ash=12.4%.

After total hydrolysis, analysis on a Technicon autoanalyser shows the presence of the following aminoacids:
Ala 1.01 (theory=1)
Dap 0.95 (theory=1)
Glu 1.00 (theory=1)
Gly 1.00 (theory=1)

$N^2$-{N-[N-(3,5,5-Trimethylhexanoyl)-L-alanyl]-$\gamma$-D-glutamyl}-D,D/L,L-2,6-diaminopimelamic acid can be prepared in the following manner:

$N^2$-{$O^1$-Benzyl-N-[N-(3,5,5-trimethylhexanoyl)-L-alanyl]-$\gamma$-D-glutamyl}-$N^6$-benzyloxycarbonyl-D,D/L,L-2,6-diaminopimelamic acid (2.76 g) is dissolved in acetic acid (100 cc). Palladium-on-charcoal (containing 3% of palladium) (2.76 g) is added and a slow stream of hydrogen is passed through the mixture for 2½ hours. After filtering and concentrating the filtrate to dryness under reduced pressure (20 mm Hg) at 50° C., the oil is triturated in ether (50 cc). This yields a precipitate which is filtered off and dried under reduced pressure (0.3 mm Hg) at 20° C. $N^2$-{N-[N-(3,5,5-Trimethylhexanoyl)-L-alanyl]-$\gamma$-D-glutamyl}-D,D/L,L-2,6-diaminopimelamic acid (2.07 g) is thus obtained.

Rf=0.32 [silica gel; n-butanol/pyridine/acetic acid/water (50/20/6/24 by volume)].

Rf=0.31 [silica gel; acetic acid].

$N^2$-{$O^1$-Benzyl-N-[N-(3,5,5-trimethylhexanoyl)-L-alanyl]-$\gamma$-D-glutamyl}-$N^6$-benzyloxycarbonyl-D,D/L,L-2,6-diaminopimelamic acid can be prepared in the following manner;

Isobutyl chloroformate (0.91 cc) is added to a solution, kept at 0° C., of benzyl N-(3,5,5-trimethylhexanoyl)-L-alanyl-$\alpha$-D-glutamate (3.14 g) in a mixture of tetrahydrofurane (150 cc) and triethylamine (0.98 cc). The mixture is stirred for 20 minutes at 0° C. and a solution, cooled to 0° C., of $N^6$-benzyloxycarbonyl-D,D/L,L-2,6-diaminopimelamic acid (2.263 g) in a mixture of 1N sodium hydroxide solution (7 cc) and water (70 cc) is then added. The reaction mixture is stirred for 1 hour at about 0° C. and then for 20 hours at about 22° C. A small amount of insoluble material is then removed by filtration and the filtrate is acidified to pH 1 by adding 1N hydrochloric acid (12 cc). The tetrahydrofurane is evaporated off under reduced pressure (20 mm Hg) at 50° C. The concentrate is extracted 3 times with ethyl acetate (150 cc in total). The combined ethyl acetate phases are washed with 0.1N hydrochloric acid (20 cc) and dried over sodium sulphate. Concentration to dryness under reduced pressure (20 mm Hg) at 50° C. yields an amorphous solid (5.14 g) which is dissolved in a mixture of ethyl acetate and acetic acid (1/1 by volume) (60 cc) containing neutral silica gel (0.04–0.063 mm) (10 g). The mixture is concentrated to dryness under reduced pressure (20 mm Hg) at 50° C. and the whole is introduced onto a column of diameter 3 cm, containing neutral silica gel (0.04–0.063 mm) (100 g). Elution is carried out successively with ethyl acetate (400 cc), a mixture of ethyl acetate and acetic acid (9/1 by volume) (200 cc), a mixture of ethyl acetate and acetic acid (8/2 by volume) (200 cc), a mixture of ethyl acetate an acetic acid (6/4 by volume) (160 cc) and a mixture of ethyl acetate and acetic acid (1/1 by volume) (240 cc), 40 cc fractions being collected. Fractions 15 to 25 are combined and concentrated to dryness under reduced pressure (20 mm Hg) at 50° C. The resulting oil is taken up in ether (50 cc) and triturated to a powder, and the powder is filtered off and dried under reduced pressure (0.3 mm Hg). $N^2$-{$O^1$-Benzyl-N-[N-(3,5,5-trimethylhexanoyl)-L-alanyl]-$\gamma$-D-glutamyl}-$N^6$-benzyloxycarbonyl-D,D/L,L-2,6-diaminopimelamic acid (2.85 g) is obtained.

Rf=0.82 [silica gel; ethyl acetate/acetic acid (3/1 by volume)].

Benzyl N-(3,5,5-trimethylhexanoyl)-L-alanyl-$\alpha$-D-glutamate can be prepared in the following manner:

Isobutyl chloroformate (4.3 cc) is added to a solution, kept at −6° C., of N-(3,5,5-trimethylhexanoyl)-L-alanine (7.59 g) in a mixture of tetrahydrofurane (400 cc) and triethylamine (4.63 cc). The mixture is stirred for 20 minutes at −6° C. and a solution, cooled to 3° C., of benzyl $\alpha$-D-glutamate hydrochloride (9.06 g) in a mixture of 1N sodium hydroxide solution (66.2 cc) and water (14 cc) is then added. The reaction mixture is stirred for 15 minutes at about −5° C. and then for 66 hours at about 18° C.; it is then acidified to pH 1 by adding 1N hydrochloric acid (75 cc). The tetrahydrofurane is evaporated off under reduced pressure (20 mm Hg) at 50° C. The concentrate is extracted 5 times with ethyl acetate (200 cc in total). The combined ethyl acetate phases are washed with 0.1N hydrochloric acid (40 cc) and dried over magnesium sulphate. Filtration and concentration to dryness under reduced pressure (20 mm Hg) at 50° C. yields an oil (14.8 g) which is dissolved in ethyl acetate (50 cc) containing neutral silica gel (0.04–0.063 mm) (30 g). The mixture is concentrated to dryness under reduced pressure (20 mm Hg) at 50° C. and the whole is introduced onto a column of diameter 2.8 cm, containing neutral silica gel (0.04–0.063 mm) (280 g). Elution is carried out successively with cyclohexane (2 liters), a mixture of cyclohexane and ethyl acetate (95/5 by volume) (1 liter), a mixture of cyclohexane and ethyl acetate (90/10 by volume) (1.5 liters), a mixture of cyclohexane and ethyl acetate (80/20 by volume) (5 liters), a mixture of cyclohexane and ethyl acetate (70/30 by volume) (1.5 liters) and a mixture of cyclohexane and ethyl acetate (50/50 by volume (3.5 liters), 500 cc fractions being collected. Fractions 23 to 29 are combined and concentrated to dryness under reduced pressure (20 mm Hg) at 50° C. Benzyl N-(3,5,5-trimethylhexanoyl)-L-alanyl-$\alpha$-D-glutamate (10.86 g) is thus obtained in the form of an oil which crystallises.

Rf=0.37 [silica gel; ethyl acetate].

N-(3,5,5-Trimethylhexanoyl)-L-alanine can be prepared in the following manner:

Isobutyl chloroformate (6.5 cc) is added to a solution, kept at −5° C., of 3,5,5-trimethylhexanoic acid (7.912 g) in a mixture of tetrahydrofurane (125 cc) and triethylamine (7 cc). The mixture is stirred for 20 minutes −5° C. and a solution, cooled to 5° C., of L-alanine (4.495 g) in 1N sodium hydroxide solution (50 cc) is then added. The reaction mixture is stirred for 10 minutes at about 0° C. and then for 18 hours at about 25° C. The tetrahydrofurane is then evaporated off under reduced pressure (20 mm Hg) at 50° C. The concentrate is extracted twice with ether (40 cc in total) and acidified to pH 1 by adding 1N hydrochloric acid (55 cc). The oily precipitate which forms is extracted 5 times with ethyl acetate (250 cc in total). The ethyl acetate phases are combined, washed with a saturated solution of sodium chloride (25 cc) and dried over magnesium sulphate. Filtration and concentration to dryness under reduced pressure (20 mm Hg) at 50° C. yields an oil (11.79 g) which is dissolved in ethyl acetate (40 cc) containing neutral silica gel (0.063–0.20 mm) (20 g). The mixture is concentrated to dryness under reduced pressure (20 mm Hg) at 50° C. and the whole is introduced onto a column of diameter 3 cm, containing neutral silica gel (0.063–0.20 mm) (120 g). Elution is carried out successively with cyclohexane (600 cc), a mixture of cyclohexane and ethyl acetate (95/5 by volume) (300 cc), a mixture of cyclohexane and ethyl acetate (90/10 by volume) (300 cc), a mixture of cyclohexane and ethyl acetate (80/20 by volume) (300 cc), a mixture of cyclohexane and ethyl acetate (50/50 by volume) (700 cc), ethyl acetate (300 cc) and a mixture of ethyl acetate and methanol (90/10 by volume) (300 cc), 100 cc fractions being collected. Fractions 17 to 28 are combined and concentrated to dryness under reduced pressure (20 mm Hg) at 45° C. This yields an oil (10.16 g) which is dissolved in ether (25 cc). The addition of petroleum ether (150 cc) yields an oil which is separated off by decantation. After drying in vacuo (0.2 mm Hg), N-(3,5,5-trimethylhexanoyl)-L-alanine (7.59 g) is obtained.

Rf=0.43 [silica gel; ethyl acetate].

EXAMPLE 19

Isobutyl chloroformate (0.91 cc) is added to a solution, kept at 0° C., of benzyl N-(3,5,5-trimethylhexanoyl)-L-alanyl-α-D-glutamate (3.14 g) in a mixture of tetrahydrofurane (150 cc) and triethylamine (0.98 cc). The mixture is stirred for 20 minutes at −2° C. and a solution, cooled to 2° C., of N-ε-benzyloxycarbonylglycyl-L-lysine (2.36 g) in a mixture of 1N sodium hydroxide solution (7 cc) and water (20 cc) is then added. The reaction mixture is stirred for 1 hour at about 0° C. and then for 20 hours at about 20° C. It is then acidified to pH 1 by adding 1N hydrochloric acid (12 cc). The tetrahydrofurane is evaporated off under reduced pressure (20 mm Hg) at 50° C. The concentrate is extracted 5 times with ethyl acetate (125 cc in total). The combined ethyl acetate phases are washed with 0.1N hydrochloric acid (25 cc) and dried over sodium sulphate. Filtration and concentration to dryness under reduced pressure (20 mm Hg) at 50° C. yields an amorphous solid (4.41 g) which is dissolved in ethyl acetate (50 cc) containing neutral silica gel (0.04–0.063 mm) (15 g). The mixture is concentrated to dryness under reduced pressure (20 mm Hg) at 20° C. and the whole is introduced onto a column of diameter 3.5 cm, containing neutral silica gel (0.04–0.63 mm) (100 g). Elution is carried out successively with ethyl acetate (480 cc), a mixture of ethyl acetate and acetic acid (95/5 by volume) (160 cc) and a mixture of ethyl acetate and acetic acid (9/1 by volume) (440 cc), 40 cc fractions being collected. Fractions 16 to 46 are combined and concentrated to dryness under reduced pressure (20 mm Hg) at 50° C. N-α-{O¹-Benzyl-N-[N-(3,5,5-trimethylhexanoyl)-L-alanyl]-γ-D-glutamyl}-N-ε-benzyloxycarbonylglycyl-L-lysine (4.38 g) is thus obtained in the form of an oil.

Rf=0.84 [silica gel; ethyl acetate/acetic acid (3/1 by volume)].

N-α-{O¹-Benzyl-N-[N-(3,5,5-trimethylhexanoyl)-L-alanyl]-γ-D-glutamyl}-N-ε-benzyloxycarbonylglycyl-L-lysine (2.14 g) is dissolved in acetic acid (100 cc). Palladium-on-charcoal (containing 3% of palladium) (2.14 g) is added and a slow stream of hydrogen is passed through the mixture for 1 hour 40 minutes. After filtering and concentrating the filtrate to dryness under reduced pressure (20 mm Hg) at 50° C., the amorphous solid is triturated in ether (50 cc). This yields a precipitate which is filtered off and dried under reduced pressure (0.3 mm Hg) at 20° C. N-α-{N-[N-(3,5,5-Trimethylhexanoyl)-L-alanyl]-γ-D-glutamyl}-N-ε-glycyl-L-lysine (1.11 g) is thus obtained.

Rf=0.37 [silica gel; acetic acid].

Rf=0.28 [silica gel; n-butanol/pyridine/acetic acid/water (50/20/6/24 by volume)].

Analysis=calculated % C, 55.23; H, 8.35; N, 12.88; found C, 52.2; H, 7.7; N, 11.9.

Sulphuric ash=2%.

After total hydrolysis, analysis on a Technicon autoanalyser shows the presence of the following aminoacids:

Ala 1.00 (theory=1)
Glu 0.94 (theory=1)
Gly 1.02 (theory=1)
Lys 1.02 (theory=1)

EXAMPLE 20

Isobutyl chloroformate (1.26 cc) is added to a solution, kept at 10° C., of nonanoic acid (1.52 g) in a mixture of dioxane (120 cc) and triethylamine (1.35 cc). The mixture is stirred for 20 minutes at 10° C. and a solution, cooled to 10° C., of N-α-[O¹-benzyl-N-L-alanyl-γ-D-glutamyl]N-ε-(benzyloxycarbonylglycyl)-L-lysine hydrochloride (3.5 g) in a mixture of 1N sodium hydroxide solution (9.6 cc) and water (10 cc) is then added. The reaction mixture is stirred for a few minutes at about 10° C. and then for 15 minutes at about 20° C. The reaction medium is then concentrated under reduced pressure (20 mm Hg) at 45° C. Water (160 cc) is added to the concentrate and the mixture is acidified to pH 2 by adding 1N hydrochloric acid (5 cc). Extraction is carried out 3 times with ethyl acetate (150 cc in total). The combined ethyl acetate phases are washed with a saturated solution of sodium chloride (100 cc), dried over magnesium sulphate and concentrated to dryness under reduced pressure (20 mm Hg) at 45° C. The gelatinous mixture thus obtained is taken up in ether (100 cc) and triturated until it has all been converted to powder, and the powder is filtered off, washed 4 times with ether (200 cc in total) and dried in the atmosphere. This yields a white powder (2.2 g) which is dissolved in acetic acid (30 cc) containing neutral silica gel (0.04–0.063 mm) (4 g). The mixture is concentrated to dryness under reduced pressure (20 mm Hg) at 50° C. and the whole is introduced onto a column of diameter 3 cm, containing neutral silica gel (0.04–0.063 mm) (100 g). Elution is carried out with a mixture of ethyl acetate and acetic acid (9/1 by volume), 50 cc fractions being collected. Fractions 8 to 22 are combined and concentrated to dryness under reduced pressure (20 mm Hg) at 50° C. The resulting oil is taken up in ether (100 cc) and triturated until it has all been converted to powder, and the powder is filtered off and dried under reduced pressure (0.3 mm Hg) at 50° C. N-α-[O¹-Benzyl-N-(N-nonanoyl-L-alanyl)-γ-D-glutamyl]-N-ε-(benzyloxycarbonylglycyl)-L-lysine (1.3 g) is thus obtained.

Rf=0.74 [silica gel; n-butanol/pyridine/acetic acid/water (50/20/6/24 by volume)].

Hydrogen bromide is bubbled through a solution of N-α-[O$^1$-benzyl-N-(N-nonanoyl-L-alanyl)-γ-D-glutamyl]-N-ε-(benzyloxycarbonylglycyl)-L-lysine (1.2 g) in trifluoroacetic acid (100 cc) for 90 minutes. The solution is then concentrated to dryness under reduced pressure (20 mm Hg) at 50° C., This yields an oil which is taken up in ethyl acetate (50 cc) and triturated until it has all been converted to powder, and the powder is filtered off, washed 3 times with ether (150 cc in total) and dried under reduced pressure (0.3 mm Hg) at 20° C. This yields a powder (0.9 g) which is chromatographed on a column of diameter 2.5 cm, containing neutral silica gel (0.04–0.063 mm) (50 g). Elution is carried out with a mixture of ethyl acetate and acetic acid (1/1 by volume), 50 cc fractions being collected. Fractions 21 to 57 are combined and concentrated to dryness under reduced pressure (20 mm Hg) at 50° C. This yields an oil which is taken up in ethyl acetate (50 cc) and triturated until it has all been converted to powder, and the powder is filtered off, washed twice with ether (60 cc in total) and dried under reduced pressure (0.3 mm Hg) at 20° C. N-α-[N-(N-Nonanoyl-L-alanyl)-γ-D-glutamyl]-N-ε-glycyl-L-lysine hydrobromide (0.49 g) is thus obtained.

Rf=0.30 [silica gel; n-butanol/pyridine/acetic acid/water (50/20/6/24 by volume)].

Analysis=calculated % C, 48.07; H, 7.42; N, 11.21; found C, 45.3; H, 7.3; N, 10.5.

Sulphuric ash=5.1%.

After total hydrolysis, analysis on a Technicon antoanalyser shows the presence of the following amino-acids:

Ala 1.00 (theory=1)
Glu 1.03 (theory=1)
Gly 1.00 (theory=1)
Lys 1.04 (theory=1)

N-α-[O$^1$-Benzyl-N-L-alanyl-γ-D-glutamyl]-N-ε-(benzyloxycarbonylglycyl)-L-lysine hydrochloride can be prepared in the following manner:

N-α-[O$^1$-Benzyl-N-t-butoxycarbonyl-L-alanyl-γ-D-glutamyl]-N-ε-(benzyloxycarbonylglycyl)-L-lysine (3.5 g) is dissolved in a saturated anhydrous solution of hydrogen chloride in acetic acid (20 cc). The reactants are left in contact for 1 hour at 20° C. and the solution is then run into ether (1 liter). This yields a precipitate which is filtered off, washed twice with ether (200 cc in total) and dried under reduced pressure (20 mm Hg) at 20° C. N-α-[O$^1$-Benzyl-N-L-alanyl-γ-D-glutamyl]-N-ε-(benzyloxycarbonylglycyl)-L-lysine hydrochloride (3.5 g) is thus obtained.

EXAMPLE 21

Isobutyl chloroformate (0.27 cc) is added to a solution, kept at −4° C., of N-benzyloxycarbonylglycine (425 mg) in a mixture of tetrahydrofurane (40 cc) and triethylamine (0.28 cc). The mixture is stirred for 20 minutes at −4° C. and a solution, cooled to 0° C., of N$^2$-[N-(N-lauroyl-L-alanyl)-γ-D-glutamyl]-L,L-2,6-diaminopimelamic acid (1.16 g) in a mixture of 1N sodium hydroxide solution (4 cc) and water (6 cc) is then added. The reaction mixture is stirred for 15 minutes at about −5° C. and then for 20 hours at about 20° C. A slight turbidity is then eliminated by filtration and the filtrate is concentrated under reduced pressure (20 mm Hg) at 45° C.; water (30 cc) is added to the concentrate. A precipitate forms slowly. It is filtered off, washed with water (20 cc) and dried in the atmosphere. This yields a cream powder (1.38 g) which is chromatographed on neutral silica gel (0.04–0.063 mm) (70 g) contained in a column of diameter 2.8 cm. Elution is carried out successively with ethyl acetate (250 cc), a mixture of ethyl acetate and acetic acid (95/5 by volume) (950 cc), a mixture of ethyl acetate and acetic acid (9/1 by volume) (800 cc), a mixture of ethyl acetate and acetic acid (8/2 by volume) (800 cc) and a mixture of ethyl acetate and acetic acid (7/3 by volume) (350 cc), 50 cc fractions being collected. Fractions 38 to 62 are combined and concentrated to dryness under reduced pressure (20 mm Hg) at 50° C. The resulting oil is taken up in ether (100 cc) and triturated until it has all been converted to powder, and the powder is filtered off and dried under reduced pressure (0.3 mm Hg) at 40° C. N$^2$-[N-(N-Lauroyl-L-alanyl)-γ-D-glutamyl]-N$^6$-benzyloxycarbonylglycyl-L,L-2,6-diaminopimelamic acid (1.03 g) is thus obtained.

Rf=0.54 [silica gel; ethyl acetate/acetic acid (1/1 by volume)].

N$^2$-[N-(N-Lauroyl-L-alanyl)-γ-D-glutamyl]-N$^6$-benzyloxycarbonylglycyl-L,L-2,6-diaminopimelamic acid (1.18 g) is dissolved in acetic acid (32 cc). Palladium-on-charcoal (containing 3% of palladium) (1.18 g) is added and a slow stream of hydrogen is passed through the mixture for 5 hours. After filtering and concentrating the filtrate to dryness under reduced pressure (20 mm Hg) at 50° C., the resulting amorphous product is triturated in ethyl acetate (30 cc), filtered off and washed twice with ethyl acetate (40 cc in total) and with ether (20 cc). This yields a cream powder (0.88 g) which is dissolved in acetic acid (20 cc) containing neutral silica gel (0.04–0.063 mm) (1.6 g). The mixture is concentrated to dryness under reduced pressure (20 mm Hg) at 50° C. and the whole is introduced onto a column of diameter 1.8 cm, containing neutral silica gel (0.04–0.063 mm) (16 g). Elution is carried out successively with a mixture of ethyl acetate and acetic acid (1/1 by volume) (650 cc) and a mixture of ethyl acetate and acetic acid (1/3 by volume) (1.4 liters), 50 cc fractions being collected. Fractions 15 to 30 are combined and concentrated to dryness under reduced pressure (20 mm Hg) at 50° C. The amorphous product thus obtained is taken up in ethyl acetate (50 cc), filtered off and washed twice with ethyl acetate (40 cc in total) and then with ether (30 cc). After drying under reduced pressure (0.3 mm Hg) at 40° C., N$^2$-[N-(N-lauroyl-L-alanyl)-γ-D-glutamyl]-N$^6$-glycyl-L,L-2,6-diaminopimelamic acid (0.44 g) is obtained.

Rf=0.30 [silica gel; n-butanol/pyridine/acetic acid/water (50/20/6/24 by volume)].

Analysis=calculated % C, 55.40; H, 8.34; N, 13.36; found C, 53.0; H, 8.3; N, 12.6.

Sulphuric ash=3.2%.

After total hydrolysis, analysis on a Techniconautoanalyser shows the presence of the following amino-acids:

Ala 1.04 (theory=1)
Dap 0.98 (theory=1)
Glu 1.00 (theory=1)
Gly 1.00 (theory=1)

N$^2$-[N-(N-Lauroyl-L-alanyl)-γ-D-glutamyl]-L,L-2,6-diaminopimelamic acid can be prepared in the following manner:

N$^2$-[O$^1$-Benzyl-N-(N-lauroyl-L-alanyl)-γ-D-glutamyl]-N$^6$-benzyloxycarbonyl-L,L-2,6-diaminopimelamic acid (1.36 g) is dissolved in acetic acid (40 cc). Palladium-on-charcoal (containing 3% of palladium) (1.4 g) is added and a slow stream of hydrogen is passed through the mixture for 4 hours. After filtering and concentrating the filtrate to dryness under reduced pressure (20 mm Hg) at 55° C., the resulting oil is taken up in ether (100 cc) and triturated until it has all been converted to powder, and the powder is filtered off and dried in air. $N^2$-[N-(N-Lauroyl-L-alanyl)-$\gamma$-D-glutamyl]-L,L-2,6-diaminopimelamic acid (0.96 g) is thus obtained.

Rf=0.38 [silica gel; n-butanol/pyridine/acetic acid/water (50/20/6/24 by volume)].

$N^2$-[$O^1$-Benzyl-N-(N-lauroyl-L-alanyl)-$\gamma$-D-glutamyl]-$N^6$-benzyloxycarbonyl-L,L-2,6-diaminopimelamic acid can be prepared in the following manner:

Isobutyl chloroformate (0.69 cc) is added to a solution, kept at $-5°$ C., of benzyl N-lauroyl-L-alanyl-$\alpha$-D-glutamate (2.57 g) in a mixture of tetrahydrofurane (120 cc) and triethylamine (0.74 cc). The mixture is stirred for 20 minutes at $-5°$ C. and a solution, cooled to 0° C., of $N^6$-benzyloxycarbonyl-L,L-2,6-diaminopimelamic acid (1.7 g) in a mixture of 1N sodium hydroxide solution (5.25 cc) and water (35 cc) is then added. The reaction mixture is stirred for 20 minutes at about $-3°$ C. and then for 22 hours at about 20° C. It is then acidified to pH 2 by adding 1N hydrochloric acid (20 cc). The precipitate formed is filtered off and washed 3 times with 0.1N hydrochloric acid (60 cc in total) and 3 times with water (60 cc in total). Drying in the atmosphere yields a white powder (3.97 g) which is chromatographed on neutral silica gel (0.04–0.063 mm) (200 g) contained in a column of diameter 3.8 cm.

Elution is carried out successively with ethyl acetate (600 cc), a mixture of ethyl acetate and acetic acid (95/5 by volume) (500 cc) and a mixture of ethyl acetate and acetic acid (9/1 by volume) (800 cc), 50 cc fractions being collected. Fractions 24 to 30 are combined and concentrated to dryness under reduced pressure (20 mm Hg) at 50° C. The resulting oil is taken up in either (100 cc) and triturated until it has all been converted to powder, and the powder is filtered off and dried under reduced pressure (0.3 mm Hg). $N^2$-[$O^1$-Benzyl-N-(N-lauroyl-L-alanyl]-$\gamma$-D-glutamyl]-$N^6$-benzyloxycarbonyl-L,L-2,6-diaminopimelamic acid (1.24 g) is thus obtained.

Rf=0.85 [silica gel; n-butanol/pyridine/acetic acid/water (50/20/6/24 by volume)].

Rf=0.76 [silica gel; ethyl acetate/acetic acid (3/1 by volume)].

$N^6$-Benzyloxycarbonyl-L,L-2,6-diaminopimelamic acid can be prepared in the following manner:

Cupric bromide (2.14 g) dissolved in water (20 cc) is added to a solution of L,L-2,6-diaminopimelamic acid dihydrochloride (5 g) in water (15 cc), brought to pH 10 by adding 1N sodium hydroxide solution (45 cc). The reaction mixture is stirred for 2 hours at about 20° C. A small amount of insoluble material is filtered off and the filtrate is then cooled to a temperature between $-3°$ C. and 0° C. Sodium bicarbonate (4.8 g) is added and benzyl chloroformate (4.1 cc) is then added dropwise in the course of 30 minutes. The reaction mixture is stirred for 18 hours at a temperature of the order of 20° C. The blue precipitate formed is filtered off and washed 3 times with water (90 cc in total), 3 times with ethanol (90 cc in total) and 3 times with ether (90 cc in total). Drying under reduced pressure (20 mm Hg) at 50° C. yields the copper complex of $N^6$-benzyloxycarbonyl-L,L-2,6-diaminopimelamic acid (4.18 g) which is added to 1N hydrochloric acid (28 cc). The mixture is stirred for 1 hour at a temperature of the order of 20° C. An insoluble material is filtered off. Methanol (14 cc) is added to the filtrate and a stream of hydrogen sulphide is then passed through the mixture for 6 hours. The mixture is left to stand for 16 hours. The resulting black slurry is filtered and the solid is washed 3 times with water (15 cc in total). The combined filtrates are concentrated to a volume of 10 cc under reduced pressure (20 mm Hg) at 50° C., brought to pH 7 by adding triethylamine (5 cc) and brought to pH 6.8 by adding 1N hydrochloric acid (5 cc). The white slurry thus obtained is kept at 0° C. for 2 hours. The product is filtered off and washed successively 3 times with water (30 cc in total), 3 times with ethanol (30 cc in total) and 3 times with ether (30 cc in total). After drying at 60° C. under reduced pressure (0.3 mm Hg), $N^6$-benzyloxycarbonyl-L,L-2,6-diaminopimelamic acid (1.78 g) is obtained.

$[\alpha]_D^{20°} = +11°$ (c=1, 1N HCl).

Rf=0.45 [silica gel; n-butanol/pyridine/acetic acid/water (50/20/6/24 by volume)].

L,L-2,6-Diaminopimelamic acid dihydrochloride can be prepared in the following manner:

L,L-2,6-Dibenzyloxycarbonylaminopimelamic acid (17 g) is dissolved in a mixture of methanol (300 cc) and concentrated hydrochloric acid (d=1.19) (5.9 cc). Palladium-on-charcoal (containing 3% of palladium) (17 g) is added and a stream of hydrogen is passed through the mixture for 4 hours. After filtering and concentrating the filtrate to dryness under reduced pressure (20 mm Hg) at 55° C., L,L-2,6-diaminopimelamic acid dihydrochloride (8.8 g) is obtained in the form of a hard foam.

L,L-2,6-Dibenzyloxycarbonylaminopimelamic acid can be prepared in the following maner:

Benzyl acid L,L-$N^2$,$N^6$-dibenzyloxycarbonyl-2,6-diaminopimelate (19 g) is dissolved in methanol (190 cc). This solution is cooled to about 0° C. and saturated with ammonia. As soon as it is saturated, it is transferred into a 1 liter autoclave. After this autoclave has been closed, it is kept for 6 days at about 20° C. After degassing, the solution thus obtained is concentrated under reduced pressure (20 mm Hg) at 50° C. The residue is dissolved in water (250 cc) and the resulting solution is brought to pH 2 by adding 4N hydrochloric acid (30 cc) and extracted 3 times with ethyl acetate (300 cc in total); this organic phase is washed with a saturated solution of sodium chloride (100 cc), dried over sodium sulphate and concentrated to dryness under reduced pressure (20 mm Hg) at 50° C. L,L-2,6-Dibenzyloxycarbonylaminopimelamic acid (17 g) is thus obtained in the form of an oil.

Rf=0.68 [silica gel; n-butanol/pyridine/acetic acid/water (50/20/6/24 by volume)].

Benzyl acid L,L-$N^2$,$N^6$-dibenzyloxycarbonyl-2,6-diaminopimelate can be prepared in the following manner:

Dibenzyl L,L-$N^2$,$N^6$-dibenzyloxycarbonyl-2,6-diaminopimelate (55 g) is dissolved in benzyl alcohol (400 cc) warmed to 40° C. A solution of 86% pure potassium hydroxide pellets (4.8 g) in benzyl alcohol (400 cc) is then run, in the course of 6½ hours, into this solution, kept at 40° C. for about 1 hour. The reaction medium is stirred at about 20° C. for a further 16 hours and then concentrated to dryness under reduced pressure (0.5 mm Hg) at 90° C. This yields an oil which is dissolved in water (1 liter) and the solution is extracted 3 times with ethyl acetate (900 cc in total). The aqueous phase extracted in this way is acidified to pH 2 by adding 4N hydrochloric acid (45 cc) and extracted 3 times with ethyl acetate (1.5 liters in total). The ethyl acetate phase thus obtained is washed with a saturated solution of sodium chloride (500 cc) and dried over anhydrous sodium sulphate. After filtering off the sodium sulphate, dicyclohexylamine (17 cc) is added and the mixture is concentrated to dryness under reduced pressure (20 mm Hg) at 40° C. This yields a yellow oil which is dissolved in ethanol (100 cc) to which water (100 cc) is added. After standing for 20 hours at 0° C., a white solid is obtained and this is filtered off, washed twice with water (100 cc in total) and taken up in a mixture of ethyl acetate (200 cc) and water (200 cc). The aqueous phase is acidified by adding a normal solution of methanesulphonic acid (40 cc). After decantation, the organic phase is washed twice with water (100 cc in total), dried over anhydrous sodium sulphate and concentrated to dryness under reduced pressure (20 mm Hg) at 50° C. Benzyl acid L,L-$N^2$,$N^6$-dibenzyloxycarbonyl-2,6-diaminopimelate (15 g) is thus obtained in the form of an oil.

Rf=0.76 [silica gel; n-butanol/pyridine/acetic acid/water (50/20/6/24 by volume)].

Dibenzyl L,L-$N^2$,$N^6$-dibenzyloxycarbonyl-2,6-diaminopimelate can be prepared in the following manner:

A mixture of L,L-$N^2$,$N^6$-dibenzyloxycarbonyl-2,6-diaminopimelic acid (44.7 g), p-toluenesulphonic acid (3 g), benzyl alcohol (30 cc) and toluene (300 cc) is introduced into a 500 cc three-necked flask fitted with a central stirrer and a Dean Stark apparatus. The reaction mixture is heated under reflux for 5 hours. Subsequently, after stirring for 16 hours at 20° C., the white insoluble material is filtered off and washed twice with a 5% strength solution of sodium carbonate (400 cc in total) and twice with water (400 cc in total). After drying in the atmosphere, dibenzyl L,L-$N^2$,$N^6$-dibenzyloxycarbonyl-2,6-diaminopimelate (55.4 g), which melts at 118° C., is obtained.

Rf=0.53 [silica gel; acetic acid/ethyl acetate (8/2 by volume)].

L,L,$N^2$,$N^6$-Dibenzyloxycarbonyl-2,6-diaminopimelic acid can be prepared in accordance with the method of A. ARENDT et al., Roczniki Chemii Ann. Soc. Chim. Polonorum, 48, 635 (1974).

EXAMPLE 22

Isobutyl chloroformate (0.45 cc) is added to a solution, kept at −5° C., of N-acetylglycine (410 mg) in a mixture of tetrahydrofurane (70 cc) and triethylamine (0.49 cc). The mixture is stirred for 20 minutes at −5° C. and a solution, cooled to 5° C., of $N^2$-[N-(N-lauroyl-L-alanyl)-γ-D-glutamyl]-D,D/L,L-2,6-diaminopimelamic acid (2 g) in a mixture of 1N sodium hydroxide solution (7 cc) and water (10 cc) is then added. The reaction mixture is stirred for a few minutes at about 0° C. and then for 20 hours at about 20° C. It is then acidified to pH 1 by adding 1N hydrochloric acid (10 cc). The mixture is concentrated to dryness under reduced pressure (20 mm Hg) at 50° C. The amorphous solid is taken up in acetic acid (20 cc) containing neutral silica gel (0.04–0.063 mm) (5 g). The mixture is concentrated to dryness under reduced pressure (20 mm Hg) at 50° C. and the whole is introduced onto a column of diameter 3 cm, containing neutral silica gel (0.04–0.063 mm) (70 g). Elution is carried out successively with ethyl acetate (280 cc), a mixture of ethyl acetate and acetic acid (9/1 by volume) (160 cc), a mixture of ethyl acetate and acetic acid (75/25 by volume) (440 cc), a mixture of ethyl acetate and acetic acid (1/1 by volume) (240 cc) and a mixture of ethyl acetate and acetic acid (¼ by volume) (920 cc), 40 cc fractions being collected. Fractions 33 to 41 are combined and concentrated to dryness under reduced pressure (20 mm Hg) at 50° C. The resulting amorphous solid is taken up in ether (50 cc), triturated until it has all been converted to powder, filtered off and dried under reduced pressure (0.3 mm Hg). This yields a white powder (920 mg) which is chromatographed on a column of diameter 2 cm, containing neutral silica gel (0.04–0.063 mm) (25 g). Elution is carried out successively with ethyl acetate (50 cc), a mixture of ethyl acetate and acetic acid (9/1 by volume) (100 cc), a mixture of ethyl acetate and acetic acid (3/1 by volume) (100 cc), a mixture of ethyl acetate and acetic acid (1/1 by volume) (200 cc), a mixture of ethyl acetate and acetic acid (1/3 by volume) (200 cc) and acetic acid (75 cc), 25 cc fractions being collected. Fractions 17 to 27 are combined and concentrated to dryness under reduced pressure (20 mm Hg) at 50° C. The resulting amorphous solid is taken up in ether (50 cc), triturated until it has all been converted to powder, filtered off and dried under reduced pressure (0.3 mm Hg) at 60° C. $N^2$-[N-(N-Lauroyl-L-alanyl)-γ-D-glutamyl]-$N^6$-(N-acetylglycyl)-D,D/L,L-2,6-diaminopimelamic acid (720 mg), which melts above 135° C. (to give a paste), is thus obtained.

Rf=0.45 [silica gel; acetic acid].

Analysis=calculated % C, 55.51; H, 8.11; N, 12.53; found C, 54.3; H, 8.0; N, 12.3.

Sulphuric ash=4.36%.

After total hydrolysis, analysis on a Technicon autoanalyser shows the presence of the following aminoacids:

Ala 1.04 (theory=1)
Dap 0.97 (theory=1)
Glu 1.02 (theory=1)
Gly 1.00 (theory=1)

EXAMPLE 23

Isobutyl chloroformate (0.45 cc) is added to a solution, kept at −5° C., of N-benzyloxycarbonyl-D-alanine (781 mg) in a mixture of tetrahydrofurane (70 cc) and triethylamine (0.49 cc). The mixture is stirred for 20 minutes at −5° C. and a solution, cooled to 5° C. of $N^2$-[N-(N-lauroyl-L-alanyl)-γ-D-glutamyl]-D,D/L,L-2,6-diaminopimelamic acid (2 g) in a mixture of 1N sodium hydroxide solution (7 cc) and water (10 cc) is then added. The reaction mixture is stirred for a few minutes at about 0° C. and then for 20 hours at about 20° C. It is then acidified to pH 1 by adding 1N hydrochloric acid (10 cc). The tetrahydrofurane is evaporated off by concentration under reduced pressure (20 mm Hg) at 50° C. The concentrate is extracted 3 times with ethyl acetate (180 cc in total). The combined ethyl acetate phases are washed with 0.1N hydrochloric acid (20 cc) and water (20 cc) and dried over sodium sulphate. Concentration to dryness under reduced pressure (20 mm Hg) at 50° C. yields a powder (3 g) which is dissolved in acetic acid (60 cc) containing neutral silica gel (0.04–0.063 mm) (6 g). The mixture is concentrated to dryness under reduced pressure (20 mm Hg) at 20° C. and the whole is introduced onto a column of diameter 3 cm, containing neutral silica gel (0.04–0.063 mm) (82 g). Elution is carried out successively with ethyl acetate (250 cc), a mixture of ethyl acetate and acetic acid (95/5 by volume) (250 cc), a mixture of ethyl acetate and acetic acid (9/1 by volume) (250 cc), a mixture of ethyl acetate and acetic acid (85/15 by volume) (300 cc), a mixture of ethyl acetate and acetic acid (8/2 by volume) (750 cc) and a mixture of ethyl acetate and acetic acid (7/3 by volume) (250 cc), 50 cc fractions being collected. Fractions 23 to 34 are combined and concentrated to dryness under reduced pressure (20 mm Hg) at 50° C. The amorphous solid thus obtained is taken up in ether (100 cc), triturated until it has all been converted to powder, filtered off and dried under reduced pressure (0.3 mm Hg). $N^2$-[N-(N-Lauroyl-L-alanyl)-$\gamma$-D-glutamyl]-$N^6$-(N-benzyloxycarbonyl-D-alanyl)-D,D/L,L-2,6-diaminopimelamic acid (1.15 g) is obtained in the form of a white powder.

Rf=0.68 [silica gel; ethyl acetate/acetic acid (1/1 by volume)].

$N^2$-[N-(N-Lauroyl-L-alanyl)-$\gamma$-D-glutamyl]-$N^6$-(N-benzyloxycarbonyl-D-alanyl)-D,D/L,L-2,6-diaminopimelamic acid (1.09 g) is dissolved in acetic acid (26 cc). Palladium-on-charcoal (containing 3% of palladium) (1.09 g) is added and a slow stream of hydrogen is passed through the mixture for 2 hours. The catalyst is filtered off and the filtrate is concentrated to dryness under reduced pressure (20 mm Hg) at 50° C. The oil thus obtained is taken up in ether (40 cc) and triturated until it has all been converted to powder, and the powder is filtered off, washed twice with ether (20 cc in total) and dried under reduced pressure (20 mm Hg) at 20° C. This yields a powder (820 mg) which is chromatographed on a column of diameter 2 cm, containing neutral silica gel (0.04–0.063 mm) (25 g). Elution is carried out successively with a mixture of ethyl acetate and acetic acid (9/1 by volume) (120 cc), a mixture of ethyl acetate and acetic acid (75/25 by volume) (240 cc), a mixture of ethyl acetate and acetic acid (1/1 by volume) (240 cc) and a mixture of ethyl acetate and acetic acid (1/3 by volume) (720 cc), 50 cc fractions being collected. Fractions 18 to 33 are combined and concentrated to dryness under reduced pressure (20 mm Hg) at 50° C. The resulting oil is taken up in ether (40 cc) and triturated until it has all been converted to powder, and the powder is filtered off and dried under reduced pressure (0.3 mm Hg) at 60° C. $N^2$-[N-(N-Lauroyl-L-alanyl)-$\gamma$-D-glutamyl]-$N^6$-D-alanyl-D,D/L,L-2,6-diaminopimelamic acid (480 mg) is thus obtained.

Rf=0.14 [silica gel; acetic acid].

Analysis=calculated % C, 56.06; H, 8.47; N, 13.07; found C, 52.5; H, 8.0; N, 12.5.

Sulphuric ash=5.3%.

After total hydrolysis, analysis on a Technicon autoanalyser shows the presence of the following amino-acids:
Ala 2.01 (theory=2)
Dap 1.00 (theory=1)
Glu 1.10 (theory=1)

EXAMPLE 24

Isobutyl chloroformate (0.42 cc) is added to a solution, kept at −5° C., of N-benzyloxycarbonylglycine (670 mg) in a mixture of tetrahydrofurane (60 cc) and triethylamine (0.45 cc). The mixture is stirred for 20 minutes at −5° C. and a solution, cooled to 5° C., of $N^2$-[N-(N-undecanoyl-L-alanyl)-$\gamma$-D-glutamyl]-L,L/D,D-2,6-diaminopimelamic acid (1.87 g) in a mixture of 1N sodium hydroxide solution (6.4 cc) and water (10 cc) is then added. The reaction mixture is stirred for a few minutes at about 0° C. and then for 18 hours at about 20° C. It is then acidified to pH 1 by adding 1N hydrochloric acid (10 cc). The tetrahydrofurane is evaporated off by concentration under reduced pressure (20 mm Hg) at 50° C. The concentrate is extracted with ethyl acetate (100 cc). The ethyl acetate phase is washed with 0.1N hydrochloric acid (50 cc) and dried over sodium sulphate. Concentration to dryness under reduced pressure (20 mm Hg) at 50° C. yields a solid (2.3 g) which is dissolved in acetic acid (20 cc) containing neutral silica gel (0.04–0.063 mm) (5 g). The mixture is concentrated to dryness under reduced pressure (20 mm Hg) at 50° C. and the whole is introduced onto a column of diameter 2.3 cm, containing neutral silica gel (0.04–0.063 mm) (50 g). Elution is carried out successively with ethyl acetate (140 cc), a mixture of ethyl acetate and acetic acid (95/5 by volume) (80 cc), a mixture of ethyl acetate and acetic acid (9/1 by volume) (80 cc), a mixture of ethyl acetate and acetic acid (85/15 by volume) (160 cc), a mixture of ethyl acetate and acetic acid (8/2 by volume) (240 cc) and a mixture of ethyl acetate acid (7/3 by volume) (320 cc), 20 cc fractions being collected. Fractions 29 to 46 are combined and concentrated to dryness under reduced pressure (20 mm Hg) at 50° C. The resulting oil is taken up in ether (60 cc) and triturated until it has all been converted to powder, and the powder is filtered off and dried under reduced pressure (0.3 mm Hg). $N^2$-[N-(N-Undecanoyl-L-alanyl)-$\gamma$-D-glutamyl]-$N^6$-(benzyloxycarbonyl-glycyl)-L,L/D,D-2,6-diaminopimelamic acid (1.32 g) is thus obtained.

Rf=0.85 [silica gel; acetic acid].

Rf=0.68 [silica gel; ethyl acetate/acetic acid (1/1 by volume)].

$N^2$-[N-(N-Undecanoyl-L-alanyl)-$\gamma$-D-glutamyl]-$N^6$-(benzyloxycarbonylglycyl)-L,L/D,D-2,6-diaminopimelamic acid (1.32 g) is dissolved in acetic acid (18 cc). Palladium-on-charcoal (containing 3% of palladium) (1.32 g) is added and a slow stream of hydrogen is passed through the mixture for 3 hours. After filtering and concentrating the filtrate to dryness under reduced pressure (20 mm Hg) at 50° C., the resulting oil is triturated in ether (50 cc) until it has all been converted to powder, and the powder is filtered off and dried under reduced pressure (0.3 mm Hg) at 20° C. This yields a powder (1.16 g) which is chromatographed on a column of diameter 1.8 cm, containing neutral silica gel (0.04–0.063 mm) (25 g). Elution is carried out with acetic acid, 20 cc fractions being collected. Fractions 5 to 19 are combined and concentrated to dryness under reduced pressure (20 mm Hg) at 50° C. The resulting solid is taken up in ether (40 cc), filtered off and dried under reduced pressure (0.3 mm Hg) at 60° C. $N^2$-[N-(N-Undecanoyl-L-alanyl)-$\gamma$-D-glutamyl]-$N^6$-glycyl-L,L/D,D-2,6-diaminopimelamic acid (580 mg) is thus obtained.

Rf=0.24 [silica gel; n-butanol/pyridine/acetic acid/water (50/20/6/24 by volume)].

Analysis=calculated % C, 54.71; H, 8.20; N, 13.67; found C, 53.2; H, 8.2; N, 13.6.

Sulphuric ash=1.7%.

After total hydrolysis, analysis on a Technicon autoanalyser shows the presence of the following amino-acids:
Ala 1.01 (theory=1)
Dap 0.94 (theory=1)
Glu 1.00 (theory=1)
Gly 1.00 (theory=1)

$N^2$-[N-(N-Undecanoyl-L-alanyl)-$\gamma$-D-glutamyl]-L,L/D,D-2,6-diaminopimelamic acid can be prepared in the following manner:

$N^2$-[$O^1$-Benzyl-N-(N-undecanoyl-L-alanyl)-γ-D-glutamyl]-$N^6$-benzyloxycarbonyl-L,L/D,D-2,6-diaminopimelamic acid (2.55 g) is dissolved in acetic acid (35 cc). Palladium-on-charcoal (containing 3% of palladium) (2.55 g) is added and a slow stream of hydrogen is passed through the mixture for 2½ hours. The catalyst is filtered off and washed 3 times with acetic acid (30 cc in total). The filtrate is concentrated to dryness under reduced pressure (20 mm Hg) at 50° C. The amorphous solid is taken up in ether (50 cc), filtered off and dried under reduced pressure (20 mm Hg) at 20° C. $N^2$-[N-(N-Undecanoyl-L-alanyl)-γ-D-glutamyl]-L,L/D,D-2,6-diaminopimelamic acid (1.87 g) is thus obtained.

Rf=0.75 [silica gel; acetic acid].

$N^2$-[$O^1$-Benzyl-N-(N-undecanoyl-L-alanyl)-γ-D-glutamyl]-$N^6$-benzyloxycarbonyl-L,L/D,D-2,6-diaminopimelamic acid can be prepared in the following manner:

Isobutyl chloroformate (0.65 cc) is added to a solution, kept at −5° C., of benzyl N-undecanoyl-L-alanyl-α-D-glutamate (2.383 g) in a mixture of tetrahydrofurane (100 cc) and triethylamine (0.7 cc). The mixture is stirred for 30 minutes at −5° C. and a solution, cooled to 0° C., of $N^6$-benzyloxycarbonyl-L,L/D,D-2,6-diaminopimelamic acid (1.617 g) in a mixture of 1N sodium hydroxide solution (5 cc) and water (50 cc) is then added. The reaction mixture is stirred for a few minutes at about 0° C. and then for 40 hours at about 20° C. The reaction mixture is then acidified to pH 1 by adding 1N hydrochloric acid (10 cc). The tetrahydrofurane is evaporated off under reduced pressure (20 mm Hg) at 50° C. The concentrate contains a precipitate which is filtered off and washed 3 times with N/10 hydrochloric acid (60 cc in total) and water (20 cc). Drying under reduced pressure (0.3 mm Hg) at 20° C. yields a white solid (3.66 g) which is dissolved in acetic acid (20 cc) containing neutral silica gel (0.04–0.063 mm) (10 g). The mixture is concentrated to dryness under reduced pressure (20 mm Hg) at 50° C. and the whole is introduced onto a column of diameter 3.5 cm, containing neutral silica gel (0.04–0.063 mm) (75 g). Elution is carried out successively with a mixture of ethyl acetate and cyclohexane (1/1 by volume) (600 cc), a mixture of ethyl acetate and cyclohexane (3/1 by volume) (600 cc), ethyl acetate (400 cc), a mixture of ethyl acetate and acetic acid (95/5 by volume) (600 cc), a mixture of ethyl acetate and acetic acid (9/1 by volume) (500 cc) and a mixture of ethyl acetate and acetic acid (85/15 by volume) (1,200 cc), 100 cc fractions being collected. Fractions 22 to 32 are combined and concentrated to dryness under reduced pressure (20 mm Hg) at 50° C. The resulting amorphous solid is taken up in ether (80 cc), triturated until it has all been converted to powder, filtered off and dried under reduced pressure (0.3 mm Hg). $N^2$-[$O^1$-Benzyl-N-(N-undecanoyl-L-alanyl)-γ-D-glutamyl]-$N^6$-benzyloxycarbonyl-L,L/D,D-2,6-diaminopimelamic acid (2.58 g) is thus obtained.

Rf=0.62 [silica gel; ethyl acetate/acetic acid (9/1 by volume)].

Benzyl N-undecanoyl-L-alanyl-α-D-glutamate can be prepared in the following manner:

Isobutyl chloroformate (3.56 cc) is added to a solution, kept at −5° C., of undecanoic acid (5.1 g) in a mixture of tetrahydrofurane (140 cc) and triethylamine (3.84 cc). The mixture is stirred for 20 minutes at −5° C. and a solution, cooled to 0° C., of benzyl L-alanyl-α-D-glutamate hydrochloride (9.45 g) in a mixture of 1N sodium hydroxide solution (54.8 cc) and water (30 cc) is then added. The reaction mixture is stirred for 10 minutes at about −5° C. and then for 20 hours at about 20° C. The reaction mixture is then acidified to pH 1 by adding 1N hydrochloric acid (60 cc). The tetrahydrofurane is evaporated off by concentration under reduced pressure (20 mm Hg) at 50° C. The concentrate is extracted twice with ethyl acetate (80 cc in total). The combined ethyl acetate phases are washed with water (40 cc) and dried over sodium sulphate. Filtration and concentration to dryness under reduced pressure (20 mm Hg) at 50° C. yields an oil (11.89 g) which is chromatographed on a column of diameter 4.5 cm, containing neutral silica gel (0.04–0.063 mm) (250 g). Elution is carried out with ethyl acetate, 100 cc fractions being collected. Fractions 3 to 5 are combined and concentrated to dryness under reduced pressure (20 mm Hg) at 20° C. This yields a pasty solid (5.85 g) which is chromatographed on a column of diameter 3.2 cm, containing neutral silica gel (0.04–0.063 mm) (115 g). Elution is carried out successively with a mixture of ethyl acetate and cyclohexane (1/1 by volume) (1 liter), ethyl acetate (1.7 liters) and a mixture of ethyl acetate and acetic acid (99/1 by volume) (600 cc), 100 cc fractions being collected. Fractions 11 to 30 are combined and concentrated to dryness under reduced pressure (20 mm Hg) at 50° C. Benzyl N-undecanoyl-L-alanyl-α-D-glutamate (2.47 g) is thus obtained in the form of a white solid.

Rf=0.71 [silica gel; ethyl acetate/acetic acid (9/1 by volume)].

EXAMPLE 25

Isobutyl chloroformate (1.14 cc) is added to a solution, kept at −5° C., of N-benzyloxycarbonylglycine (1.83 g) in a mixture of tetrahydrofurane (165 cc) and triethylamine (1.22 cc). The mixture is stirred for 20 minutes at −5° C. and a solution, cooled to 5° C., of $N^2$-[N-(N-lauroyl-L-alanyl)-γ-D-glutamyl]-meso-2(L),6(D)-diaminopimelamic acid (5 g) in a mixture of 1N sodium hydroxide solution (17.5 cc) and water (25 cc) is then added. The reaction mixture is stirred for 10 minutes at about 0° C. and then for 70 hours at about 20° C. The tetrahydrofurane is evaporated off by concentration under reduced pressure (20 mm Hg) at 50° C. The concentrate, acidified to pH 1 by adding 1N hydrochloric acid (21 cc), gives a white precipitate which is filtered off, washed with water (200 cc) and dried in the atmosphere. This yields a powder (5.97 g) which is dissolved in acetic acid (100 cc) containing neutral silica gel (0.04–0.063 mm) (12 g). The mixture is concentrated to dryness under reduced pressure (20 mm Hg) at 50° C. and the whole is introduced onto a column of diameter 4 cm, containing neutral silica gel (0.04–0.063 mm) (280 g). Elution is carried out successively with a mixture of ethyl acetate and acetic acid (9/1 by volume) (1,360 cc), a mixture of ethyl acetate and acetic acid (85/15 by volume) (320 cc) and a mixture of ethyl acetate and acetic acid (8/2 by volume) (3,840 cc), 80 cc fractions being collected. Fractions 41 to 68 are combined and concentrated to dryness under reduced pressure (20 mm Hg) at 50° C. The resulting oil is taken up in ether (150 cc) and triturated until it has all been converted to powder, and the powder is filtered off and dried under reduced pressure (0.3 mm Hg) at 60° C. $N^2$-[N-(N-Lauroyl-L-alanyl)-γ-D-glutamyl]-$N^6$-(benzyloxycarbonylglycyl)-meso-2(L),6(D)-diaminopimelamic acid (2.37 g) is thus obtained.

Rf=0.47 [silica gel; n-butanol/pyridine/acetic acid/water (50/20/6/24 by volume)].

Rf=0.55 [silica gel; ethyl acetate/acetic acid (1/1 by volume)].

$N^2$-[N-(N-Lauroyl-L-alanyl)-γ-D-glutamyl]-$N^6$-(benzyloxycarbonylglycyl)-meso-2(L),6(D)-diaminopimelamic acid (2.35 g) is dissolved in acetic acid (70 cc). Palladium-on-charcoal (containing 3% of palladium) (2.4 g) is added and a slow stream of hydrogen is passed through the mixture for 4 hours. After filtering and concentrating the filtrate to dryness under reduced pressure (20 mm Hg) at 50° C., the resulting oil is triturated in ether (100 cc) until it has all been converted to powder, and the powder is filtered off, washed twice with ether (100 cc in total) and dried under reduced pressure (0.3 mm Hg) at 55° C. This yields a beige powder (1.91 g) which is dissolved in acetic acid (30 cc) and the solution is filtered on a column of neutral silica gel (0.04–0.063 mm) of diameter 2 cm and height 2 cm. The filtrate is concentrated to dryness under reduced pressure (20 mm Hg) at 50° C. The resulting oil is triturated in ether (100 cc) until it has all been converted to powder, and the powder is filtered off and dried under reduced pressure (0.3 mm Hg) at 58° C. $N^2$-[N-(N-Lauroyl-L-alanyl)-γ-D-glutamyl]-$N^6$-glycyl-meso-2(L),6(D)-diaminopimelamic acid (1.62 g) is thus obtained.

Rf=0.28 [silica gel; n-butanol/pyridine/acetic acid/water (50/20/6/24 by volume)].

Analysis=calculated % C, 55.40; H, 8.34; N, 13.36; found C, 52.0; H, 7.7; N, 12.1.

Sulphuric ash %=9.1.

After total hydrolysis, analysis on a Technicon autoanalyser shows the presence of the following amino-acids:

Ala 1.05 (theory=1)
Dap 0.98 (theory=1)
Glu 1.00 (theory=1)
Gly 0.96 (theory=1)

$N^2$-[N-(N-Lauroyl-L-alanyl)-γ-D-glutamyl]-meso-2(L),6(D)-diaminopimelamic acid can be prepared in the following manner:

Isobutyl chloroformate (1.6 cc) is added to a solution, kept at −5° C., of benzyl N-lauroyl-L-alanyl-α-D-glutamate (6.07 g) in a mixture of tetrahydrofurane (280 cc) and triethylamine (1.74 cc). The mixture is stirred for 20 minutes at −5° C.; a solution, cooled to 3° C., of $N^6$-benzyloxycarbonyl-meso-2(L),6(D)-diaminopimelamic acid (4 g) in a mixture of 1N sodium hydroxide solution (12.4 cc) and water (124 cc) is then added. The reaction mixture is stirred for 10 minutes at about 0° C. and then for 70 hours at about 20° C. The reaction mixture is then acidified to pH 1 by adding 1N hydrochloric acid (20 cc). The tetrahydrofurane is evaporated off by concentration under reduced pressure (20 mm Hg at 50° C. The concentrate contains a white precipitate which is filtered off, washed 3 times with 0.1N hydrochloric acid (150 cc in total) and 3 times with water (150 cc in total) and dried under reduced pressure (20 mm Hg) at 20° C. This yields a white powder (9.15 g) which is dissolved in acetic acid (100 cc) containing neutral silica gel (0.04–0.063 mm) (20 g). The mixture is concentrated to dryness and the whole is introduced onto a column of diameter 5 cm, containing neutral silica gel (0.04–0.063 mm) (400 g).

Elution is carried out successively with ethyl acetate (1.6 liters), a mixture of ethyl acetate and acetic acid (97.5/2.5 by volume) (900 cc), a mixture of ethyl acetate and acetic acid (95/5 by volume) (1,200 cc), a mixture of ethyl acetate and acetic acid (92.5/7.5 by volume) (900 cc), a mixture of ethyl acetate and acetic acid (90/10 by volume) (900 cc), a mixture of ethyl acetate and acetic acid (85/15 by volume) (300 cc) and a mixture of ethyl acetate and acetic acid (80/20 by volume) (3,200 cc), 100 cc fractions being collected. Fractions 61 to 90 are combined and concentrated to dryness under reduced pressure (20 mm Hg) at 50° C. The resulting white solid is washed twice with ether (100 cc in total) and dried under reduced pressure (0.3 mm Hg) at 60° C. $N^2$-[$O^1$-Benzyl-N-(N-lauroyl-L-alanyl)-γ-D-glutamyl]-$N^6$-benzyloxycarbonyl-meso-2(L),6(D)-diaminopimelamic acid (6.3 g) is thus obtained.

Rf=0.77 [silica gel; ethyl acetate/acetic acid (3/1 by volume)].

$N^2$-[$O^1$-Benzyl-N-(N-lauroyl-L-alanyl)-γ-D-glutamyl]-$N^6$-benzyloxycarbonyl-meso-2(L),6(D)-diaminopimelamic acid (8.2 g) is dissolved in acetic acid (225 cc). Palladium-on-charcoal (containing 3% of palladium) (8.2 g) is added and a slow stream of hydrogen is passed through the mixture for 3½ hours. After filtering and concentrating the filtrate to dryness under reduced pressure (20 mm Hg) at 50° C., the resulting oil is triturated in ether (100 cc) until it has all been converted to powder, and the powder is filtered off and dried under reduced pressure (0.3 mm Hg) at 50° C. A powder (5.9 g) is thus obtained. This powder (0.9 g) is dissolved in acetic acid and the solution is filtered over a column of neutral silica gel (0.04–0.063 mm) of diameter 2 cm and height 2 cm. The filtrate is concentrated to dryness under reduced pressure (20 mm Hg) at 50° C. The resulting residue is taken up in ether (50 cc), filtered off and dried under reduced pressure (0.3 mm Hg) at 55° C. $N^2$-[N-(N-Lauroyl-L-alanyl)-γ-D-glutamyl]-meso-2(L),6(D)-diaminopimelamic acid (0.75 g) is thus obtained.

Rf=0.38 [silica gel; n-butanol/pyridine/acetic acid/water (50/20/6/24 by volume)].

Analysis calculated %=C=56.72; H=8.64; N=12.25; found=C=52.8; H=8.1; N=11.6.

Sulphuric ash=6.9%.

After total hydrolysis, analysis on a Technicon autoanalyser shows the presence of the following amino-acids:

Ala=1.02 (theory=1)
Dap=0.96 (theory=1)
Glu=1.00 (theory=1)

$N^6$-Benzyloxycarbonyl-meso-2(L),6(D)-diaminopimelamic acid can be prepared in accordance with the process described in Belgian Pat. No. 821,385 and British Pat. No. 1,496,332.

EXAMPLE 26

Isobutyl chloroformate (0.433 cc) is added to a solution, kept at −5° C., of N-benzyloxycarbonylglycine (698 mg) in a mixture of tetrahydrofurane (65 cc) and triethylamine (0.467 cc). The mixture is stirred for 20 minutes at −5° C. and a solution, cooled to 0° C., of methyl N-α-[N-(N-lauoryl-L-alanyl)-γ-D-glutamyl]-L-lysinate (1.81 g) in a mixture of 1N sodium hydroxide solution (3.33 cc) and water (10 cc) is then added. The reaction mixture is stirred for 40 minutes at about −5° C. and then for 36 hours at about 19° C. and is then acidified to pH 1 by adding 1N hydrochloric acid (6 cc). The tetrahydrofurane is evaporated off under reduced pressure (20 mm Hg) at 50° C. The concentrate is extracted 5 times with ethyl acetate (150 cc in total). The combined ethyl acetate phases are washed with 0.1N hydrochloric acid (30 cc) and dried over sodium sulphate. Concentration to dryness under reduced pressure (20 mm Hg) at 50° C. yields an oil (2.53 g) which is dissolved in ethyl acetate (100 cc) containing neutral silica gel (0.04–0.063 mm) (6 g). The mixture is concentrated to dryness and the whole is introduced onto a column of diameter 3 cm, containing neutral silica gel (0.04–0.063 mm) (50 g).

Elution is carried out successively with ethyl acetate (80 cc) and a mixture of ethyl acetate and acetic acid (95/5 by volume) (280 cc), 40 cc fractions being collected. Fractions 4 to 8 are combined and concentrated to dryness under reduced pressure (20 mm Hg) at 50° C.

This yields an oil (2.33 g) which is again chromatographed. This oil is dissolved in acetic acid (60 cc) containing neutral silica gel (0.04–0.063 mm) (5 g). The mixture is concentrated to dryness and the whole is introduced onto a column of diameter 3 cm, containing neutral silica gel (0.04–0.063 mm) (100 g).

Elution is carried out successively with ethyl acetate (680 cc), a mixture of ethyl acetate and acetic acid (97.5/2.5 by volume) (360 cc), a mixture of ethyl acetate and acetic acid (95/5 by volume) (360 cc), a mixture of ethyl acetate and acetic acid (90/10 by volume) (360 cc) and a mixture of ethyl acetate and acetic acid (80/20 by volume) (240 cc), 40 cc fractions being collected. Fractions 32 to 41 are combined and concentrated to dryness under reduced pressure (20 mm Hg) at 50° C.

Methyl N-α-[N-(N-lauroyl-L-alanyl)-γ-D-glutamyl]-N-ε-(benzyloxycarbonylglycyl)-L-lysinate (1.35 g) is thus obtained in the form of an oil.

Rf=0.47 [silica gel; ethyl acetate/acetic acid (1/1 by volume)].

Methyl N-α-[N-(N-lauroyl-L-alanyl)-γ-D-glutamyl]-N-ε-(benzyloxycarbonylglycyl)-L-lysinate (1.3 g) is dissolved in acetic acid (35 cc). Palladium-on-charcoal (containing 3% of palladium) (1.3 g) is added and a slow stream of hydrogen is passed through the mixture for 2 and a half hours. Filtering and concentrating the filtrate to dryness under reduced pressure (20 mm Hg) at 50° C. yields an oily residue which is triturated to a powder in ether (50 cc). The powder is filtered off and dried in air. This yields a crude product (910 mg) which is chromatographed on a column of diameter 2 cm, containing neutral silica gel (0.04–0.063 mm) (40 g). Elution is carried out successively with ethyl acetate (160 cc), a mixture of ethyl acetate and acetic acid (50/50 by volume) (80 cc) and acetic acid (420 cc), 20 cc fractions being collected. Fractions 14 to 20 are combined and concentrated to dryness under reduced pressure (20 mm Hg) at 50° C. The resulting residue is triturated in ether (40 cc). After filtration and drying in air, methyl N-α-[N-(N-lauroyl-L-alanyl)-γ-D-glutamyl]-N-ε-glycyl-L-lysinate (370 mg) is obtained in the form of a cream powder.

Rf=0.50 [silica gel; n-butanol/pyridine/acetic acid/water (50/20/6/24 by volume)].

Rf=0.27 [silica gel; acetic acid].

Analysis calculated %=C, 58.07; H, 8.91; N, 11.68; found C, 57.0; H, 8.6; N, 11.1.

Sulphuric ash=22%

After total hydrolysis, analysis on a Technicon autoanalyser shows the presence of the following aminoacids:

Ala 1.00 (theory=1)
Glu 1.01 (theory=1)
Gly 0.98 (theory=1)
Lys 0.96 (theory=1)

Methyl N-α-[N-(N-lauroyl-L-alanyl)-γ-D-glutamyl]-L-lysinate can be prepared in the following manner:

Isobutyl chloroformate (1.3 cc) is added to a solution, kept at −5° C., of benzyl N-lauroyl-L-alanyl-α-D-glutamate (4.91 g) in a mixture of tetrahydrofurane (250 cc) and triethylamine (1.4 cc). The mixture is stirred for 20 minutes at −5° C. and a solution, cooled to 0° C., of methyl N-ε-benzyloxycarbonyl-L-lysinate hydrochloride (3.32 g) in a mixture of 1N sodium hydroxide solution (10 cc) and water (10 cc) is then added. The reaction mixture is stirred for 10 minutes at about −5° C. and then for 4 days at a temperature of the order of 20° C. The reaction mixture is then acidified to pH 1 by adding 1N hydrochloric acid (20 cc). The tetrahydrofurane is evaporated off by concentration under reduced pressure (20 mm Hg) at 45° C. The concentrate is extracted 5 times with chloroform (150 cc in total). The combined chloroform phases are washed with 0.1N hydrochloric acid (40 cc) and dried over sodium sulphate. Concentration to dryness under reduced pressure (20 mm Hg) at 50° C. yields a pale yellow oil which is dissolved in chloroform (60 cc) containing neutral silica gel (0.04–0.063 mm) (15 g). The mixture is concentrated to dryness and the whole is introduced onto a column of diameter 3 cm, containing neutral silica gel (0.04–0.063 mm) (150 g). Elution is carried out successively with ethyl acetate (2.5 liters) and a mixture of ethyl acetate and acetic acid (95/5 by volume) (400 cc), 100 cc fractions being collected. Fractions 6 to 27 are combined and concentrated to dryness under reduced pressure (20 mm Hg) at 50° C. Methyl N-α-[O$^1$-benzyl-N-(N-lauroyl-L-alanyl)-γ-D-glutamyl]-N-ε-benzyloxycarbonyl-L-lysinate (3.47 g) is thus obtained in the form of a white powder.

Rf=0.70 [silica gel; ethyl acetate/acetic acid (95/5 by volume)].

Rf=0.40 [silica gel; ethyl acetate].

Methyl N-α-[O$^1$-benzyl-N-(N-lauroyl-L-alanyl)-γ-D-glutamyl]-N-ε-benzyloxycarbonyl-L-lysinate (3.43 g) is dissolved in acetic acid (70 cc). Palladium-on-charcoal (containing 3% of palladium) (3.43 g) is added and a slow stream of hydrogen is then passed through the mixture for 2 hours. The catalyst is filtered off and washed twice with acetic acid (20 cc in total) and the combined filtrates are concentrated to dryness under reduced pressure (20 mm Hg) at 50° C. The residue is triturated in ether (50 cc). This yields a powder which is filtered off and dried in air. Methyl N-α-[N-(N-lauroyl-L-alanyl)-γ-D-glutamyl]-L-lysinate (1.89 g) is thus obtained.

Rf=0.50 [silica gel; n-butanol/pyridine/acetic acid/water (50/20/6/24 by volume)].

Rf=0.29 [silica gel; acetic acid].

EXAMPLE 27

Isobutyl chloroformate (1.07 cc) is added to a solution, kept at −5° C., of benzyl N-lauroyl-L-alanyl-α-D-glutamate (4.026 g) in a mixture of tetrahydrofurane (135 cc) and triethylamine (1.15 cc). The mixture is stirred for 20 minutes at −7° C. and a solution, cooled to 4° C., of N-α-(benzyloxycarbonylglycyl)-L-lysinamide hydrochloride in a mixture of 1N sodium hydroxide solution (8.2 cc) and water (22 cc) is then added. The reaction mixture is stirred for 10 minutes at about −5° C. and then for 65 hours at about 20° C. and is then acidified to pH 1 by adding 1N hydrochloric acid (11 cc). The tetrahydrofurane is evaporated off under reduced pressure (20 mm Hg) at 45° C. The concentrate is diluted by adding water (50 cc). The precipitate formed in the concentrate is filtered off, washed 3 times with water (75 cc in total) and dried. This yields a white solid (5.58 g) which is dissolved in acetic acid (70 cc) containing neutral silica gel (0.04–0.063 mm) (12 g). The mixture is concentrated to dryness and the whole is introduced onto a column of diameter 3 cm, containing neutral silica gel (0.04–0.063 mm) (100 g).

Elution is carried out successively with ethyl acetate (350 cc), a mixture of ethyl acetate and acetic acid (95/5 by volume) (250 cc), a mixture of ethyl acetate and acetic acid (9/1 by volume) (850 cc), a mixture of ethyl acetate and acetic acid (75/25 by volume) (450 cc) and a mixture of ethyl acetate and acetic acid (1/1 by volume) (350 cc), 50 cc fractions being collected. Fractions 34 to 39 are combined and concentrated to dryness under reduced pressure (20 mm Hg) at 50° C. The resulting hard foam is taken up in ether (50 cc) and triturated until it has all been converted to powder, and the powder is filtered off and dried under reduced pressure (0.3 mm Hg). N-α-(benzyloxycarbonylglycyl)-N-ε-[O$^1$-benzyl-N-(N-lauroyl-L-alanyl)-γ-D-glutamyl]-L-lysinamide (1.43 g) is thus obtained.

Rf=0.88 [silica gel; n-butanol/pyridine/acetic acid/water (50/20/6/24 by volume)].

Rf=0.37 [silica gel; ethyl acetate/acetic acid (3/1 by volume)].

N-α-(Benzyloxycarbonylglycyl)-N-ε-[O$^1$-benzyl-N-(N-lauroyl-L-alanyl)-γ-D-glutamyl]-L-lysinamide (1.43 g) is dissolved in acetic acid (85 cc). Palladium-on-charcoal (containing 3% of palladium) (1.43 g) is added and a slow stream of hydrogen is passed through the mixture for 2 hours. The catalyst is filtered off and washed twice with acetic acid (20 cc in total) and the combined filtrates are concentrated to dryness under reduced pressure (20 mm Hg) at 50° C. The oily residue thus obtained is triturated in ether (75 cc) and gives a solid which is filtered off. This yields a white solid (990 mg) with which a similar product (490 mg) obtained in the same manner is combined, and the combined product is chromatographed on a column of diameter 2 cm, containing neutral silica gel (0.04–0.063 mm) (29 g). Elution is carried out with acetic acid, 40 cc fractions being collected. Fractions 13 to 32 are combined and concentrated to dryness under reduced pressure (20 mm Hg) at 50° C. N-α-Glycyl-N-ε-[N-(N-lauroyl-L-alanyl)-γ-D-glutamyl]-L-lysinamide (510 mg) is thus obtained.

Rf=0.42 [silica gel; n-butanol/pyridine/acetic acid/water (50/20/6/24 by volume)].

Analysis calculated %=C, 57.51; H, 8.97; N, 14.37; found C, 54.9; H, 8.6; N, 13.3.

Sulphuric ash=1.6%.

After total hydrolysis, analysis on a Technicon autoanalyser shows the presence of the following amino-acids:

Ala 1.04 (theory=1)
Glu 0.99 (theory=1)
Gly 1.00 (theory=1)
Lys 0.95 (theory=1)

N-α-(Benzyloxycarbonylglycyl)-L-lysinamide hydrochloride can be prepared in the following manner:

N-α-(Benzyloxycarbonylglycyl)-N-ε-t-butoxycarbonyl-L-lysinamide (4.18 g) is dissolved in a 1.7N anhydrous solution of hydrogen chloride in acetic acid (80 cc). The resulting solution is stirred for 2 hours at a temperature of the order of 20° C. and the reaction medium is then added to anhydrous ether (400 cc). An oily precipitate is separated off by decantation, washed with ether (200 cc) and dried under reduced pressure (0.3 mm Hg). N-α-(Benzyloxycarbonylglycyl)-L-lysinamide hydrochloride (3.16 g) is thus obtained in the form of a paste.

Rf=0.48 [silica gel; n-butanol/pyridine/acetic acid/water (50/20/6/24 by volume)].

N-α-(Benzyloxycarbonylglycyl)-N-ε-t-butoxycarbonyl-L-lysinamide can be prepared in the following manner:

Isobutyl chloroformate (1.267 cc) is added to a solution, kept at −1° C., of N-benzyloxycarbonylglycine (2.397 g) in a mixture of tetrahydrofurane (35 cc) and triethylamine (1.365 cc). The mixture is stirred for 20 minutes at −3° C. and a solution, cooled to 5° C., of N-ε-t-butoxycarbonyl-L-lysinamide (3.25 g) in tetrahydrofurane (50 cc) is then added. The reaction mixture is stirred for 15 minutes at about −5° C. and then for 20 hours at about 20° C. The insoluble material is filtered off and the tetrahydrofurane is then evaporated off under reduced pressure (20 mm Hg) at 45° C. The concentrate is diluted by adding water (150 cc) and extracted 3 times with ethyl acetate (225 cc in total). The combined ethyl acetate phases are washed successively with iced 0.1N hydrochloric acid (60 cc), 10% strength sodium carbonate solution (60 cc) and twice with a saturated solution of sodium chloride (120 cc in total) and dried over sodium sulphate. After concentration to dryness under reduced pressure (20 mm Hg) at 45° C., N-α-(benzyloxycarbonylglycyl)-N-ε-t-butoxycarbonyl-L-lysinamide (4.18 g) is obtained in the form of an oil.

Rf=0.77 [silica gel; ethyl acetate/acetic acid (3/1 by volume)].

N-ε-t-Butoxycarbonyl-L-lysinamide can be prepared in the following manner:

Isobutyl chloroformate (1.3 cc) is added to a solution, kept at −5° C., of N-α-benzyloxycarbonyl-N-ε-t-butoxycarbonyl-L-lysine (3.8 g) in a mixture of chloroform (38 cc) and triethylamine (1.4 cc). The mixture is stirred for 20 minutes at −5° C. and a slow stream of ammonia is then passed through the mixture for 3 hours. The reaction medium is then diluted by adding chloroform (100 cc), washed twice with a 10% strength solution of sodium carbonate (100 cc in total) and 5 times with water (250 cc in total) and dried over sodium sulphate. After concentration to dryness under reduced pressure (20 mm Hg) at 50° C., N-α-benzyloxycarbonyl-N-ε-t-butoxycarbonyl-L-lysinamide (3.76 g), which melts at 142°–144° C., is obtained.

Rf=0.52 [silica gel; ethyl acetate].

N-α-Benzyloxycarbonyl-N-ε-t-butoxycarbonyl-L-lysinamide (3.7 g) is dissolved in acetic acid (130 cc). Palladium-on-charcoal (containing 3% of palladium) (3.7 g) is added and a slow stream of hydrogen is passed through the mixture for 2 hours. The catalyst is filtered off and washed twice with acetic acid (20 cc in total); the combined filtrates are concentrated to dryness under reduced pressure (20 mm Hg) at 50° C. The oily residue is triturated in ether (200 cc). After decantation and drying, N-ε-t-butoxycarbonyl-L-lysinamide (3.25 g) is obtained.

Rf=0.60 [silica gel; n-butanol/pyridine/acetic acid/water (50/20/6/24 by volume)].

EXAMPLE 28

Isobutyl chloroformate (0.31 cc) is added to a solution, kept at −11° C., of N-benzyloxycarbonylglycine (506 mg) in a mixture of tetrahydrofurane (40 cc) and triethylamine (0.34 cc). The mixture is stirred for 20 minutes at −11° C. and a solution, cooled to 5° C., of N⁶-[O¹-benzyl-N-(N-lauroyl-L-alanyl)-γ-D-glutamyl]-D,D/L,L-2,6-diaminopimelamic acid hydrochloride (1.69 g) in a mixture of 1N sodium hydroxide solution (4.84 cc) and water (40 cc) is then added. The reaction mixture is stirred for a few minutes at about −10° C. and then for 65 hours at about 20° C. It is then acidified to pH 1 by adding 1N hydrochloric acid (10 cc). The tetrahydrofurane is evaporated off by concentration under reduced pressure (20 mm Hg) at 50° C. The white precipitate which has appeared in the concentrate is filtered off, washed 4 times with water (80 cc in total) and dried in the atmosphere. This yields a crude product (1.74 g) which is dissolved in acetic acid (30 cc) containing neutral silica gel (0.04–0.063 mm) (5 g). The mixture is concentrated to dryness under reduced pressure (20 mm Hg) at 50° C. and the whole is introduced onto a column of diameter 30 mm, containing neutral silica gel (0.04–0.063 mm) (60 g).

Elution is carried out successively with a mixture of ethyl acetate and acetic acid (9/1 by volume) (160 cc) and a mixture of ethyl acetate and acetic acid (8/2 by volume) (560 cc), 20 cc fractions being collected. Fractions 16 to 25 are combined and concentrated to dryness under reduced pressure (20 mm Hg) at 50° C. The resulting amorphous solid is taken up in ether (30 cc), triturated until it has all been converted to powder, filtered off and dried under reduced pressure (0.3 mm Hg). N⁶-[O¹-Benzyl-N-(N-lauroyl-L-alanyl)-γ-D-glutamyl]-N²-benzyloxycarbonylglycyl-D,D/L,L-2,6-diaminopimelamic acid (320 mg) is thus obtained.

N⁶-[O¹-Benzyl-N-(N-lauroyl-L-alanyl)-γ-D-glutamyl]-N²-benzyloxycarbonylglycyl-D,D/L,L-2,6-diaminopimelamic acid (320 mg) is dissolved in acetic acid (25 cc). Palladium-on-charcoal (containing 3% of palladium) (320 mg) is added and a slow stream of hydrogen is passed through the mixture for 2¼ hours. Filtering and concentrating the filtrate to dryness under reduced pressure (20 mm Hg) at 50° C. yields a solid (290 mg) which is chromatographed on a column of diameter 1 cm, containing neutral silica gel (0.04–0.063 mm) (6 g). Elution is carried out with acetic acid, 5 cc fractions being collected. Fractions 25 to 32 are combined and concentrated to dryness under reduced pressure (20 mm Hg) at 50° C. The resulting amorphous solid is taken up in ether (20 cc), filtered off and dried under reduced pressure (0.3 mm Hg) at 20° C. N⁶-[N-(N-Lauroyl-L-alanyl)-γ-D-glutamyl]-N²-glycyl-D,D/L,L-2,6-diaminopimelamic acid (30 mg) is thus obtained.

Rf=0.22 [silica gel; n-butanol/pyridine/acetic acid/water (50/20/6/24 by volume)].

After total hydrolysis, analysis on a Technicon autoanalyser shows the presence of the following amino-acids:
Ala 0.95 (theory=1)
Glu 1.04 (theory=1)
Gly 1.00 (theory=1)
Dap 1.00 (theory=1)

N⁶-[O¹-Benzyl-N-(N-lauroyl-L-alanyl)-γ-D-glutamyl]-L,L/D,D-2,6-diaminopimelamic acid hydrochloride can be prepared in the following manner:

Isobutyl chloroformate (0.56 cc) is added to a solution, kept at −5° C., of benzyl N-lauroyl-L-alanyl-α-D-glutamate (2.12 g) in a mixture of tetrahydrofurane (86 cc) and triethylamine (0.6 cc). The mixture is stirred for 30 minutes at −5°C. and a solution, cooled to 2° C., of N²-t-butoxycarbonyl-D,D/L,L-2,6-diaminopimelamic acid (1.25 g) in a mixture of 1N sodium hydroxide solution (4.32 cc) and water (43 cc) is then added. The reaction mixture is stirred for a few minutes at about −5° C. and then for 18 hours at about 20° C. It is then acidified by adding a saturated solution of citric acid (50 cc). The tetrahydrofurane is evaporated off by concentration under reduced pressure (20 mm Hg) at 50° C. The concentrate is extracted 5 times with ethyl acetate (200 cc in total). The combined ethyl acetate phases are washed with water (25 cc) and dried over sodium sulphate. Concentration to dryness under reduced pressure (20 mm Hg) at 50° C. yields an oil which is dissolved in a mixture of ethyl acetate (50 cc) and acetic acid (10 cc), containing neutral silica gel (0.04–0.063 mm) (10 g). The mixture is concentrated to dryness under reduced pressure (20 mm Hg) at 50° C. and the whole is introduced onto a column of diameter 2 cm, containing neutral silica gel (0.04–0.063 mm) (50 g).

Elution is carried out successively with ethyl acetate (200 cc), a mixture of ethyl acetate and acetic acid (95/5 by volume) (280 cc) and a mixture of ethyl acetate and acetic acid (9/1 by volume) (320 cc), 40 cc fractions being collected. Fractions 5 to 13 are combined and concentrated to dryness under reduced pressure (20 mm Hg) at 50° C. N⁶-[O¹-Benzyl-N-(N-lauroyl-L-alanyl)-γ-D-glutamyl]-N²-t-butoxycarbonyl-L,L/D,D-2,6-diaminopimelamic acid (2.23 g) is thus obtained in the form of an oil.

Rf=0.39 [silica gel; ethyl acetate/acetic acid (9/1 by volume)].

N⁶-[O¹-Benzyl-N-(N-lauroyl-L-alanyl)-γ-D-glutamyl]-N²-t-butoxycarbonyl-D,D/L,L-2,6-diaminopimelamic acid (2.19 g) is dissolved in a saturated anhydrous solution of hydrogen chloride in acetic acid (22 cc). The reactants are left in contact for 3 hours at 20° C. and the mixture is then concentrated to dryness under reduced pressure (20 mm Hg) at 50° C. N⁶-[O¹-Benzyl-N-(N-lauroyl-L-alanyl)-γ-D-glutamyl]-D,D/L,L-2,6-diaminopimelamic acid hydrochloride (1.74 g) is thus obtained in the form of a partially crystalline oil.

Rf=0.47 [silica gel; n-butanol/pyridine/acetic acid/water (50/20/6/24 by volume)].

Rf=0.26 [silica gel; acetic acid].

N²-t-Butoxycarbonyl-D,D/L,L-2,6-diaminopimelamic acid can be prepared in the following manner:

N²-t-Butoxycarbonyl-N⁶-benzyloxycarbonyl-D,D/L,L-2,6-diaminopimelamic acid (4 g) is dissolved in acetic acid (100 cc). Palladium-on-charcoal (containing 3% of palladium) (4 g) is added and a slow stream of hydrogen is passed through the mixture for 3 hours. The catalyst is filtered off and washed with acetic acid (10 cc) and the combined filtrates are concentrated to dryness under reduced pressure (20 mm Hg) at 50° C. The oily residue thus obtained is triturated in ether (50 cc) until it has all been converted to powder. After filtration and drying, N²-t-butoxycarbonyl-D,D/L,L-2,6-diaminopimelamic acid (3 g) is thus obtained.

Rf=0.34 [silica gel; acetic acid].

EXAMPLE 29

A chlormethylated styrene/divinylbenzene copolymer (98/2) (15 g) containing 1.2 milliequivalents of chlorine per gram is added to a solution of N-α-t-butoxycarbonyl-N-ε-(benzyloxycarbonylglycyl)-lysine (7.87 g) in ethanol (70 cc). The reaction medium is stirred for 10 minutes at 20° C., triethylamine (2.25 cc) is then added and the mixture is then stirred for a further 65 hours at 78° C. The polymer is filtered off, washed successively 3 times with ethanol (300 cc in total) and 3 times with methylene chloride (300 cc in total) and then dried under reduced pressure (0.3 mm Hg) at 20° C. N-α-t-Butoxycarbonyl-N-ε-(benzyloxycarbonylglycyl)-L-lysyl-polymer is thus obtained.

After total hydrolysis, analysis on a Technicon autoanalyser shows the presence of the following amino-acids:
Gly 0.35 mmol per gram of polymer
Lys 0.33 mmol per gram of polymer D-Glutamic acid is attached to the blocked dipeptide-polymer by carrying out the following sequence of operations in a reactor fitted with a stirrer and, at its base, with a fritted glass filter:

(1) The blocked dipeptide-polymer is washed 3 times in succession with methylene chloride (3×100 cc). Each addition of solvent is followed by stirring for 3 minutes and then by draining.

(2) The t-butoxycarbonyl protective group is then removed by adding a mixture of trifluoroacetic acid and methylene chloride (1/1 by volume) (100 cc), stirring for 20 minutes and then draining.

(3) The resin is then washed successively with
a. methylene chloride (3×100 cc),
b. methanol (3×100 cc) and
c. methylene chloride (3×100 cc),
each addition of solvent being followed by stirring for 3 minutes and by draining.

(4) The dipeptide-polymer is then neutralised by adding a mixture of methylene chloride and triethylamine (9/1 by volume) (100 cc), stirring for 10 minutes and then draining.

(5) The resin is then washed with methylene chloride (3×100 cc), each addition of solvent being followed by stirring for 3 minutes and by draining.

(6) A solution of N-t-butoxycarbonyl-O$^1$-benzyl-O$^5$-succinimido-D-glutamic acid (5.2 g) in methylene chloride (100 cc) is added, the mixture is stirred for 18 hours and the resin is drained.

(7) The resin is washed successively with
a. methylene chloride (3×100 cc),
b. acetic acid (3×100 cc) and
c. methylene chloride (3×100 cc),
each addition of solvent being followed by stirring for 3 minutes and by draining.

(8) A solution of N-t-butoxycarbonyl-O$^1$-benzyl-O$^5$-succinimido-D-glutamic acid (5.2 g) in methylene chloride (100 cc) is added, the mixture is stirred for 18 hours and the resin is drained.

(9) The resin is washed successively with
a. methylene chloride (3×100 cc),
b. acetic acid (3×100 cc) and
c. methylene chloride (3×100 cc),
each addition of solvent being followed by stirring for 3 minutes and by draining.

N-α-(O$^1$-Benzyl-N-t-butoxycarbonyl-D-glutamyl)-N-ε-(benzyloxycarbonylglycyl)-L-lysyl-polymer is thus obtained.

L-Alanine is attached to the blocked tripeptide-polymer by repeating the above operations Nos. 1, 2, 3, 4, 5, 6 and 9.

Operation No. 6 is modified as follows:
The following are added in succession:

a. A solution of N-t-butoxycarbonyl-L-alanine (4.7 g) in methylene chloride (100 cc), with stirring for 10 minutes, and b. Dicyclohexylcarbodiimide (5.16 g), with stirring for 16 hours and draining.

N-α-[O$^1$-Benzyl-N-(t-butoxycarbonyl-L-alanyl)-γ-D-glutamyl]-N-ε-(benzyloxycarbonylglycyl)-L-lysyl-polymer is thus obtained.

Octanoic acid is attached to the blocked tetrapeptide-polymer by repeating the above operations Nos. 1, 2, 3, 4, 5, 6 and 9.

Operation No. 6 is modified as follows:
The following are added in succession:

a. A solution of octanoic acid (1.64 g) in methylene chloride (100 cc), with stirring for 10 minutes, and b. Dicyclohexylcarbodiimide (2.35 g), with stirring for 16 hours and draining.

N-α-[O$^1$-Benzyl-N-(N-octanoyl-L-alanyl)-γ-D-glutamyl]-N-ε-(benzyloxycarbonylglycyl)-L-lysyl-polymer is thus obtained.

This polymer is suspended in trifluoroacetic acid (100 cc) contained in a reactor fitted with a stirrer and, at its base, with a fritted glass filter. A stream of hydrogen bromide is passed through this suspension for 90 minutes. The resin is then drained and washed 3 times with acetic acid (300 cc in total), each addition of acetic acid being followed by stirring for 3 minutes and by draining. The filtrates are combined and concentrated to dryness under reduced pressure (20 mm Hg) at 50° C. The resulting oily residue is taken up twice in methanol (50 cc in total) and concentrated to dryness each time under reduced pressure (20 mm Hg) at 50° C. This yields an oil (about 2 g) which is chromatographed on a column of diameter 1.6 cm, containing neutral silica gel (0.04–0.063 mm) (15 g).

Elution is carried out successively with a mixture of ethyl acetate and acetic acid (3/1 by volume) (300 cc), a mixture of ethyl acetate and acetic acid (1/1 by volume) (250 cc), a mixture of ethyl acetate and acetic acid (⅓ by volume) (250 cc) and acetic acid (350 cc), 50 cc fractions being collected.

Fractions 8 to 23 are combined and concentrated to dryness under reduced pressure (20 mm Hg) at 50° C. This yields a cream powder (0.94 g) which is again chromatographed on a column of diameter 1.5 cm, containing neutral silica gel (0.04–0.063 mm) (10 g). Elution is carried out successively with ethyl acetate (100 cc) and a mixture of ethyl acetate and methanol (9/1 by volume) (500 cc), 50 cc fractions being collected. Fractions 6 to 10 are combined and concentrated to dryness under reduced pressure (20 mm Hg) at 50° C. Methyl N-α-[O$^1$-methyl-N-(N-octanoyl-L-alanyl)-γ-D-glutamyl]-N-ε-glycyl-L-lysinate hydrobromide (390 mg) is thus obtained.

Rf=0.69 [silica gel; n-butanol/pyridine/acetic acid/water (50/20/6/24 by volume)].

Rf=0.75 [silica gel; isoamyl alcohol/pyridine/water (35/35/30 by volume)].

Analysis: calculated %=C, 48.90; H, 7.58; N, 10.97; found C, 45.3; H, 6.8; N, 10.1.

Sulphuric ash=5.21%.

After total hydrolysis, analysis on a Technicon autoanalyser shows the presence of the following amino-acids:
Ala 1.00 (theory=1)
Glu 0.90 (theory=1)
Gly 1.16 (theory=1)
Lys 1.10 (theory=1)

N-α-t-Butoxycarbonyl-N-ε-(benzyloxycarbonyl-glycyl)-L-lysine can be prepared in accordance with the method of M. KHOSLA et al., Indian J. Chem., 5, 237 (1967).

EXAMPLE 30

A chloromethylated styrene/divinylbenzene copolymer (98/2) (15 g) containing 1.2 milliequivalents of chlorine per gram is added to a solution of N-α-[O$^1$-benzyl-N-(t-butoxycarbonyl-L-alanyl)-γ-D-glutamyl]-N-ε-(benzyloxycarbonylglycyl)-L-lysine (10 g) in ethanol (50 cc). The reaction medium is stirred for 10 minutes at 20° C., triethylamine (1.92 cc) is then added and the reaction medium is stirred for 65 hours at 78° C. The polymer is filtered off, washed successively 3 times with ethanol (300 cc in total) and 3 times with methylene chloride (300 cc in total) and then dried under reduced pressure (0.3 mm Hg) at 20° C. N-α-[O$^1$-Benzyl-N-(t-butoxycarbonyl-L-alanyl)-γ-D-glutamyl]-N-ε-(benzyloxycarbonylglycyl)-L-lysyl-polymer (18.8 g) is thus obtained.

After total hydrolysis, analysis on a Technicon autoanalyser shows the presence of the following aminoacids:
Ala=0.19 mmol per gram of polymer
Glu=0.18 mmol per gram of polymer
Gly=0.18 mmol per gram of polymer
Lys=0.17 mmol per gram of polymer Hexanoic acid is attached to the blocked tetrapeptide-polymer by carrying out the following sequence of operations in a reactor fitted with a stirrer and, at its base, with a fritted glass filter:

(1) The blocked tetrapeptide-polymer is washed 3 times in succession with methylene chloride (3×100 cc). Each addition of solvent is followed by stirring for 3 minutes and then by draining.

(2) The t-butoxycarbonyl protective group of the alanine is then removed by adding a mixture of trifluoroacetic acid and methylene chloride (1/1 by volume) (100 cc), stirring for 20 minutes and then draining.

(3) The resin is then washed successively with
 a. methylene chloride (3×100 cc),
 b. methanol (3×100 cc) and
 c. methylene chloride (3×100 cc),
each addition of solvent being followed by stirring for 3 minutes and by draining.

(4) The tetrapeptide-polymer is then neutralised by adding a mixture of methylene chloride and N-methylmorpholine (9/1 by volume) (100 cc), stirring for 10 minutes and then draining.

(5) The resin is then washed with methylene chloride (3×100 cc), each addition of solvent being followed by stirring for 3 minutes and by draining.

(6) The following are then added in succession:
 a. a solution of hexanoic acid (1.16 g) in methylene chloride (100 cc), with stirring for 10 minutes, and
 b. dicyclohexylcarbodiimide (2.06 g), with stirring for 20 hours and draining.

(7) The resin is washed successively with
 a. methylene chloride (3×100 cc),
 b. acetic acid (3×100 cc) and
 c. methylene chloride (3×100 cc),
each addition of solvent being followed by stirring for 3 minutes and by draining.

(8) The following are then added in succession:
 a. hexanoic acid (1.16 g), with stirring for 10 minutes, and
 b. dicyclohexylcarbodiimide (2.06 g), with stirring for 20 hours and draining.

(9) The resin is washed successively with
 a. methylene chloride (3×100 cc),
 b. acetic acid (3×100 cc) and
 c. methylene chloride (3×100 cc),
each addition of solvent being followed by stirring for 3 minutes and by draining.

N-α-[O$^1$-Benzyl-N-(N-hexanoyl-L-alanyl)-γ-D-glutamyl]-N-ε-(benzyloxycarbonylglycyl)-L-lysyl-polymer is thus obtained. This polymer is suspended in trifluoroacetic acid (100 cc) contained in a reactor fitted with a stirrer and, at its base, with a fritted glass filter. A stream of hydrogen bromide is passed through this suspension for 90 minutes. The resin is then drained and washed 3 times with acetic acid (300 cc in total), each addition of acetic acid being followed by stirring for 3 minutes and by draining. The filtrates are combined and concentrated to dryness under reduced pressure (20 mm Hg) at 55° C. The oily residue thus obtained is triturated in ethyl acetate (50 cc) until it has all been converted to powder, and the powder is filtered off and washed 3 times with ether (90 cc in total). This yields a beige powder (1.15 g) which is chromatographed on a column of diameter 1.8 cm, containing neutral silica gel (0.04–0.063 mm) (15 g). Elution is carried out with a mixture of ethyl acetate and acetic acid (1/1 by volume), 20 cc fractions being collected. Fractions 13 to 24 are combined and concentrated to dryness under reduced pressure (20 mm Hg) at 50° C.; the resulting residue is dissolved in acetic acid (5 cc) and precipitated by adding ether (300 cc). After filtration and drying, N-α-[N-(N-hexanoyl-L-alanyl)-γ-D-glutamyl]-N-ε-glycyl-L-lysine hydrobromide (470 mg) is obtained.

Rf=0.26 [silica gel; n-butanol/pyridine/acetic acid/water (50/20/6/24 by volume)].

Analysis: calculated %=C=45.36; H=6.92; N=12.02; found=C=42.3; H=7.0; N=11.2.

After total hydrolysis, analysis on a Tehnicon autoanalyser shows the presence of the following aminoacids:
Ala 1.05 (theory=1)
Glu 0.95 (theory=1)
Gly 1.00 (theory=1)
Lys 0.97 (theory=1)

N-α-[O$^1$-Benzyl-N-(t-butoxycarbonyl-L-alanyl)-γ-D-glutamyl]-N-ε-(benzyloxycarbonylglycyl)-L-lysine can be prepared in the following manner:

Isobutyl chloroformate (4.57 cc) is added to a solution, kept at −8° C., of benzyl N-t-butoxycarbonyl-L-alanyl-α-D-glutamate (14.3 g) in a mixture of tetrahydrofurane (420 cc) and triethylamine (4.92 cc). The mixture is stirred for 20 minutes at −8° C. and a solution, cooled to 5° C., of N-ε-(benzyloxycarbonylglycyl)-L-lysine (11.8 g) in a mixture of 1N sodium hydroxide solution (35 cc) and water (35 cc) is then added. The reaction mixture is stirred for 10 minutes at about 0° C. and then for 16 hours at about 20° C. The tetrahydrofurane is then evaporated off by concentration under reduced pressure (20 mm Hg) at 50° C. The concentrate, cooled to 0° C., is acidified to pH 2 by adding 1N hydrochloric acid (70 cc) and extracted 3 times with ethyl acetate (600 cc in total). The combined ethyl acetate phases are washed with water (100 cc) and a saturated solution of sodium chloride (100 cc), dried over sodium sulphate and concentrated to dryness under reduced pressure (20 mm Hg) at 50° C. This yields a hard foam (24.3 g) which is chromatographed on a column of diameter 4.8 cm, containing neutral silica gel (0.04–0.063 mm) (450 g). Elution is carried out successively with a mixture of ethyl acetate and cyclohexane (1/1 by volume) (520 cc), a mixture of ethyl acetate and cyclohexane (3/1 by volume) (360 cc), ethyl acetate (480 cc), a mixture of ethyl acetate and acetic acid (95/5 by volume) (520 cc), a mixture of ethyl acetate and acetic acid (90/10 by volume) (1,040 cc), a mixture of ethyl acetate and acetic acid (80/20 by volume) (520 cc) and a mixture of ethyl acetate and acetic acid (70/30 by volume) (1,080 cc), 40 cc fractions being collected. Fractions 57 to 101 are combined and concentrated to dryness under reduced pressure (20 mm Hg) at 520° C. The product thus obtained is recrystallised from ethyl acetate.

N-α-[O$^1$-Benzyl-N-(t-butoxycarbonyl-L-alanyl)-γ-D-glutamyl]-N-ε-(benzyloxycarbonylglycyl)-L-lysine (13.9 g), which melts at about 90° C. (to give a paste), is thus obtained.

Rf=0.55 [silica gel; ethyl acetate/acetic acid (3/1 by volume)].

After total hydrolysis, analysis on a Technicon autoanalyser shows the presence of the following aminoacids:
Ala 1.00 (theory=1)
Glu 1.03 (theory=1)
Gly 1.00 (theory=1)
Lys 0.94 (theory=1)

The present invention includes within its scope pharmaceutical compositions which comprise at least one peptide of general formula II or non-toxic salt thereof, in association with one or more compatible and pharmaceutically acceptable carriers or diluents. These compositions can be used either as vaccine adjuvants or as non-specific stimulants of anti-infectious immunity.

When used as vaccine adjuvants, the compounds according to the invention are administered at the same time and by the same method as the antigen (viral, bacterial, parasitic or other antigen) against which it is desired to increase the cell immunity reactions (delayed-type hypersensitivity) or the production of circulating or local antibodies in the immunised subject (man or domestic animal).

The products are administered in relatively low doses (of the order of one mg) as a mixture with the antigen and by the same method (e.g. by the intramuscular, subcutaneous, intravenous, intranasal or oral method). If necessary, the compound according to the invention and the antigen can be emulsified in an appropriate oily excipient or incorporated into liposomes.

As non-specific immunostimulants, the compounds of the invention are administered in doses of from 0.1 to 50 mg/kg animal body weight by the parenteral method (intravenous, subcutaneous or intramuscular method) or by the intranasal, oral, rectal or, if appropriate, intratumoral method.

Solid compositions for oral administration include tablets, pills, powders and granules. In such solid compositions the active compound is admixed with at least one inert diluent such as sucrose, lactose or starch. The compositions may also comprise, as is normal practice, additional substances other than inert diluents, e.g. lubricating agents, such as magnesium stearate.

Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting, sweetening and flavouring agents.

Preparations according to the invention for parenteral administration include sterile aqueous solutions, suspensions and emulsions. Examples of non-aqueous vehicles are propylene glycol, polyethylene glycol, vegetable oils such as olive oil, and injectable organic esters such as ethyl oleate. These compositions may also contain adjuvants in particular wetting agents, emulsifiers or dispersing agents. They may be sterilised by, for example, filtration through a bacteria-retaining filter, by incorporation in the compositions of sterilising agents, or by heating. They may also be manufactured in the form of solid compositions sterilised, e.g. by irradiation, which can be dissolved in sterile water or dispersed in any other sterile injectable medium before use.

Compositions for intranasal administration may be sterile aqueous solutions, suspensions or emulsions, which may if necessary be associated with a compatible propellant.

Compositions for rectal administration are suppositories which contain, in addition to the active substance, excipients such as cacao butter or a suitable wax base.

The following Examples illustrate pharmaceutical compositions according to the invention:

EXAMPLE 31

A solution which can be administered intravenously and has the following composition is prepared in accordance with the usual technique:
N$^2$-[N-(N-lauroyl-L-alanyl)-γ-D-glutamyl]D,D/L,L-N$^6$-glycyl-2,6-diaminopimelamic acid: 0.5 g
injectable solution: 5 cc

EXAMPLE 32

A solution which can be administered intravenously and has the following composition is prepared in accordance with the usual technique:
methyl N-α-[N-(N-lauroyl-L-alanyl)-γ-D-glutamyl]-N-ε-glycyl-L-lysinate: 0.5 g
injectable solution: 5 cc

We claim:
1. A peptide of the formula:

$$\begin{array}{c} R-NH-CH-CO-NH-CH-CO-R_1 \\ \quad\quad\quad | \quad\quad\quad\quad\quad\quad | \\ \quad\quad\quad CH_3 \quad\quad\quad CH_2CH_2-CO-NH-CH-R_2 \\ \quad\quad\quad\quad\quad\quad\quad\quad\quad\quad\quad\quad\quad\quad\quad | \\ \quad\quad\quad\quad\quad\quad\quad\quad\quad\quad\quad\quad\quad\quad\quad (CH_2)_3 \\ \quad\quad\quad\quad\quad\quad\quad\quad\quad\quad\quad\quad\quad\quad\quad | \\ \quad\quad\quad\quad\quad\quad\quad\quad\quad\quad\quad\quad R_3-NH-CH-R_4 \end{array}$$

wherein
R is a hydrogen atom or a fatty acid residue;
R$_1$ is a hydroxy or amino radical;
R$_2$ is a carboxy or an N-glycyl or N-D-alanyl residue;
R$_3$ is a hydrogen atom, a fatty acid residue, a glycyl or D-alanyl radical or a glycyl or D-alanyl radical in which the amino group is substituted by a fatty acid residue; and at least one of the symbols R$_2$ and R$_3$ represent a glycyl or a D-alanyl residue and at least one of the symbols R and R$_3$ contains or is a fatty acid residue; and R$_4$ is a hydrogen or carbamoyl; the alanine bonded to the glutamic acid being in the L form; the glutamic acid being in the D form, the lysine, when R$_4$ represents a hydrogen atom, being in the L form, and the 2,6-diaminopimelamic acid, when R$_4$ represents a carbamoyl radical, being in the D,D, L,L, D,D/L,L (racemic) or D,L (meso) form; or a salt thereof.

2. A peptide according to claim 1 wherein R represents an alkanoyl radical containing 3 to 22 carbon atoms or an alkanoyl radical containing 3 to 22 carbon atoms which is substituted by a cyclohexyl radical, or a salt thereof.

3. A peptide according to claim 1 wherein R represents an alkanoyl radical containing 8 to 16 carbon atoms, $R_1$ represents a hydroxy radical, $R_2$ and $R_4$ are as defined in claim 1 and $R_3$ represents a hydrogen atom or a glycyl or D-alanyl residue, or a salt thereof.

4. A compound according to claim 1 which is $N^2$-[N-(N-lauroyl-L-alanyl)-γ-D-glutamyl]-$N^6$-glycyl-D,D/L,L-2,6-diaminopimelamic acid, or a salt thereof.

5. A compound according to claim 1 which is $N^2$-[N-(N-lauroyl-L-alanyl)-γ-D-glutamyl]-$N^6$-glycyl-D,D,/L,L-2,6-diaminopimelamic acid hydrochloride.

6. A compound according to claim 1 which is N-α-[N-(N-lauroyl-L-alanyl)-γ-D-glutamyl]-N-ε-glycyl-L-lysine hydrochloride.

7. A compound according to claim 1 which is N-α-[N-(N-lauroyl-L-alanyl)-γ-D-glutamyl]-N-ε-glycyl-L-lysine or a salt thereof.

8. A compound according to claim 1 which is N-α-[N-(N-lauroyl-L-alanyl)-γ-D-glutamyl]-L-lysyl-D-alanine or a salt thereof.

9. A compound according to claim 1 which is N-α-[N-(N-lauroyl-L-alanyl)-γ-D-glutamyl]-L-lysyl-glycine or a salt thereof.

10. A compound according to claim 1 which is N-α-[N-L-alanyl-γ-D-glutamyl]-N-ε-(N-lauroylglycyl)-L-lysine hydrochloride.

11. A compound according to claim 1 which is N-α-[N-(N-lauroyl-L-alanyl)-γ-D-glutamyl]-N-ε-(lauroylglycyl)-L-lysine or a salt thereof.

12. A compound according to claim 1 which is $N^2$-[N-(N-lauroyl-L-alanyl)-γ-D-glutamyl]-D,D/L,L-2,6-diaminopimelamoyl-glycine or a salt thereof.

13. A compound according to claim 1 which is $N^2$-[N-(N-lauroyl-L-alanyl)-D-isoglutaminyl]-$N^6$-(glycyl)-D,D/L,L-2,6-diaminopimelamic acid or a salt thereof.

14. A compound according to claim 1 which is $N^2$-[N-(N-octanoyl-L-alanyl)-γ-D-glutamyl]-$N^6$-(glycyl)-D,D/L,L-2,6-diaminopimelamic acid or a salt thereof.

15. A compound according to claim 1 which is $N^2$-[N-(N-palmitoyl-L-alanyl)-γ-D-glutamyl]-$N^6$-glycyl-D,D/L,L-2,6-diaminopimelamic acid or a salt thereof.

16. A compound according to claim 1 which is N-α-[N-(N-lauroyl-L-alanyl)-γ-D-glutamyl]-N-ε-glycyl-L-lysyl-D-alanine or a salt thereof.

17. A compound according to claim 1 which is $N^2$-[N-(N-lauroyl-L-alanyl)-γ-D-glutamyl]-$N^6$-glycyl-D,D/L,L-2,6-diaminopimelamoyl-D-alanine or a salt thereof.

18. A compound according to claim 1 which is $N^2$-[N-(N-docosanoyl-L-alanyl)-γ-D-glutamyl]-$N^6$-glycyl-L-lysine, $N^2$-{N-[N-(3-cyclohexylpropionyl)-L-alanyl]-γ-D-glutamyl}-$N^6$-glycyl-L-lysine, $N^2$-{N-[N-(3,5,5-trimethylhexanoyl)-L-alanyl]-γD-glutamyl}-$N^6$-glycyl-D,D/L,L-2,6-diaminopimelamic acid, N-α-{N-[N-(3,5,5-trimethylhexanoyl)-L-alanyl]-γ-D-glutamyl}-N-ε-glycyl-L-lysine, N-α-[N-(N-nonanoyl-L-alanyl)-γ-D-glutamyl]-N-ε-glycyl-L-lysine hydrobromide, $N^2$-[N-(N-lauroyl-L-alanyl)-γ-D-glutamyl]-$N^6$-glycyl-L,L-2,6-diaminopimelamic acid, $N^2$-[N-(N-lauroyl-L-alanyl)-γ-D-glutamyl]-$N^6$-(N-acetylglycyl)-D,D/L,L-2,6-diaminopimelamic acid, $N^2$-[N-(N-lauroyl-L-alanyl)-γ-D-glutamyl]-$N^6$-D-alanyl-D,D/L,L-2,6-diaminopimelamic acid, $N^2$-[N-(N-undecanoyl-L-alanyl)-γ-D-glutamyl]-$N^6$-glycyl-L,L/D,D-2,6-diaminopimelamic acid, $N^2$-[N-(N-lauroyl-L-alanyl)-γ-D-glutamyl]-$N^6$-glycyl-meso-2(L),6(D)-diaminopimelamic acid, or N-α-[N-(N-hexanoyl-L-alanyl)-γ-D-glutamyl]-N-ε-glycyl-L-lysine hydrobromide, or a salt thereof.

19. A pharmaceutical composition useful as a vaccine adjuvant or as a non-specific stimulant of anti-infectious immunity which comprises an effective amount of a peptide according to claim 1 or a non-toxic salt thereof in association with a pharmaceutically acceptable carrier or diluent.

20. A method of increasing cell immunity reactions or the production of circulating or local antibodies in man or a domestic animal which comprises the administration of an effective amount of a peptide according to claim 1 or a non-toxic salt thereof and an antigen.

21. A method for the non-specific stimulation of anti-infectious immunity in man or a domestic animal which comprises the administration of an effective amount of a peptide according to claim 1 or a non-toxic salt thereof.

* * * * *

UNITED STATES PATENT AND TRADEMARK OFFICE
CERTIFICATE OF CORRECTION

PATENT NO. : 4,742,048

DATED : May 3, 1988

INVENTOR(S) : BOUCHAUDON et al.

It is certified that error appears in the above-identified patent and that said Letters Patent is hereby corrected as shown below:

In the heading at "[73]", for the name of the "assignee" read --Rhone-Poulenc Sante--.

Signed and Sealed this

Second Day of July, 1991

Attest:

HARRY F. MANBECK, JR.

*Attesting Officer*      *Commissioner of Patents and Trademarks*